United States Patent
Lewis et al.

(10) Patent No.: US 10,301,294 B2
(45) Date of Patent: May 28, 2019

(54) COMPOUNDS FOR THE TREATMENT OF TUBERCULOSIS

(71) Applicants: THE BROAD INSTITUTE, INC., Cambridge, MA (US); MASSACHUSETTS GENERAL HOSPITAL, Boston, MA (US); BRIGHAM AND WOMEN'S HOSPITAL, Boston, MA (US)

(72) Inventors: Timothy A. Lewis, Marlborough, MA (US); Sivaraman Dandapani, Malden, MA (US); Deborah Hung, Cambridge, MA (US); Benito Munoz, Newtonville, MA (US); Partha Nag, Somerville, MA (US); Sarah Grant, Boston, MA (US); Tomohiko Kawate, Cambridge, MA (US)

(73) Assignees: THE BROAD INSTITUTE INC., Cambridge, MA (US); MASSACHUSETTS GENERAL HOSPITAL, Boston, MA (US); BRIGHAM AND WOMEN'S HOSPITAL, Boston, MA (US)

(*) Notice: Subject to any disclaimer, the term of this patent is extended or adjusted under 35 U.S.C. 154(b) by 0 days.

(21) Appl. No.: 14/776,477

(22) PCT Filed: Mar. 12, 2014

(86) PCT No.: PCT/US2014/024344
§ 371 (c)(1),
(2) Date: Sep. 14, 2015

(87) PCT Pub. No.: WO2014/165090
PCT Pub. Date: Oct. 9, 2014

(65) Prior Publication Data
US 2016/0031870 A1 Feb. 4, 2016

Related U.S. Application Data

(60) Provisional application No. 61/779,051, filed on Mar. 13, 2013.

(51) Int. Cl.
| | | |
|---|---|---|
| *C07D 413/12* | (2006.01) | |
| *C07D 271/113* | (2006.01) | |
| *C07D 271/10* | (2006.01) | |
| *C07D 413/14* | (2006.01) | |
| *C07D 413/04* | (2006.01) | |
| *C07D 417/04* | (2006.01) | |
| *C07D 417/12* | (2006.01) | |
| *C07D 263/46* | (2006.01) | |
| *C07D 285/125* | (2006.01) | |

(52) U.S. Cl.
CPC ......... *C07D 413/12* (2013.01); *C07D 263/46* (2013.01); *C07D 271/10* (2013.01); *C07D 271/113* (2013.01); *C07D 285/125* (2013.01); *C07D 413/04* (2013.01); *C07D 413/14* (2013.01); *C07D 417/04* (2013.01); *C07D 417/12* (2013.01)

(58) Field of Classification Search
CPC ........................ C07D 413/12; C07D 271/113
See application file for complete search history.

(56) References Cited

U.S. PATENT DOCUMENTS

2011/0028466 A1* 2/2011 Thompson ............ C07D 498/04
514/230.5
2012/0065196 A1* 3/2012 Kitamura ............. C07D 231/14
514/227.8

FOREIGN PATENT DOCUMENTS

| EP | 2316836 A1 | 5/2011 |
| WO | 2002094796 A2 | 11/2002 |
| WO | 2010145208 A1 | 12/2010 |

OTHER PUBLICATIONS

Macaev et al. Bioorg. Med. Chem. 2005, 13, 4842-4850.*
Collins et al. Antimicrob. Agents Chemother. 1997, 41, 1004-1009.*
National Center for Biotechnology Information. PubChem BioAssay Database; AID=651619, https://pubchem.ncbi.nlm.nih.gov/bioassay/651619 (accessed Jul. 16, 2017, Version 1.1 dated Oct. 4, 2012).*
National Center for Biotechnology Information. PubChem BioAssay Database; AID=651620, https://pubchem.ncbi.nlm.nih.gov/bioassay/651620 (accessed Jul. 16, 2017, Version 1.1 dated Oct. 4, 2012).*
National Center for Biotechnology Information. PubChem BioAssay Database; AID=651857, https://pubchem.ncbi.nlm.nih.gov/bioassay/651857 (accessed Jul. 16, 2017, Version 1.1 dated Dec. 4, 2012).*
National Center for Biotechnology Information. PubChem Compound Database; CID=60182306, https://pubchem.ncbi.nlm.nih.gov/compound/60182306 (accessed Jul. 16, 2017, created Sep. 27, 2012).*
Filippini et al. Antimicrob. Agents Chemother. 2010, 54, 2712-2715.*
Ananthan et al. Tuberculosis 2009, 89, 334-353.*
National Center for Biotechnology Information. PubChem BioAssay Database; AID=651618, https://pubchem.ncbi.nlm.nih.gov/bioassay/651618 (accessed Dec. 12, 2017, hold-until date Nov. 21, 2012).*
National Center for Biotechnology Information. PubChem Compound Database; CID=2843335, https://pubchem.ncbi.nlm.nih.gov/compound/2843335 (accessed Dec. 12, 2017, created Jul. 28, 2005).*

(Continued)

*Primary Examiner* — Matthew P Coughlin
(74) *Attorney, Agent, or Firm* — Pepper Hamilton LLP

(57) ABSTRACT

Disclosed are compounds that can be used for treating tuberculosis.

5 Claims, 1 Drawing Sheet

(56) References Cited

OTHER PUBLICATIONS

National Center for Biotechnology Information. PubChem BioAssay Database; AID=651683, https://pubchem.ncbi.nlm.nih.gov/bioassay/651683 (deposit Oct. 22, 2012; accessed Feb. 28, 2018). (Year: 2012).*
National Center for Biotechnology Information. PubChem Compound Database; CID=856031, https://pubchem.ncbi.nlm.nih.gov/compound/856031 (create date Jul. 9, 2005; accessed Feb. 28, 2018) (Year: 2005).*
National Center for Biotechnology Information. PubChem BioAssay Database; AID=540299, https://pubchem.ncbi.nlm.nih.gov/bioassay/540299 (deposit date Jul. 25, 2011; accessed Feb. 28, 2018). (Year: 2011).*
National Center for Biotechnology Information. PubChem Compound Database; CID=851270, https://pubchem.ncbi.nlm.nih.gov/compound/851270 (create date Jul. 9, 2005; accessed Feb. 28, 2018). (Year: 2005).*
National Center for Biotechnology Information. PubChem BioAssay Database; AID=540299, https://pubchem.ncbi.nlm.nih.gov/bioassay/540299 (deposit date Jul. 25, 2011; accessed Jun. 22, 2018) (Year: 2011).*
Li et al. ACS Med. Chem. Lett. 2011, 2, 818-823 (Year: 2011).*
Cho et al. Antimicrobial Agents and Chemotherapy 2007, 51, 1380-1385 (Year: 2007).*
Pubchem, AID 651618, Counterscreen for Inhibitors of Non Replicating M. tb Using Log Phase Replicating Mycobacteria Measured in Microorganism System Using Plate Reader—2157-02_Inhibitor-Dose_DryPowder_Activity_Set2; Nov. 21, 2012, pp. 1-6 (online), [retrieved on May 19, 2014] Retrieved from the internet <URL: http://pubchem.ncbi.nim.nih.gov/assay/assay.cgi?aid=651618>; p. 2, paragraph 2; p. 4, table, lines 2, 9, 20.
Pubchem, AID 488929, Elucidation of Physiology of Non-Replicating, Drug-Tolerant *Mycobacterium tuberculosis* Summary, Dec. 27, 2010, pp. 1-3 (online), [retrieved on May 19, 2014] Retrieved from the internet <URL:http://pubchem.ncbi.nim.nih.gov/assay/assay.cgi?aid=488929&version=1.3>; p. 2, paragraphs 3-4.
Pubchem, SID 126722820, Nov. 21, 2012, pp. 1-2 [online], [retrieved on May 19, 2014], retrieved from the internet <URL: http://pubchem.ncbi.nim.nih.gov/summary/summary.cgi?sid=126722820>; p. 1, formula.
Pubchem, SID 126722795, Nov. 21, 2012, pp. 1-2 [online], [retrieved on May 19, 2014], retrieved from the internet <URL: http://pubchem.ncbi.nim.nih.gov/summary/summary.cgi?sid=126722795>; p. 1, formula.
Pubchem, SID 126722809, Nov. 21, 2012, pp. 1-2 [online], [retrieved on May 19, 2014] Retrieved from the internet <URL: http://pubchem.ncbi.nim.nih.gov/summary/sumary.cgi?sid+126722809>:p. 1, formula.
International Search Report and Written Opinion for corresponding PCT/US2014/24344 dated Jul. 1, 2014.

* cited by examiner

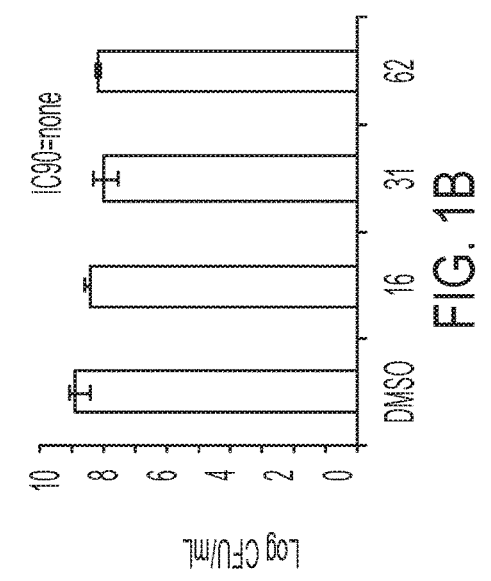
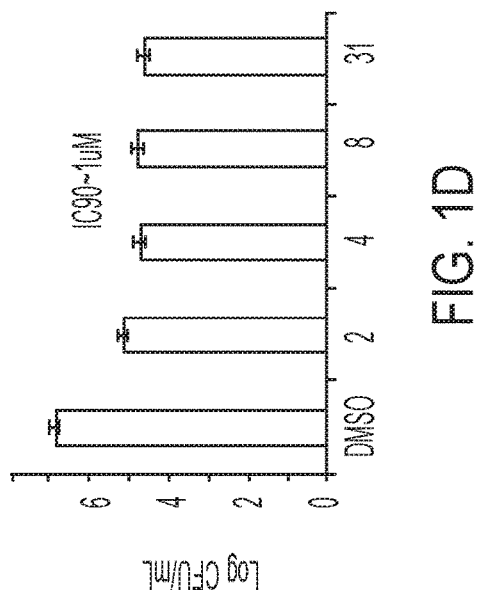
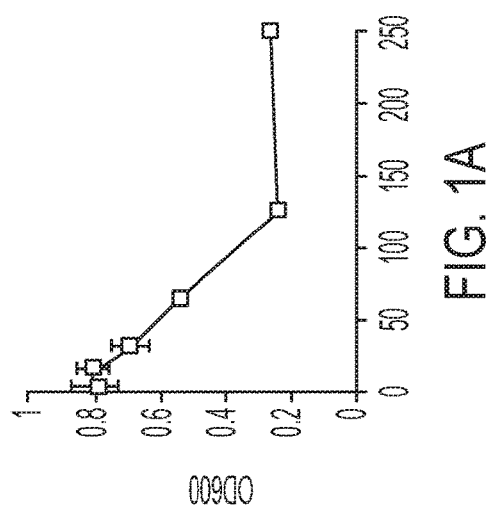
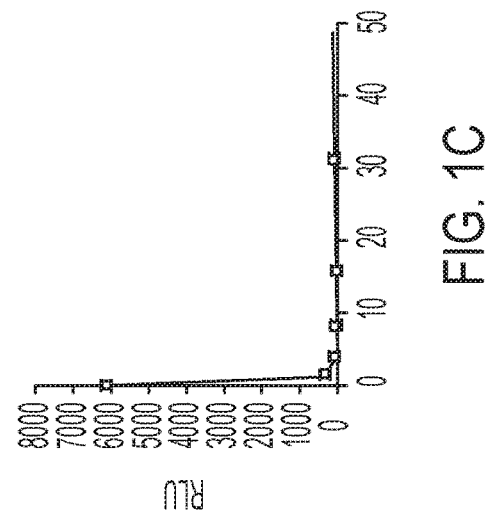

COMPOUNDS FOR THE TREATMENT OF TUBERCULOSIS

CROSS-REFERENCE TO RELATED APPLICATIONS

This application is a National Stage Entry of PCT application No. PCT/US2014/0241344 filed Mar. 12, 2014, which claims priority to U.S. Provisional Application No. 61/779,051 filed Mar. 13, 2013, which is hereby incorporated by reference in its entirety.

REFERENCE TO GOVERNMENT GRANTS

This invention was made with government support under Grant No. 1R03MH087444, awarded by the National Institutes of Health, and under Grant No. 1K08AI085033, awarded by the National Institutes of Health. The U.S. Government may therefore have certain rights in the invention.

FIELD OF THE INVENTION

The present invention is directed, in part, to compounds or pharmaceutically acceptable salts thereof, for treating tuberculosis.

BACKGROUND OF THE INVENTION

The problem of tuberculosis continues to take a tremendous toll on global health, accounting for almost 2 million deaths per year, despite the discovery of antitubercular chemotherapy more than half a century ago. In fact, the crisis is growing due to the alarming increase in multi-drug resistant, and even totally-drug resistant strains, coupled with the extremely little progress made in discovering new TB drugs. One of the major barriers to discovering new, potentially more effective agents has been the lack of a fundamental understanding of the physiology of the *M. tuberculosis* bacilli as they exist within the infected human host. This physiology contributes to their ability to survive for decades within an infected individual despite host immunity, and to persist even in the face of what should otherwise be effective chemotherapy thus dictating the extremely long treatment courses that are required for cure. Accordingly, there is a need for new compounds and therapeutics for treating tuberculosis. The present disclosure fulfills these needs as well as others.

SUMMARY OF THE INVENTION

In some embodiments, pharmaceutical compositions are provided. In some embodiments, the pharmaceutical composition comprises a compound of Formula I or a pharmaceutically acceptable salt, ester or prodrug thereof:

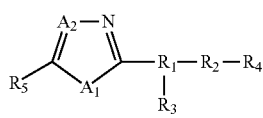

Formula I wherein:
$A_1$, is S or O;
$A_2$ is C or N;
$R_1$ is S, N, O, optionally substituted $C_1$-$C_6$ linear or branched alkyl, or sulfonyl,
$R_2$ is null or optionally substituted linear or branched $C_1$-$C_{12}$ alkyl;
$R_3$ is null, O, H, optionally substituted $C_1$-$C_6$ linear or branched alkyl,

$R_4$ is H, an optionally substituted aryl, an optionally substituted heteroaryl, an optionally substituted heterocycle, optionally substituted $C_1$-$C_6$ alkoxy, or an optionally substituted amide;
$R_5$ is an optionally substituted aryl, optionally substituted arylalkyl, optionally substituted heteroaryl, optionally substituted $C_4$-$C_6$ carbocycle, or optionally substituted $C_1$-$C_6$ linear or branched alkyl.

In some embodiments, the pharmaceutical composition comprises a compound described herein.

In some embodiments, a compound of Formula I or a pharmaceutically acceptable salt, ester or prodrug thereof:

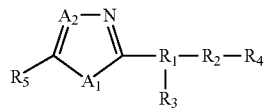

Formula I wherein:
$A_1$, is S or O;
$A_2$ is C or N;
$R_1$ is S, N, O, optionally substituted $C_1$-$C_6$ linear or branched alkyl, or sulfonyl,
$R_2$ is null or optionally substituted linear or branched $C_1$-$C_{12}$ alkyl;
$R_3$ is null, O, H, optionally substituted $C_1$-$C_6$ linear or branched alkyl,

$R_4$ is H, an optionally substituted aryl, an optionally substituted heteroaryl, an optionally substituted heterocycle, optionally substituted $C_1$-$C_6$ alkoxy, or an optionally substituted amide;
$R_5$ is an optionally substituted aryl, optionally substituted arylalkyl, optionally substituted heteroaryl, optionally substituted $C_4$-$C_6$ carbocycle, or optionally substituted $C_1$-$C_6$ linear or branched alkyl is provided.

In some embodiments, a method of treating tuberculosis comprising administering to a subject a pharmaceutical composition described herein or a compound described herein is provided. In some embodiments, the tuberculosis is replicating.

In some embodiments, the tuberculosis is non-replicating. In some embodiments, the compound or pharmaceutical composition selectively inhibits replicating or non-replicating tuberculosis.

BRIEF DESCRIPTION OF FIGURES

FIGS. 1A-1D described the characteristics of 2-(4-chlorophenyl)-5-(((1-phenyl-1H-1,2,3-triazol-4-yl)methyl)thio)-1,2,3,4-oxadiazole;

FIG. 1A is a dose response curve against replicating, logarithmically growing bacteria measured by OD600;

FIG. 1B is a dose response against replicating, logarithmically growing bacteria measured by CFU/mL;

FIG. 1C is a dose response curve for non-replicating starved cells by luciferase assay; and FIG. 1D is a dose response against non-replicating, starved cells by CFU/mL.

DESCRIPTION OF EMBODIMENTS

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the terms "IC90" or "IC99" when used as reference to a non-replicating population of M. tuberculosis is the inhibitory concentration of a compound or compositions that results in 90% or 99% killing of the non-replicating population of M. tuberculosis, respectively. As used herein, the terms "IC90" or "IC99" when used as reference to a replicating population of M. tuberculosis is the "inhibitory concentration" that results in 90% or 99% growth inhibition of a replicating population of M. tuberculosis.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom. For example, the term "alkoxy" means a straight or branched —O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group having from 1 to 6 carbon atoms. An example of an alkylamino is —NHCH$_2$CH$_3$.

As used herein, the term "alkylene" or "alkylenyl" means a divalent alkyl linking group. An example of an alkylene (or alkylenyl) is methylene or methylenyl (—CH$_2$—).

As used herein, the term "alkylthio" means an —S-alkyl group having from 1 to 6 carbon atoms. An example of an alkylthio group is —SCH$_2$CH$_3$.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means —C(=NH)NH$_2$.

As used herein, the term "amino" means —NH$_2$.

As used herein, the term "aminoalkoxy" means an alkoxy group substituted by an amino group. An example of an aminoalkoxy is —OCH$_2$CH$_2$NH$_2$.

As used herein, the term "aminoalkyl" means an alkyl group substituted by an amino group. An example of an aminoalkyl is —CH$_2$CH$_2$NH$_2$.

As used herein, the term "aminosulfonyl" means —S(=O)$_2$NH$_2$.

As used herein, the term "aminoalkylthio" means an alkylthio group substituted by an amino group. An example of an aminoalkylthio is —SCH$_2$CH$_2$NH$_2$.

As used herein, the term "animal" includes, but is not limited to, humans and non-human vertebrates such as wild, domestic, and farm animals.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like. Examples of aryl groups include, but are not limited to:

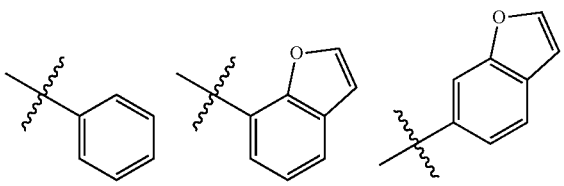

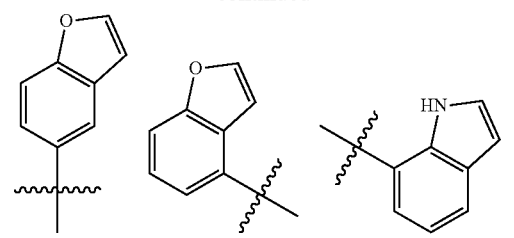
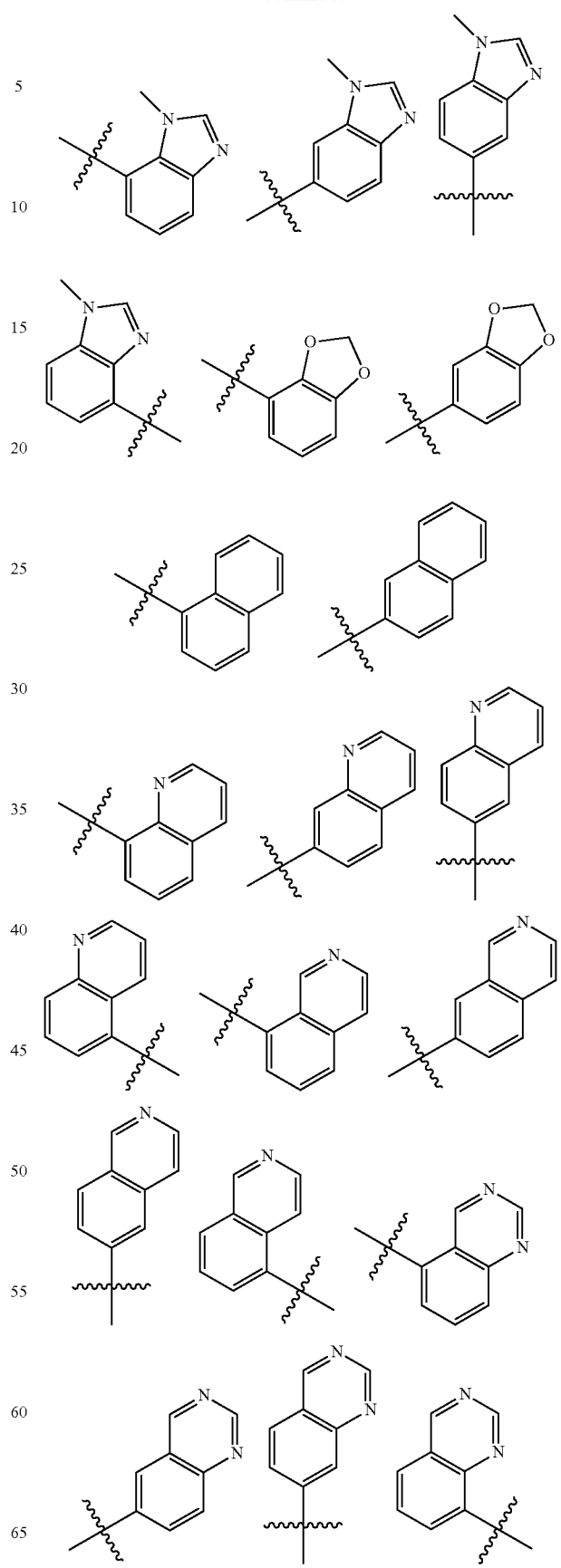

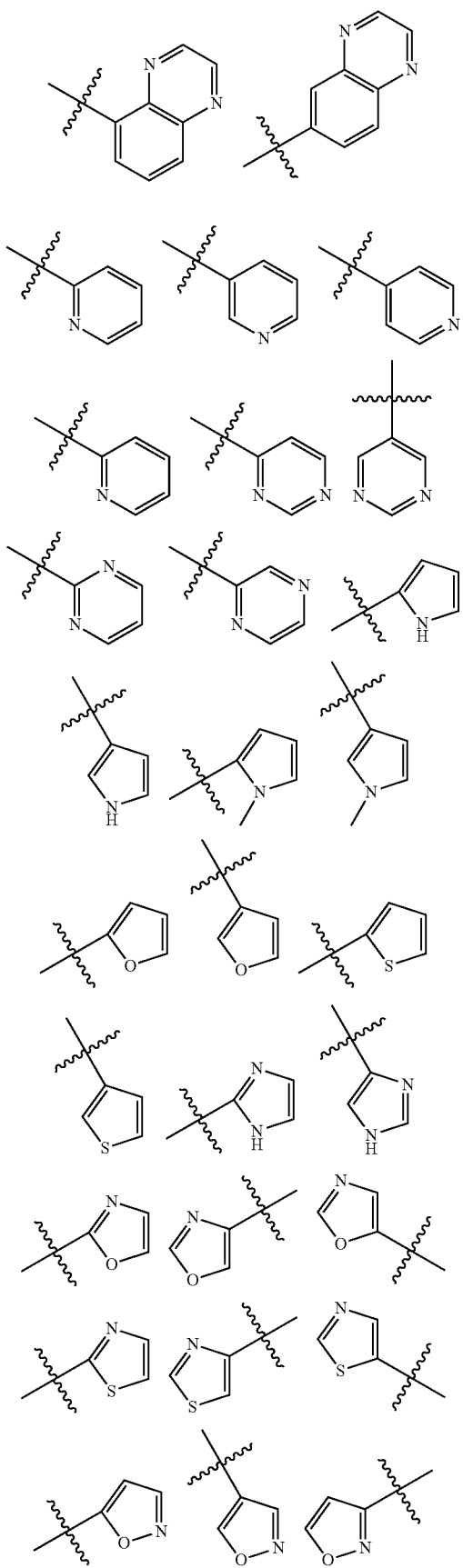
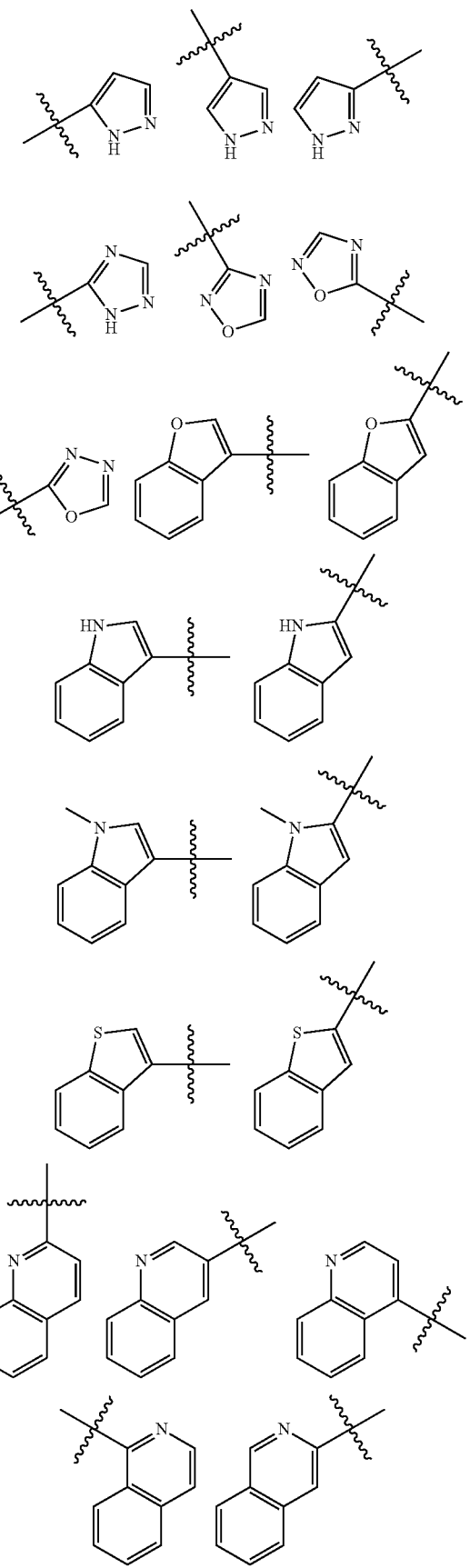

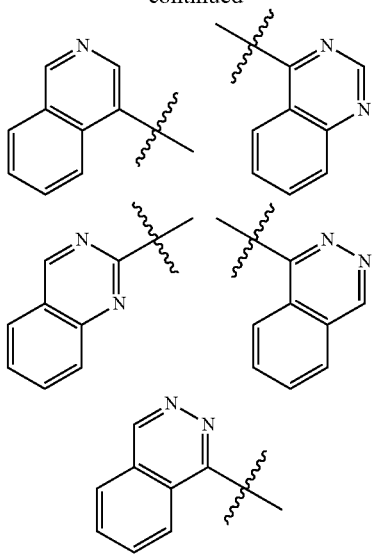

As used herein, the term "arylalkyl" means a $C_{1-6}$alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

As used herein, the term "carbamoyl" means —C(=O)—NH$_2$.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used. As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "cycloalkylalkyl" means a $C_{1-6}$alkyl substituted by cycloalkyl.

As used herein, the term "dialkylamino" means an amino group substituted by two alkyl groups, each having from 1 to 6 carbon atoms.

As used herein, the term "diazamino" means —N(NH$_2$)$_2$.

As used herein, the term "guanidino" means —NH(=NH)NH$_2$.

As used herein, the term "halo" means halogen groups including, but not limited to fluoro, chloro, bromo, and iodo.

As used herein, the term "haloalkoxy" means an —O-haloalkyl group. An example of an haloalkoxy group is OCF$_3$.

As used herein, the term "haloalkyl" means a $C_{1-6}$alkyl group having one or more halogen substituents. Examples of haloalkyl groups include, but are not limited to, CF$_3$, C$_2$F$_5$, CHF$_2$, CCl$_3$, CHCl$_2$, C$_2$Cl$_5$, CH$_2$CF$_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "heteroarylamino" means an amino group substituted by a heteroaryl group. An example of a heteroarylamino is —NH-(2-pyridyl).

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means nonaromatic heterocycles having up to 20 ring-forming atoms including cyclized alkyl, alkenyl, and alkynyl groups, where one or more of the ring-forming carbon atoms is replaced by a heteroatom such as an O, N, or S atom. Heterocycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Also included in the definition of heterocloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" refers to a $C_{1-6}$alkyl substituted by heterocycloalkyl.

As used herein, the term "hydoxy" or "hydroxyl" means an —OH group.

As used herein, the term "hydroxyalkyl" or "hydroxylalkyl" means an alkyl group substituted by a hydroxyl group. Examples of a hydroxylalkyl include, but are not limited to, —CH$_2$OH and —CH$_2$CH$_2$OH.

As used herein, the term "individual" or "patient," used interchangeably, means any animal, including mammals, such as mice, rats, other rodents, rabbits, dogs, cats, swine, cattle, sheep, horses, or primates, such as humans. The individual can also be referred to as a subject.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the phrase "integer from X to Y" means any integer that includes the endpoints. For example, the phrase "integer from X to Y" means 1, 2, 3, 4, or 5.

As used herein, the term "isolated" means that the compounds described herein are separated from other components of either (a) a natural source, such as a plant or cell, or (b) a synthetic organic chemical reaction mixture, such as by conventional techniques.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "nitro" means —NO$_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfate, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present invention also includes quaternary ammonium salts of the compounds described herein, where the compounds have one or more tertiary amine moiety.

As used herein, the term "phenyl" means —$C_6H_5$. A phenyl group can be unsubstituted or substituted with one, two, or three suitable substituents.

As used herein, the terms "prevention" or "preventing" mean a reduction of the risk of acquiring a particular disease, condition, or disorder.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, —CN, —OH, oxo, halo, haloalkyl, —$NO_2$, —$CO_2H$, —$NH_2$, —NH($C_1$-$C_5$alkyl), —N($C_1$-$C_5$alkyl)$_2$, —NH($C_6$aryl), —N($C_5$-$C_6$aryl)$_2$, —CHO, —CO($C_1$-$C_6$alkyl), —CO(($C_5$-$C_6$)aryl), —$CO_2$(($C_1$-$C_6$)alkyl), and —$CO_2$(($C_5$-$C_6$)aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of tuberculosis" or "treating tuberculosis" means an activity that prevents, alleviates or ameliorates any of the primary phenomena (initiation, progression, metastasis) or secondary symptoms associated with the tuberculosis. As used herein, the phrase "treating tuberculosis" or "treatment of tuberculosis" also refers to the treatment of a subject infected with *M. tuberculosis* bacilli. The treatment can target replicating *M. tuberculosis* bacilli and/or non-replicating *M. tuberculosis* bacilli. In some embodiments, the compounds can selectively target one form (e.g. non-replicating or replicating) of *M. tuberculosis* bacilli.

At various places in the present specification, substituents of compounds may be disclosed in groups or in ranges. It is specifically intended that embodiments include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

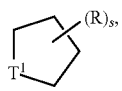

then it is understood that substituent R can occur s number of times on the ring, and R can be a different moiety at each occurrence. Further, in the above example, where the variable $T^1$ is defined to include hydrogens, such as when $T^1$ is $CH_2$, NH, etc., any H can be replaced with a substituent.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

It is understood that the present invention encompasses the use, where applicable, of stereoisomers, diastereomers and optical stereoisomers of the compounds of the invention, as well as mixtures thereof. Additionally, it is understood that stereoisomers, diastereomers, and optical stereoisomers of the compounds of the invention, and mixtures thereof, are within the scope of the invention. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the invention unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallizaion using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art. Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti-arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds also include derivatives referred to as prodrugs.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

Embodiments of various compounds and salts thereof are provided. Where a variable is not specifically recited, the variable can be any option described herein, except as otherwise noted or dictated by context.

In some embodiments, a compound of Formula I or a pharmaceutically acceptable salt, ester or prodrug thereof is provided:

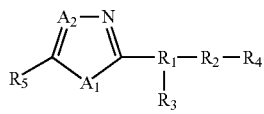

Formula I wherein:

$A_1$ is S or O;

$A_2$ is C or N;

$R_1$ is S, N, O, optionally substituted $C_1$-$C_6$ linear or branched alkyl, or sulfonyl, $R_2$ is null or optionally substituted linear or branched $C_1$-$C_{12}$ alkyl;

$R_3$ is null, O, H, optionally substituted $C_1$-$C_6$ linear or branched alkyl,

$R_4$ is H, an optionally substituted aryl, an optionally substituted heteroaryl, an optionally substituted heterocycle, optionally substituted $C_1$-$C_6$ alkoxy, or an optionally substituted amide;

$R_5$ is an optionally substituted aryl, optionally substituted arylalkyl, optionally substituted heteroaryl, optionally substituted $C_4$-$C_6$ carbocycle, or optionally substituted $C_1$-$C_6$ linear or branched alkyl.

In some embodiments, embodiments, $R_4$ is H,

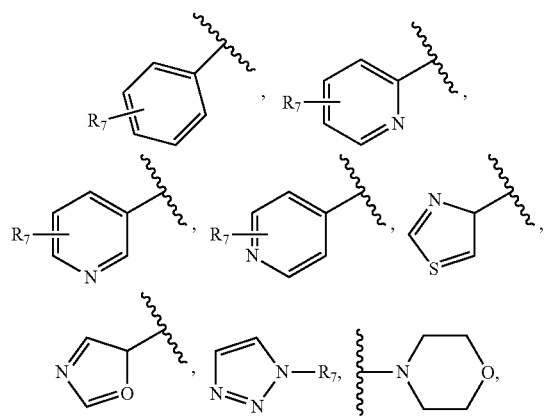

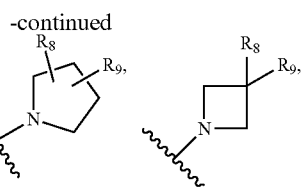

optionally substituted $C_1$-$C_6$ alkoxy, or optionally substituted alkylamino, wherein $R_7$ is H,

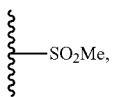

halo, cyano, $C_1$-$C_6$ alkoxy, linear or branched alkyl, haloalkyl, optionally substituted aryl; optionally substituted arylalkyl, halogen substituted $C_1$-$C_6$ alkoxy; and $R_8$ and $R_9$ are independently H, OH, halo, or $C_1$-$C_6$ alkyl.

In some embodiments, $R_5$ is $C_1$-$C_6$ linear or branched alkyl,

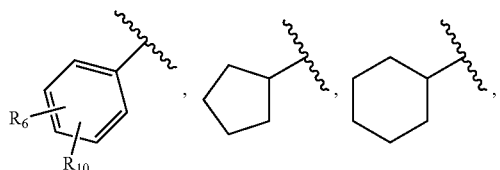

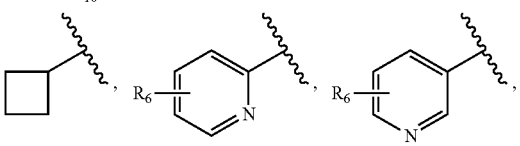

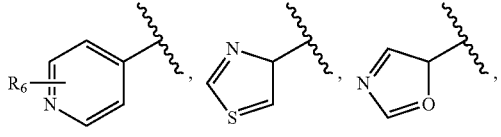

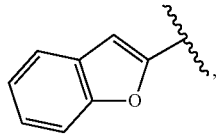

wherein $R_6$ and $R_{10}$ are each independently H, halo, optionally substituted aryl, $C_1$-$C_6$ linear or branched alkyl, $C_1$-$C_6$ alkoxy, haloalkyl, halogen substituted $C_1$-$C_6$ alkoxy, cyano, or

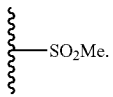

In some embodiments, $A_1$ is O. In some embodiments, wherein $A_2$ is N. In some embodiments, $R_1$ is S. In some embodiments, $R_3$ is null. In some embodiments, $R_2$ is null or $C_1$-$C_{12}$ alkyl.

In some embodiments, $A_1$ is O; $A_2$ is N; $R_1$ is S; and $R_3$ is null.

In some embodiments, the compound has the Formula I-a, or a pharmaceutically acceptable salt, ester or prodrug thereof:

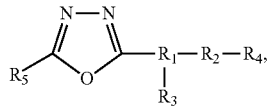

I-a wherein:

$R_1$ is S, N, O, optionally substituted $C_1$-$C_6$ linear or branched alkyl, or sulfonyl, $R_2$ is null or optionally substituted linear or branched $C_1$-$C_{12}$ alkyl.

$R_3$ is null, O, H, optionally substituted $C_1$-$C_6$ linear or branched alkyl,

$R_4$ is H, an optionally substituted aryl, an optionally substituted heteroaryl, an optionally substituted heterocycle, optionally substituted $C_1$-$C_6$ alkoxy, or an optionally substituted amide;

$R_5$ is an optionally substituted aryl, optionally substituted arylalkyl, optionally substituted heteroaryl, optionally substituted $C_4$-$C_6$ carbocycle, or optionally substituted $C_1$-$C_6$ linear or branched alkyl.

In some embodiments, $R_5$ is $C_1$-$C_6$ linear or branched alkyl,

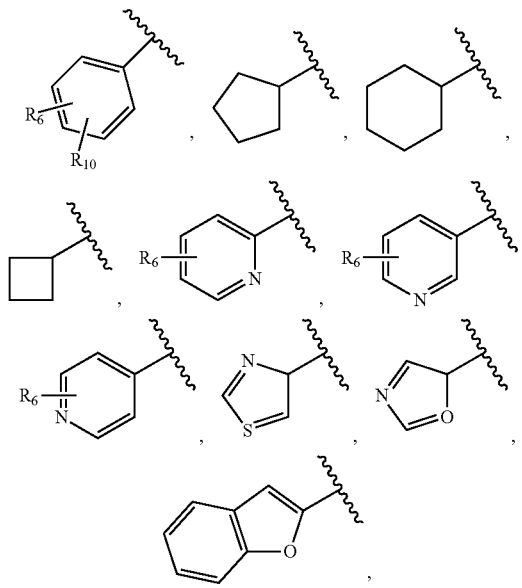

wherein $R_6$ and $R_{10}$ are each independently H, halo, optionally substituted aryl, $C_1$-$C_6$ linear or branched alkyl, $C_1$-$C_6$ alkoxy, haloalkyl, halogen substituted $C_1$-$C_6$ alkoxy, cyano, or

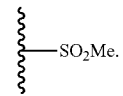

In some embodiments, $R_5$ is:

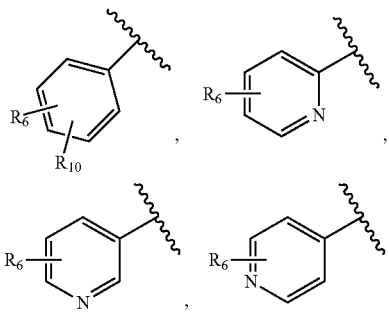

wherein $R_6$ and $R_{10}$ are each independently H, halo, $C_1$-$C_6$ linear or branched alkyl, $C_1$-$C_6$ haloalkyl, cyano, $C_1$-$C_6$ alkoxy, halogen substituted $C_1$-$C_6$ alkoxy, OH, —O(CH$_2$)$_q$C(=O)O(CH$_2$)$_p$CH$_3$, —O(CH$_2$)$_q$C(=O)N(H)(CH$_2$)$_p$O(CH$_2$)$_m$N$_3$, —O(CH$_2$)$_q$C≡CH, or

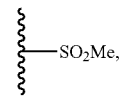

wherein m, p and q are independently 1-4. In some embodiments, $R_5$ is

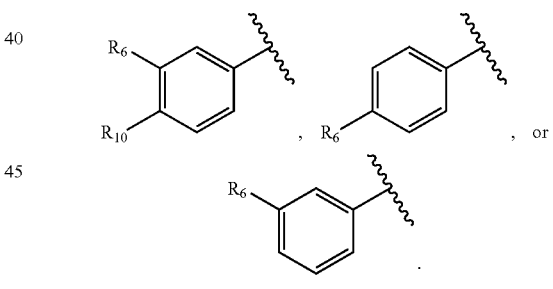

In some embodiments, $R_6$ is H, halo, methyl, ethyl, or propyl, CF$_3$, cyano, OH, —O(CH$_2$)$_q$C(=O)O(CH$_2$)$_p$CH$_3$, —O(CH$_2$)$_q$C(=O)N(H)(CH$_2$)$_p$O(CH$_2$)$_m$N$_3$, or —O(CH$_2$)$_q$C≡CH and $R_{10}$ is H. In some embodiments, $R_6$ and $R_{10}$ are both H, methyl, ethyl, or propyl, CF$_3$, halo, $C_1$-$C_6$ alkoxy, OH, —O(CH$_2$)$_q$C(=O)O(CH$_2$)$_p$CH$_3$, —O(CH$_2$)$_q$C(=O)N(H)(CH$_2$)$_p$O(CH$_2$)$_m$N$_3$, or —O(CH$_2$)$_q$C≡CH. In some embodiments, $R_6$ is halo and $R_{10}$ is H, methyl, ethyl, or propyl, CF$_3$, $C_1$-$C_6$ alkoxy, OH, —O(CH$_2$)$_q$C(=O)O(CH$_2$)$_p$CH$_3$, —O(CH$_2$)$_q$C(=O)N(H)(CH$_2$)$_p$O(CH$_2$)$_m$N$_3$, or —O(CH$_2$)$_q$C≡CH.

In some embodiments, $R_1$ is S or sulfonyl. In some embodiments, $R_1$ is N. In some embodiments, $R_1$ is O.

In some embodiments, $R_1$ is optionally substituted $C_1$-$C_6$ linear or branched alkyl.

In some embodiments, $R_1$ is S; $R_2$ null or optionally substituted linear or branched $C_1$-$C_{12}$ alkyl; $R_3$ is null or O;

and $R_4$ is H, an optionally substituted aryl, an optionally substituted heteroaryl, an optionally substituted heterocycle, optionally substituted $C_1$-$C_6$ alkoxy, or an optionally substituted amide. In some embodiments, $R_4$ is H, —C≡CH, —C≡C(CH$_2$)$_t$OH, —C(=O)O(CH$_2$)$_t$CH$_3$, —O(CH$_2$)—CH$_3$, —O(CH$_2$)$_q$C(=O)O(CH$_2$)$_p$CH$_3$,

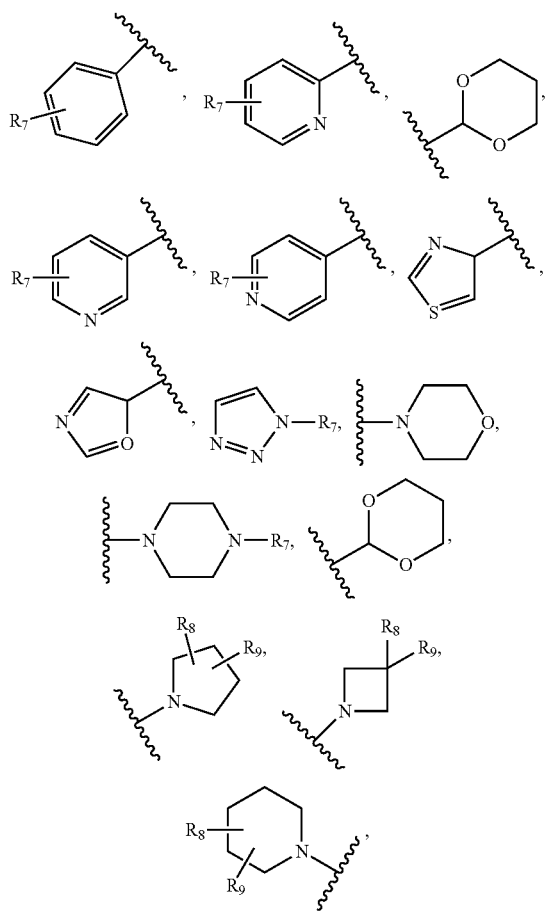

optionally substituted $C_1$-$C_6$ alkoxy, or optionally substituted alkylamino, or $C_1$-$C_6$ carbocycle, Wherein $R_7$ is H, O,

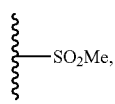

halo, cyano, —C(=O)N(H)(CH$_2$)$_p$O(CH$_2$)$_m$N$_3$, —O(CH$_2$)$_q$C(=O)N(H)(CH$_2$)$_p$O(CH$_2$)$_m$N$_3$, —O(CH$_2$)$_m$N$_3$, —O(CH$_2$)$_m$C≡CH, $C_1$-$C_6$ alkoxy, optionally substituted $C_1$-$C_6$ linear or branched alkyl, haloalkyl, optionally substituted aryl; optionally substituted arylalkyl, halogen substituted $C_1$-$C_6$ alkoxy; $R_8$ and $R_9$ are independently H, OH, =O, halo, or $C_1$-$C_6$ alkyl; m, p and q are independently 1-6; and t and u are independently 0-6.

In some embodiments, a compound, or a pharmaceutically acceptable salt, ester or prodrug thereof, of Formula I has the Formula I-b, I-c, I-d, or I-e:

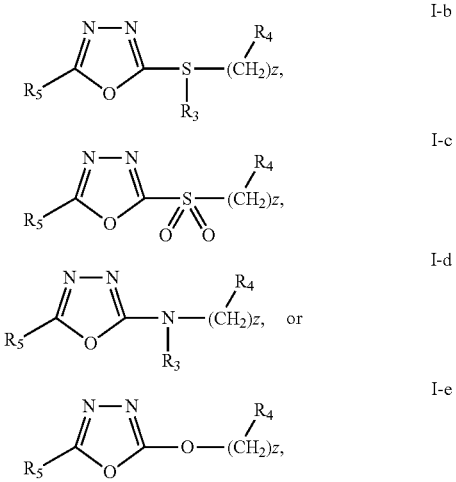

wherein
$R_4$ is H, —C≡CH, —C≡C(CH$_2$)$_t$OH, —C(=O)O(CH$_2$)$_t$CH$_3$, —O(CH$_2$)—CH$_3$, —O(CH$_2$)$_q$C(=O)O(CH$_2$)$_p$CH$_3$,

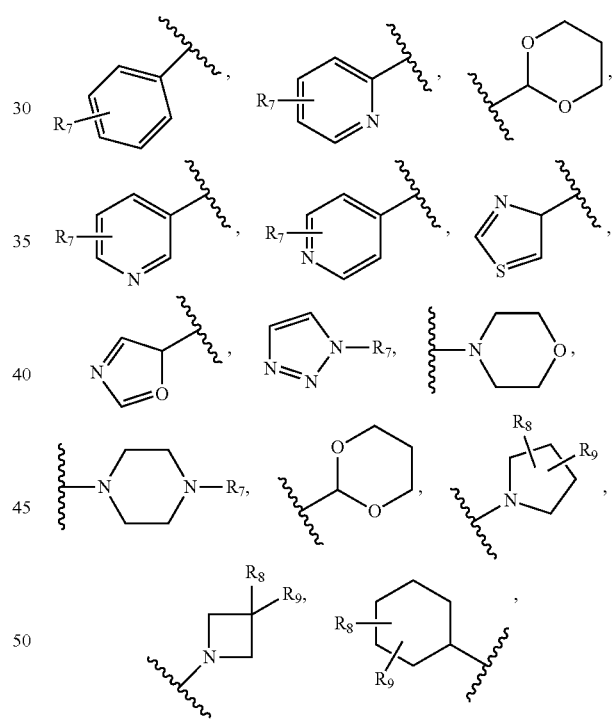

optionally substituted $C_1$-$C_6$ alkoxy, or optionally substituted alkylamino, or $C_1$-$C_6$ carbocycle,
$R_7$ is H, O,

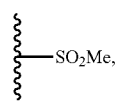

halo, cyano, —C(=O)N(H)(CH$_2$)$_p$O(CH$_2$)$_m$N$_3$, —O(CH$_2$)$_q$C(=O)N(H)(CH$_2$)$_p$O(CH$_2$)$_m$N$_3$, —O(CH$_2$)$_m$N$_3$, —O(CH$_2$)$_m$C≡CH, $C_1$-$C_6$ alkoxy, optionally substituted $C_1$-$C_6$ linear or branched alkyl, haloalkyl, optionally substituted aryl; optionally substituted arylalkyl, halogen substituted $C_1$-$C_6$ alkoxy; and $R_8$ and $R_9$ are independently H, OH, =O, halo, or $C_1$-$C_6$ alkyl;

$R_5$ is

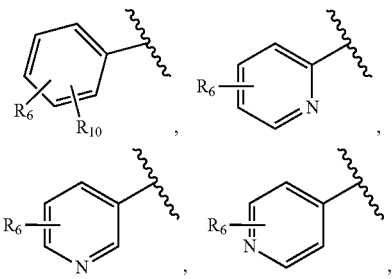

$R_6$ and $R_{10}$ are each independently H, halo, $C_1$-$C_6$ linear or branched alkyl, $C_1$-$C_6$ haloalkyl, cyano, $C_1$-$C_6$ alkoxy, halogen substituted $C_1$-$C_6$ alkoxy, OH, —O(CH$_2$)$_q$C(=O)O(CH$_2$)$_p$CH$_3$, —O(CH$_2$)$_q$C(=O)N(H)(CH$_2$)$_p$O(CH$_2$)$_m$N$_3$, —O(CH$_2$)$_q$C≡CH, or

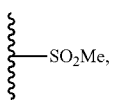

wherein m, p, q, and z are independently 1-6; and t and u are independently 0-6.

In some embodiments, the compound, or a pharmaceutically acceptable salt, ester or prodrug thereof, is selected from the group consisting of:

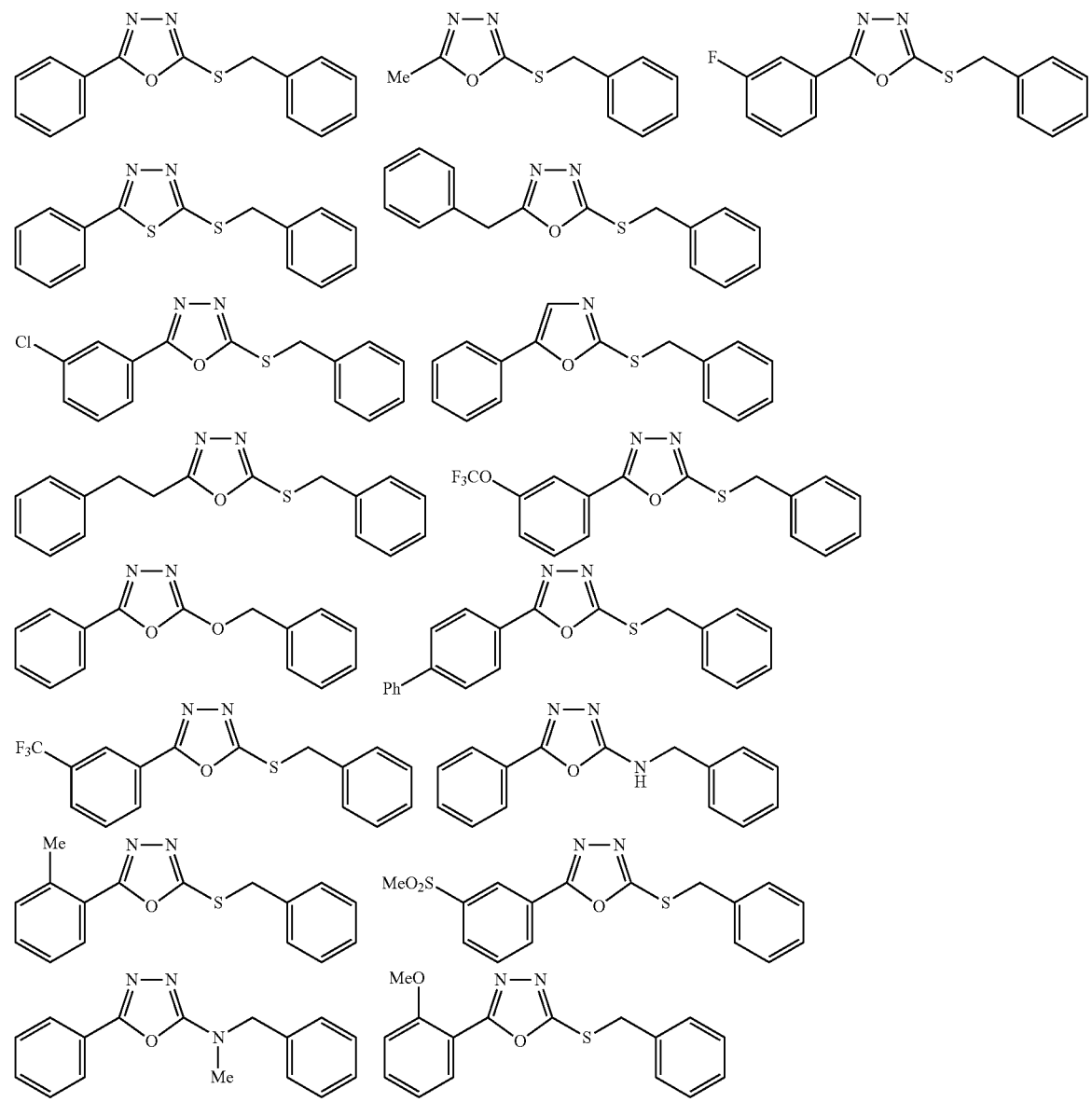

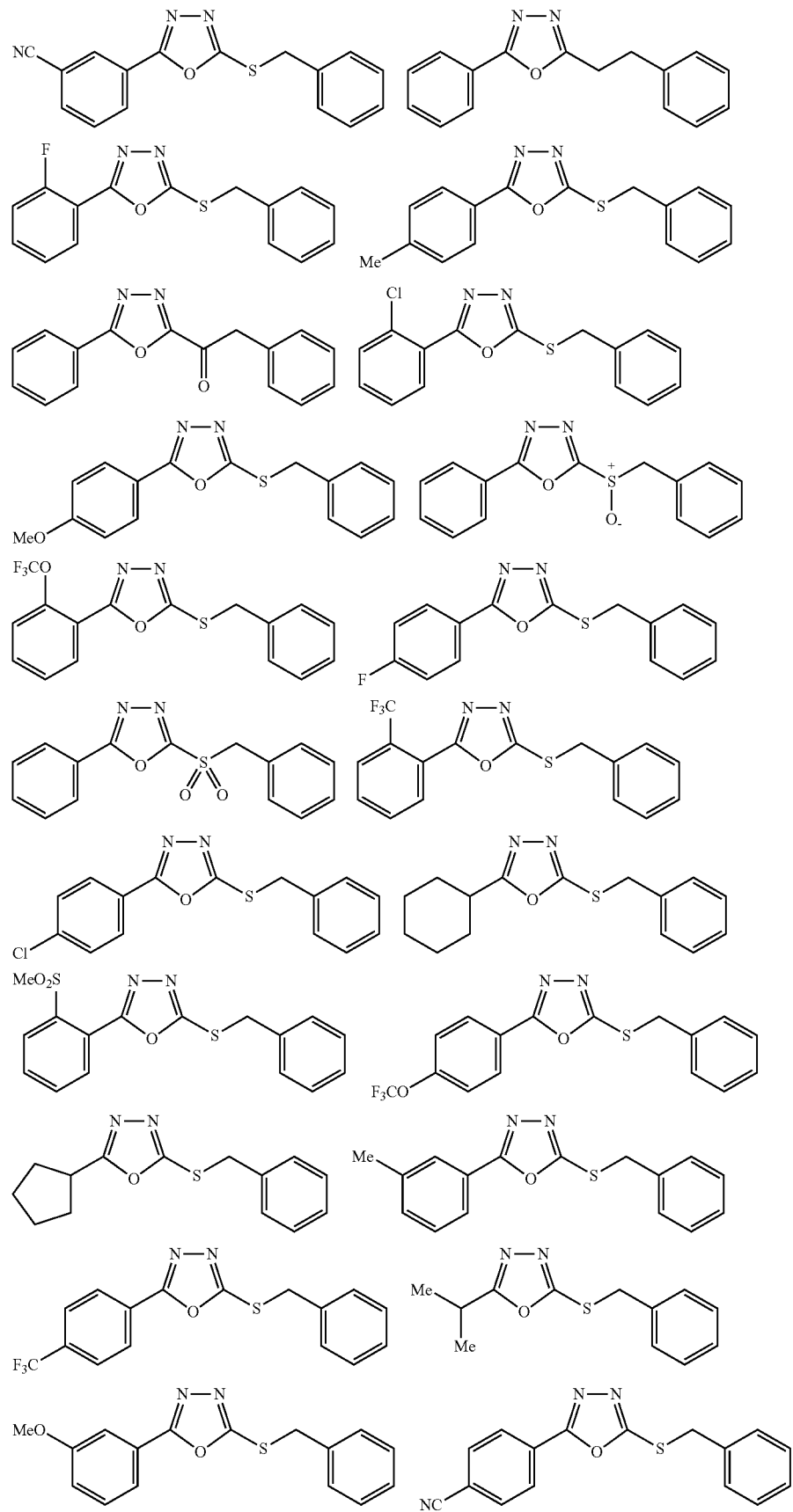

-continued
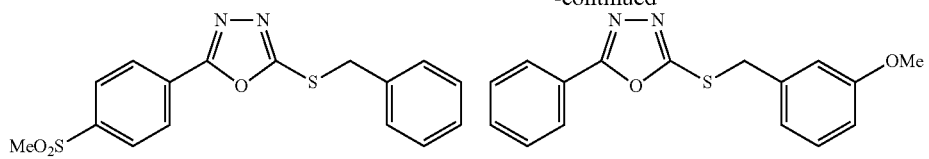
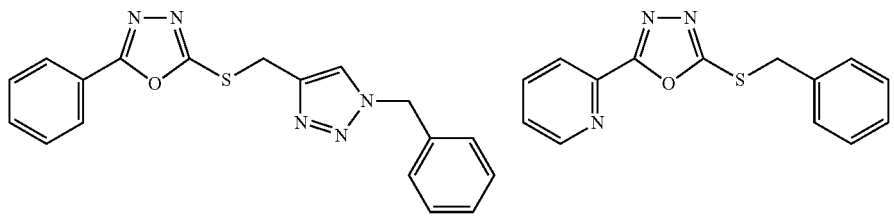
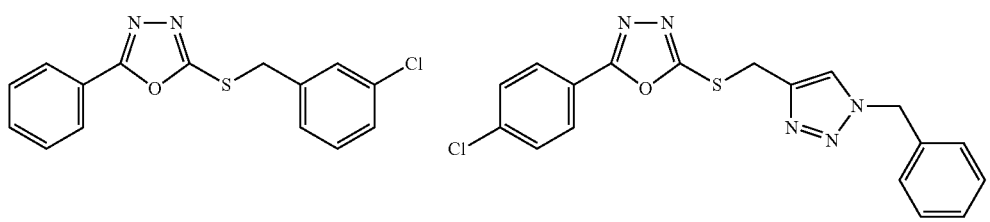
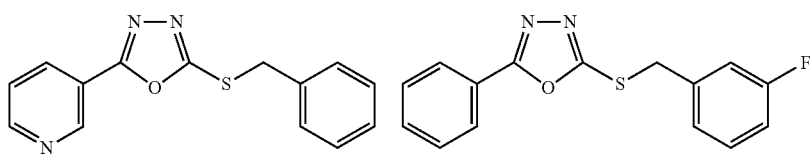
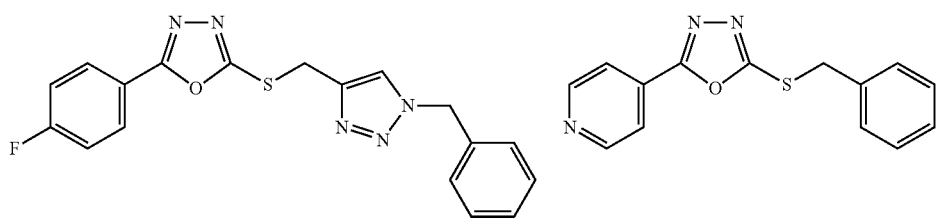
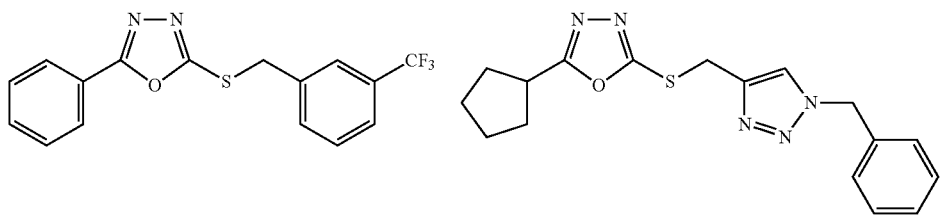
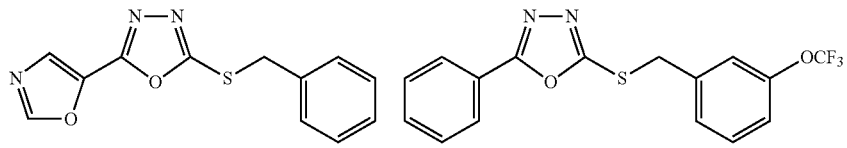
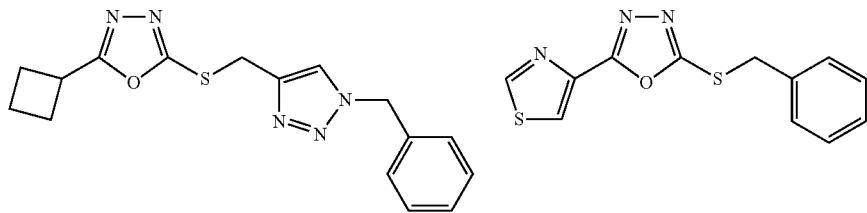

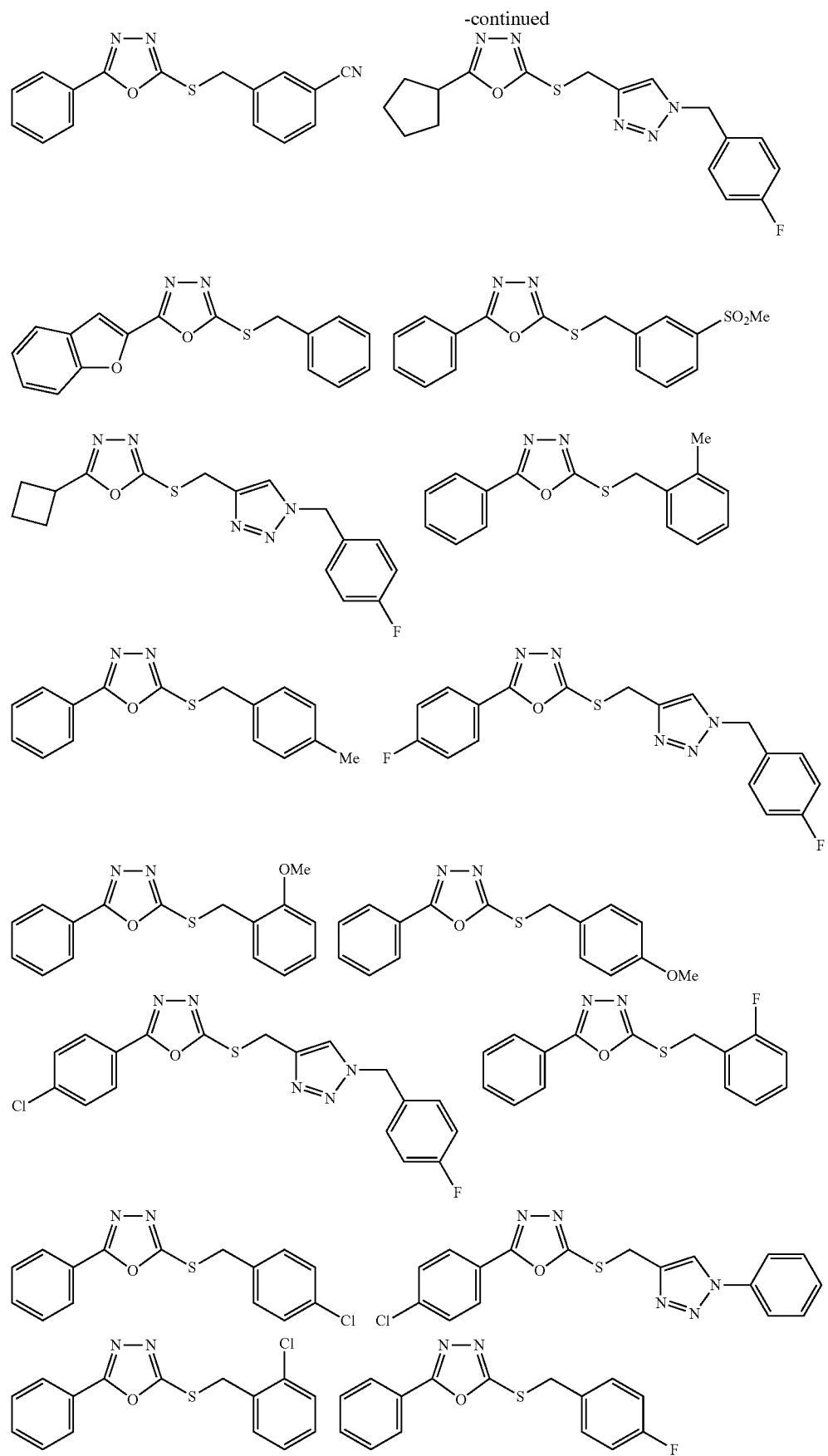

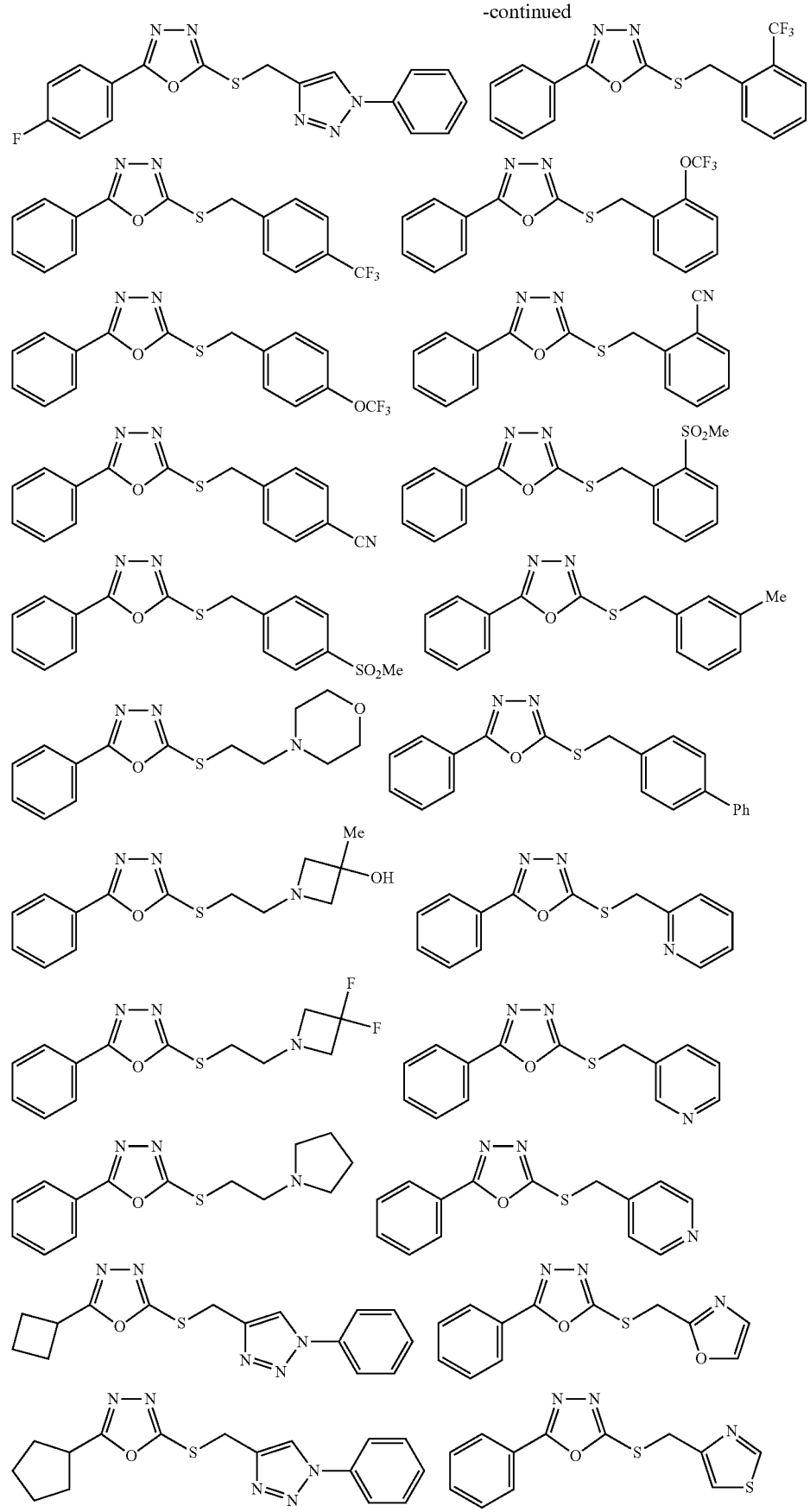

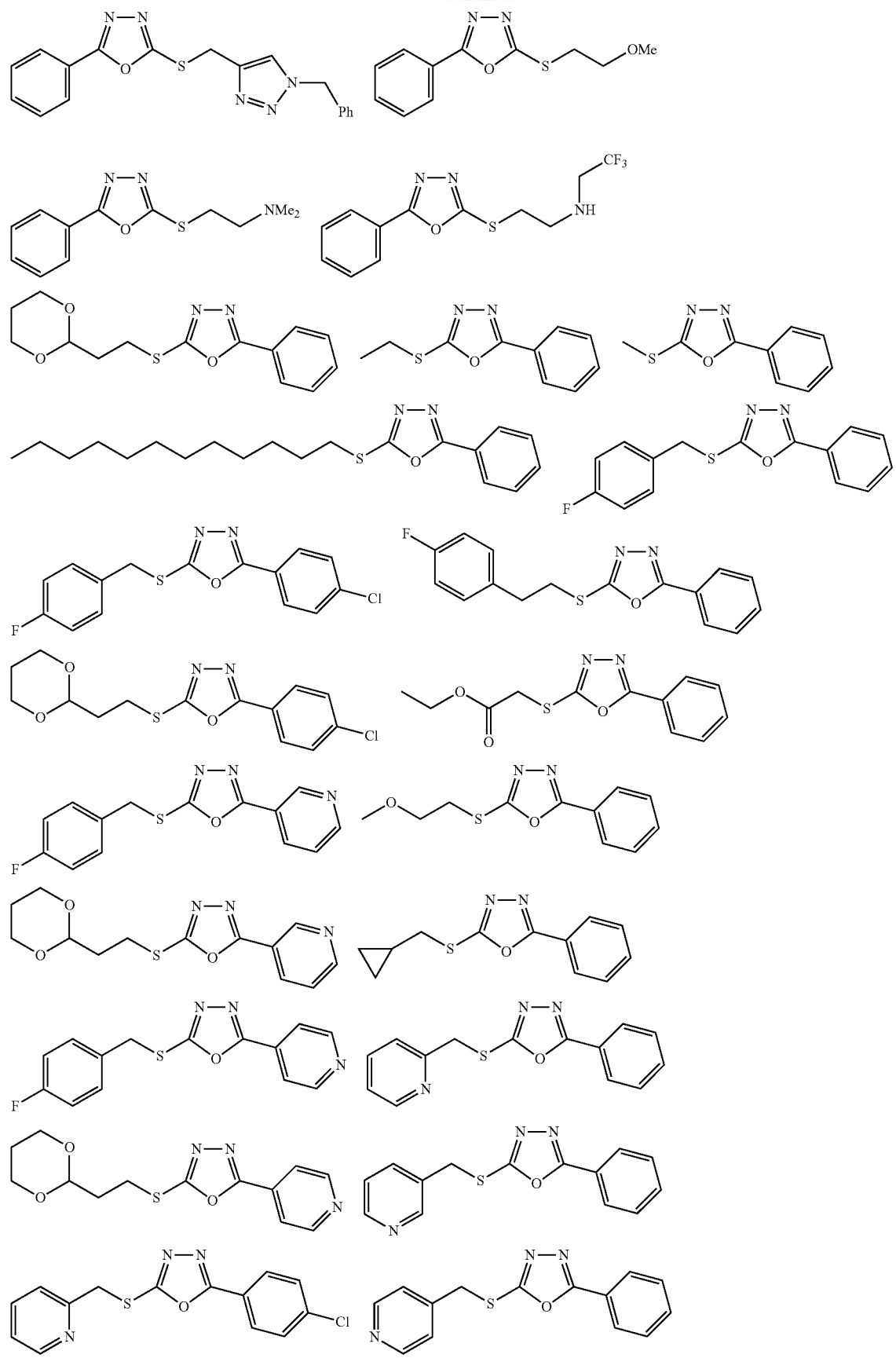

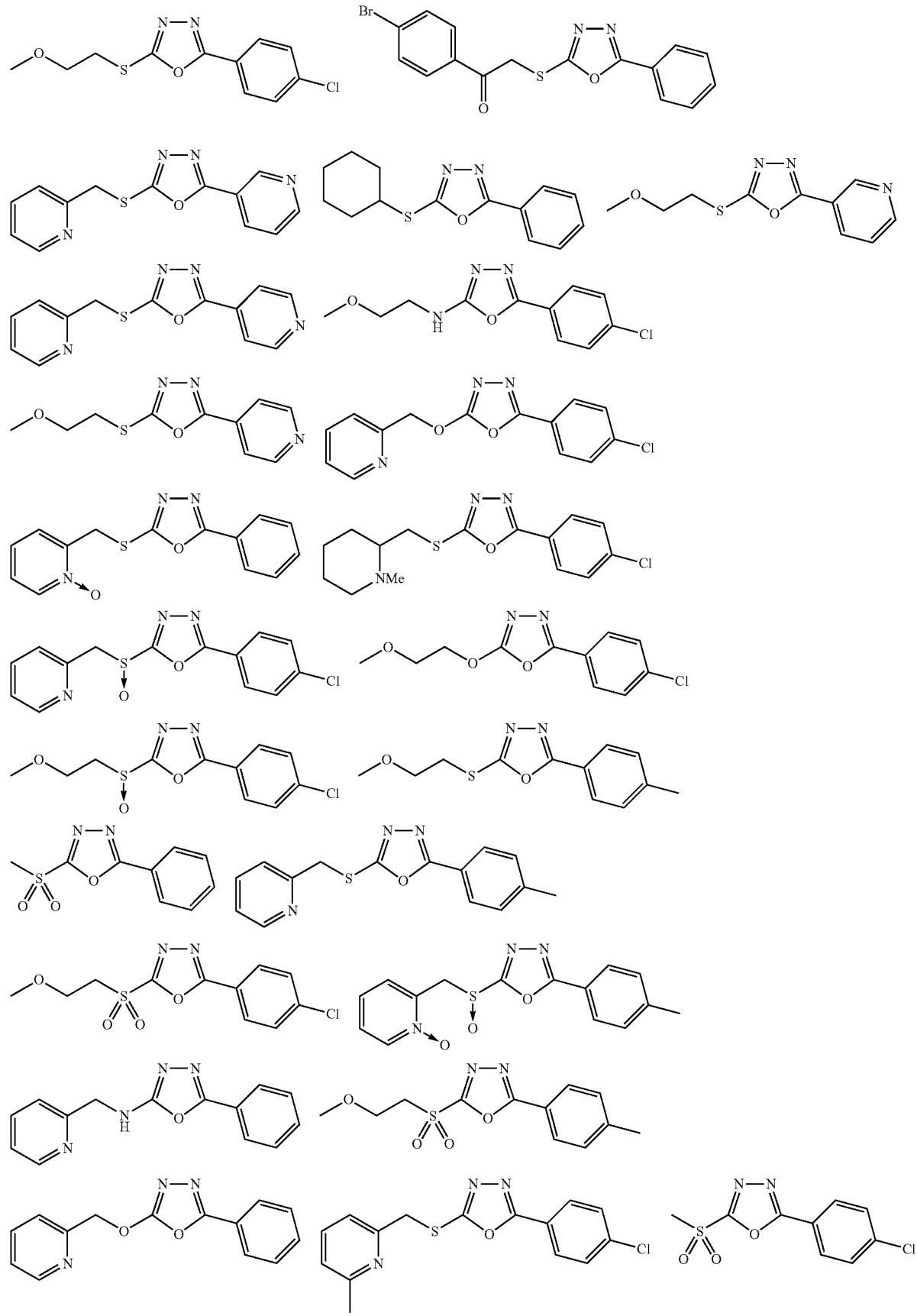

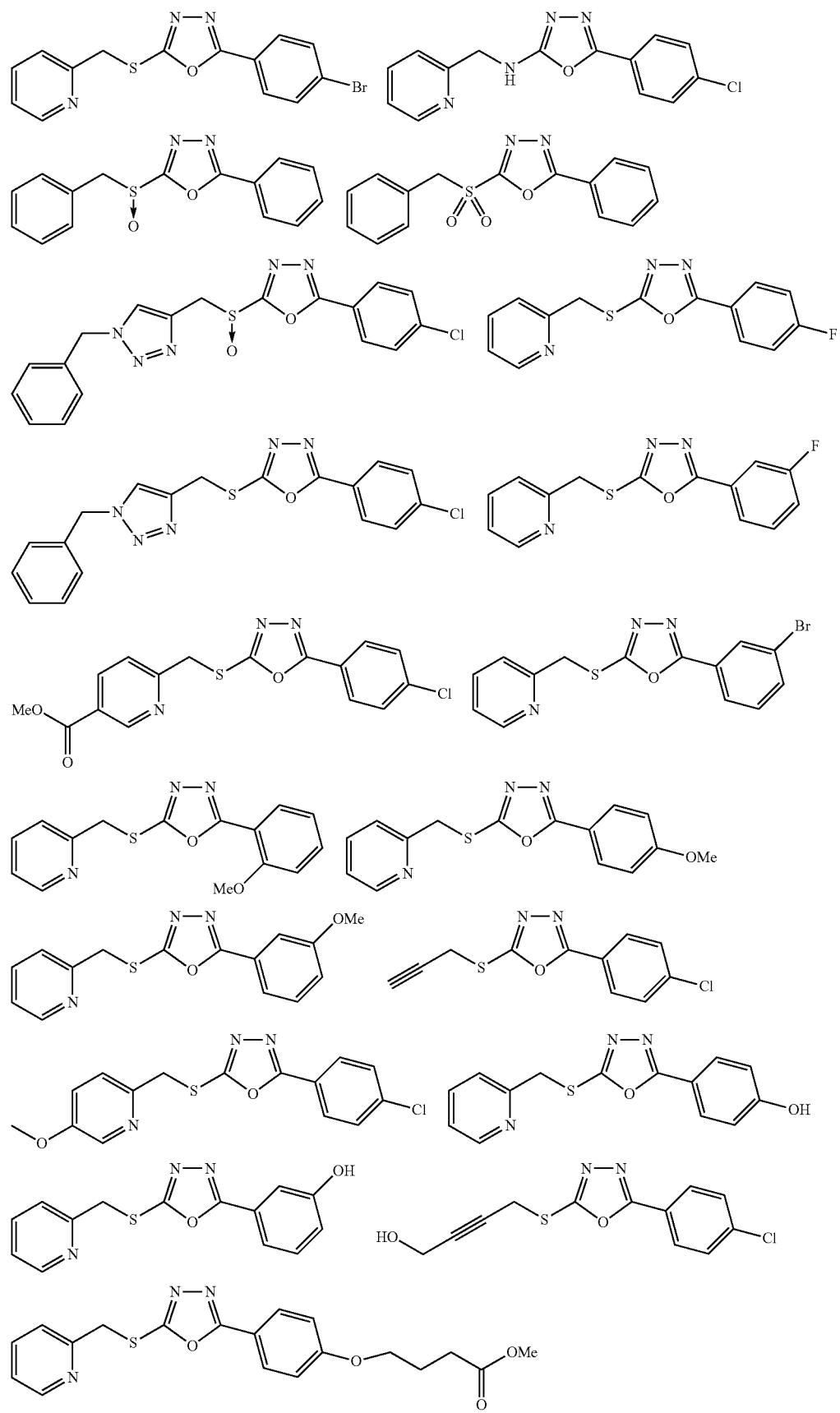

-continued
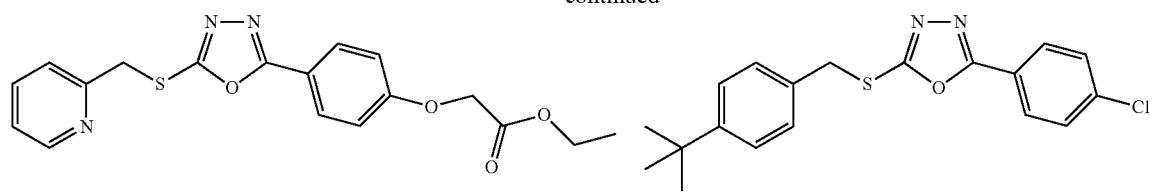
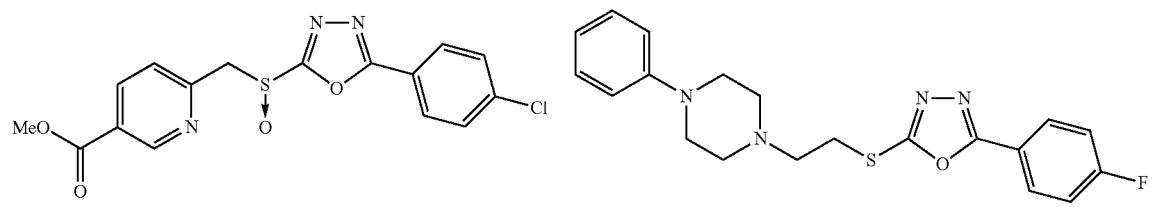
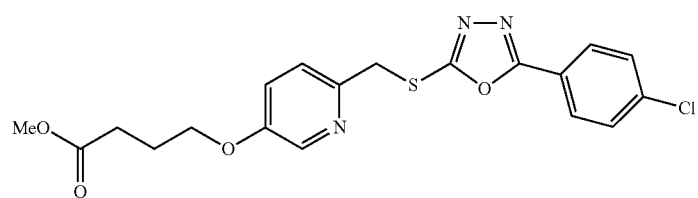
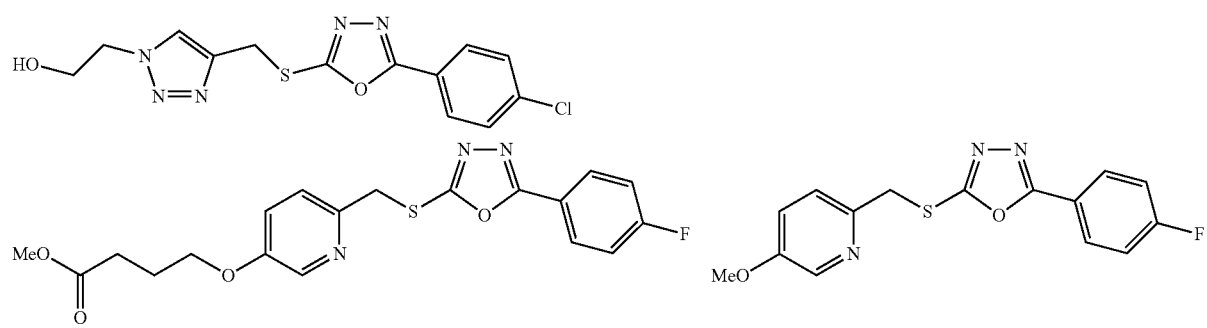
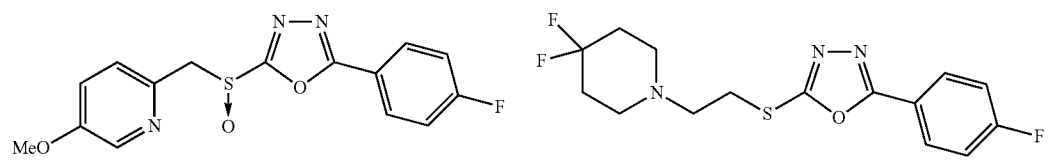
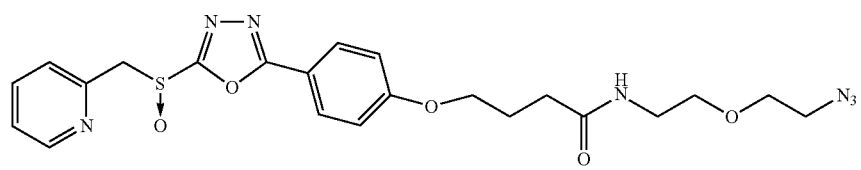
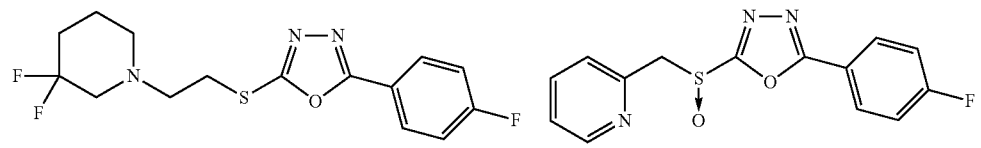
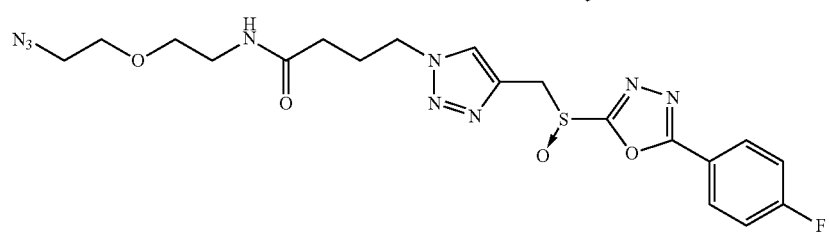

-continued
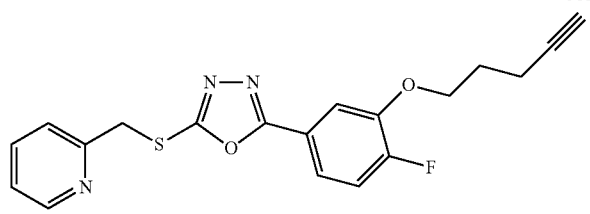
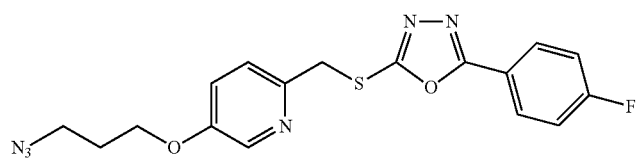
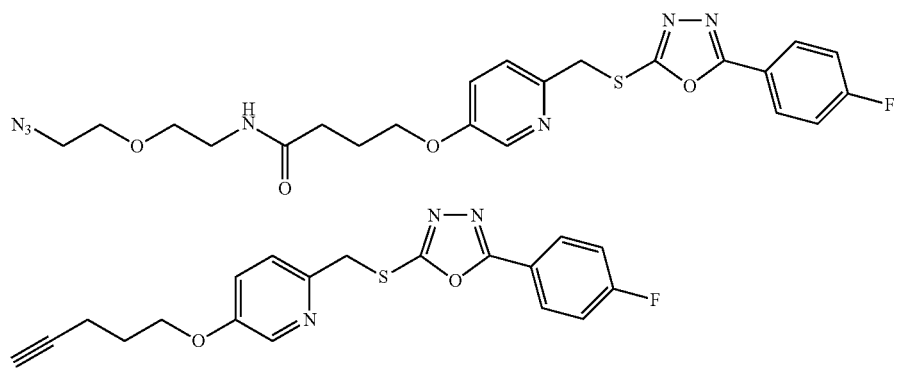
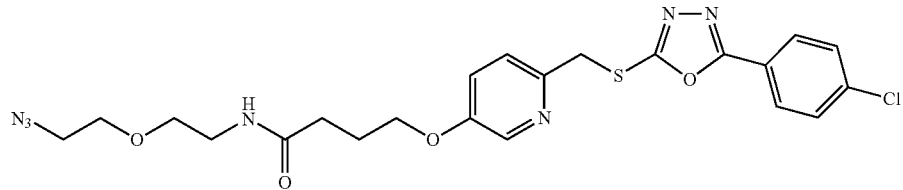
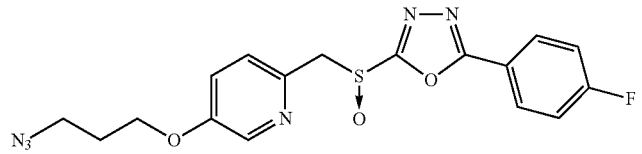
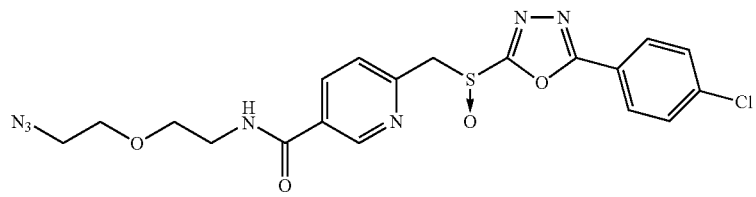
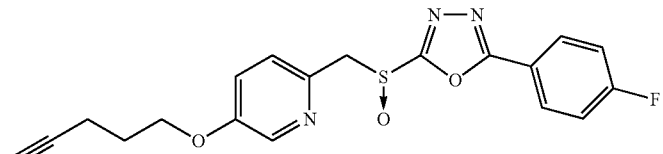
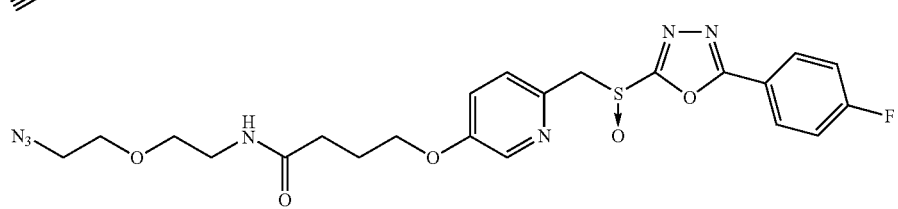

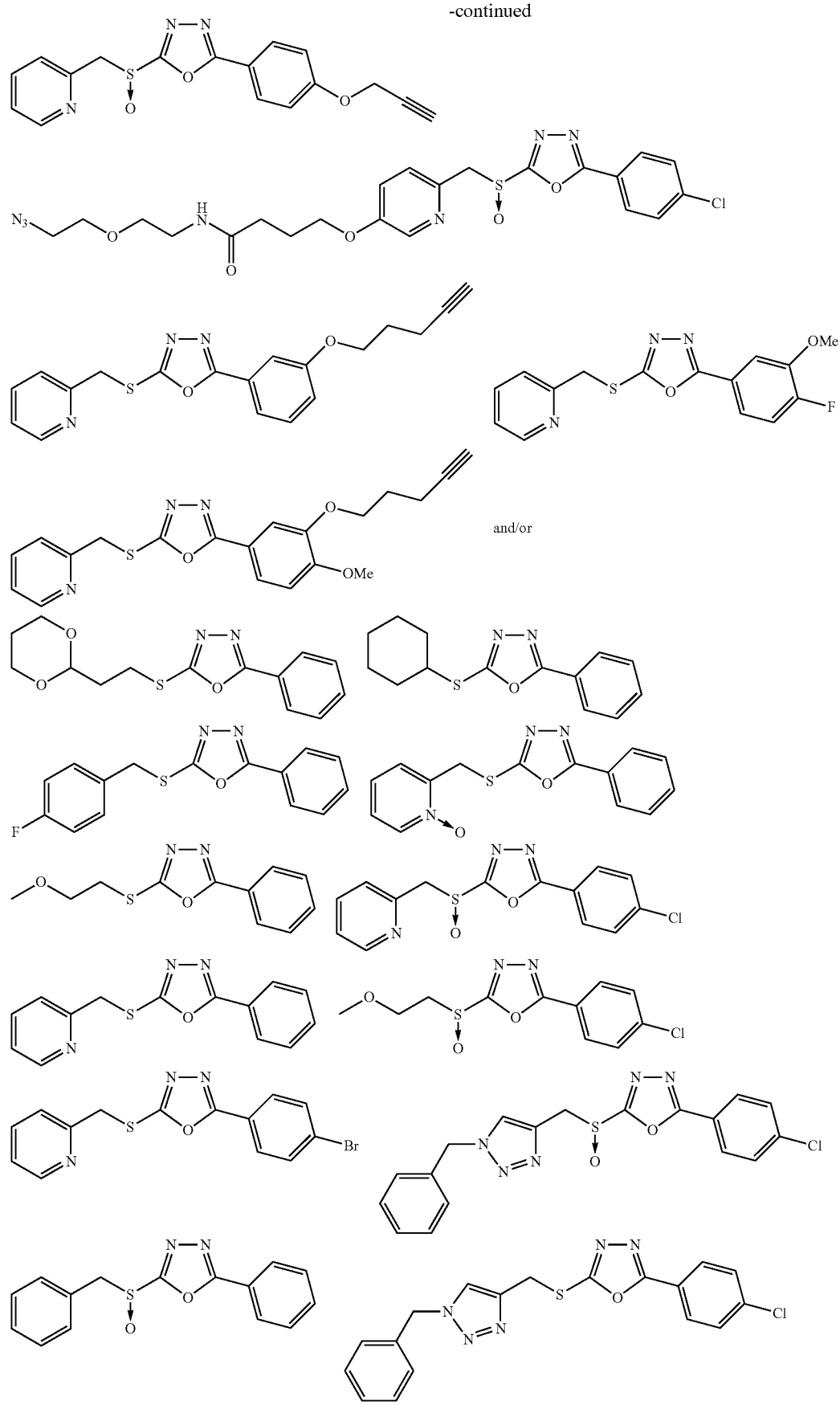
and/or

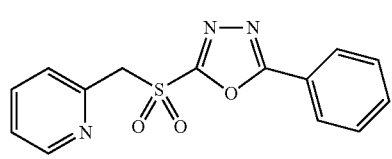
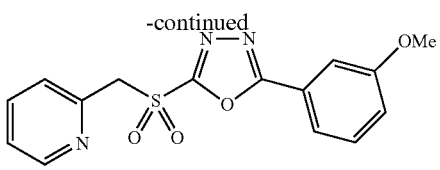
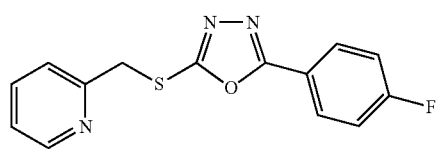
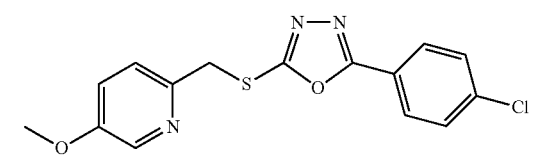
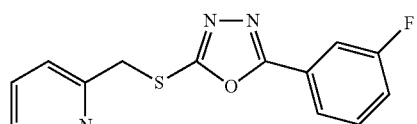
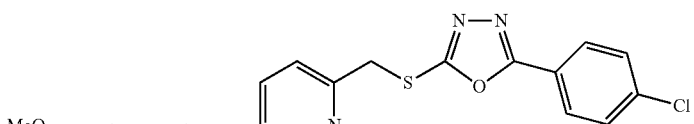
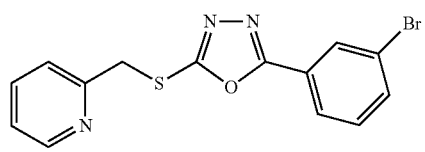
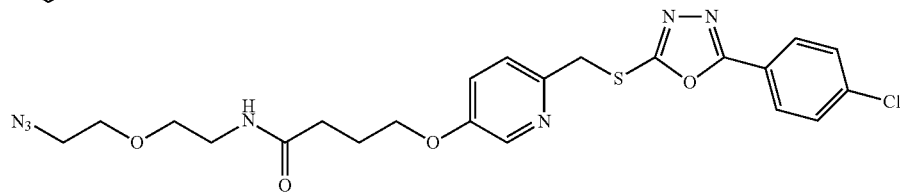
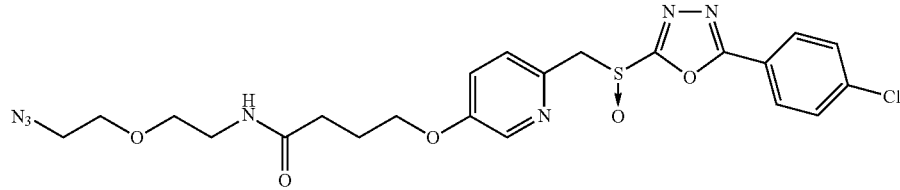
In some embodiments, a compound of Formula I, or a pharmaceutically acceptable salt, ester or prodrug thereof, is not one or more of a compound selected from the group consisting of:
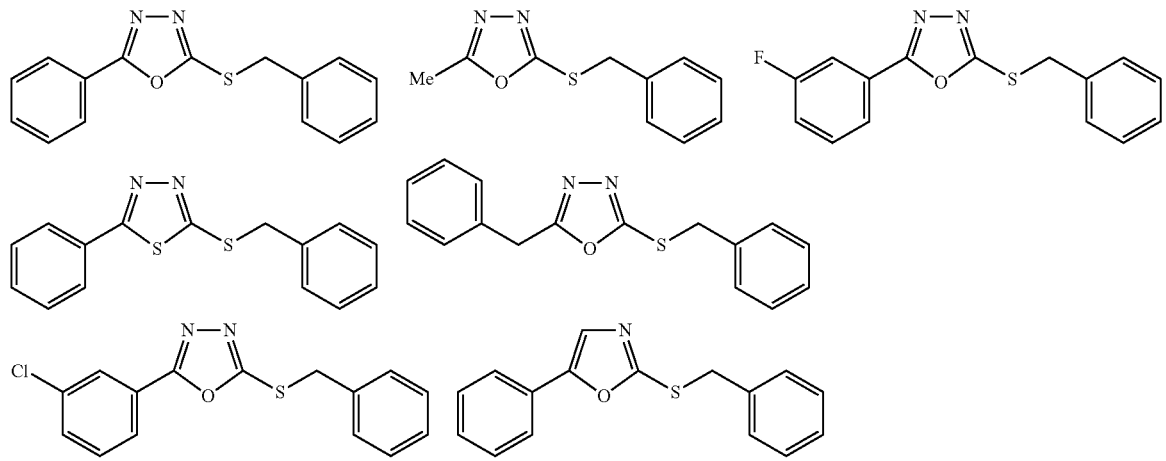

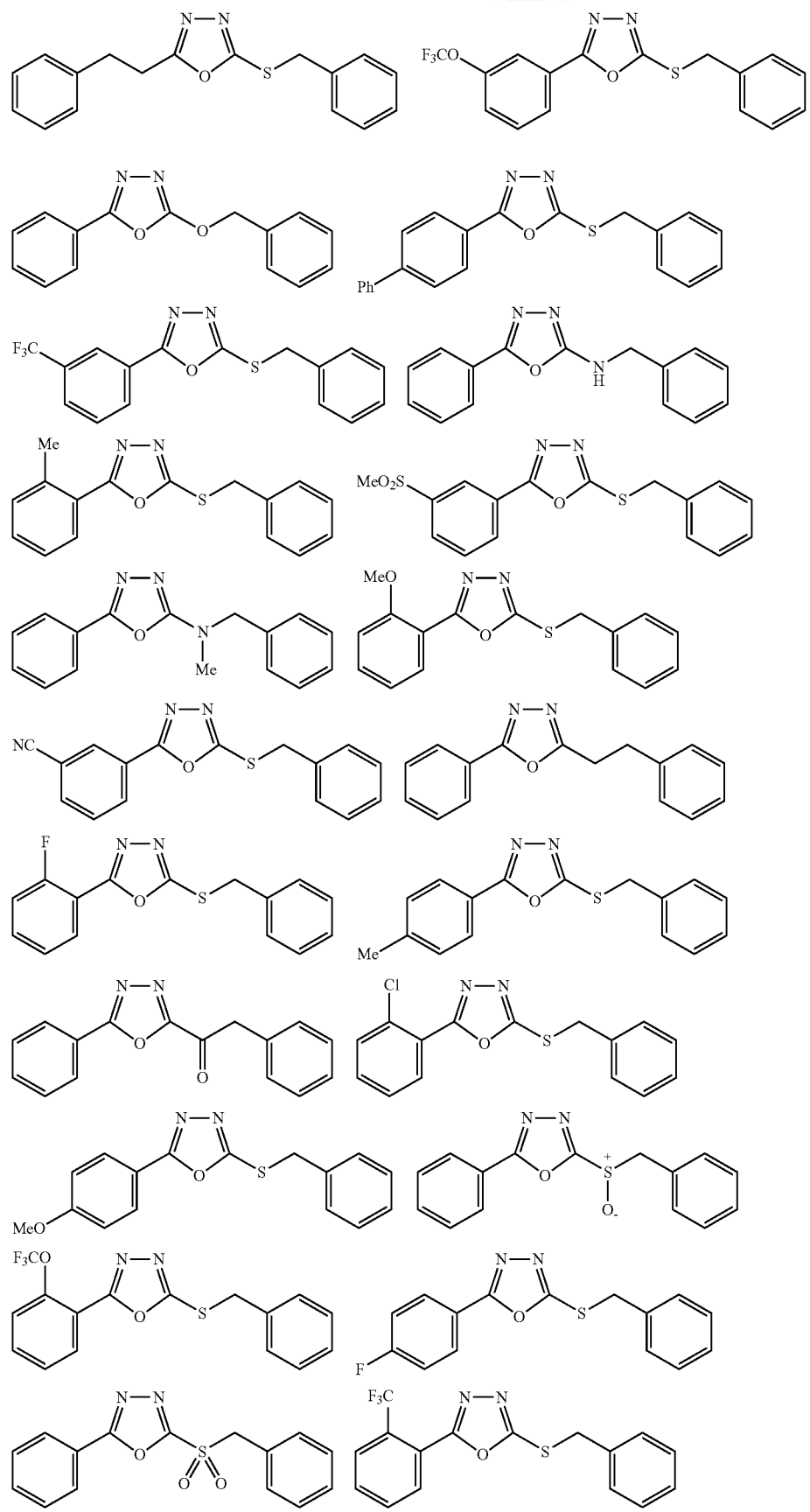

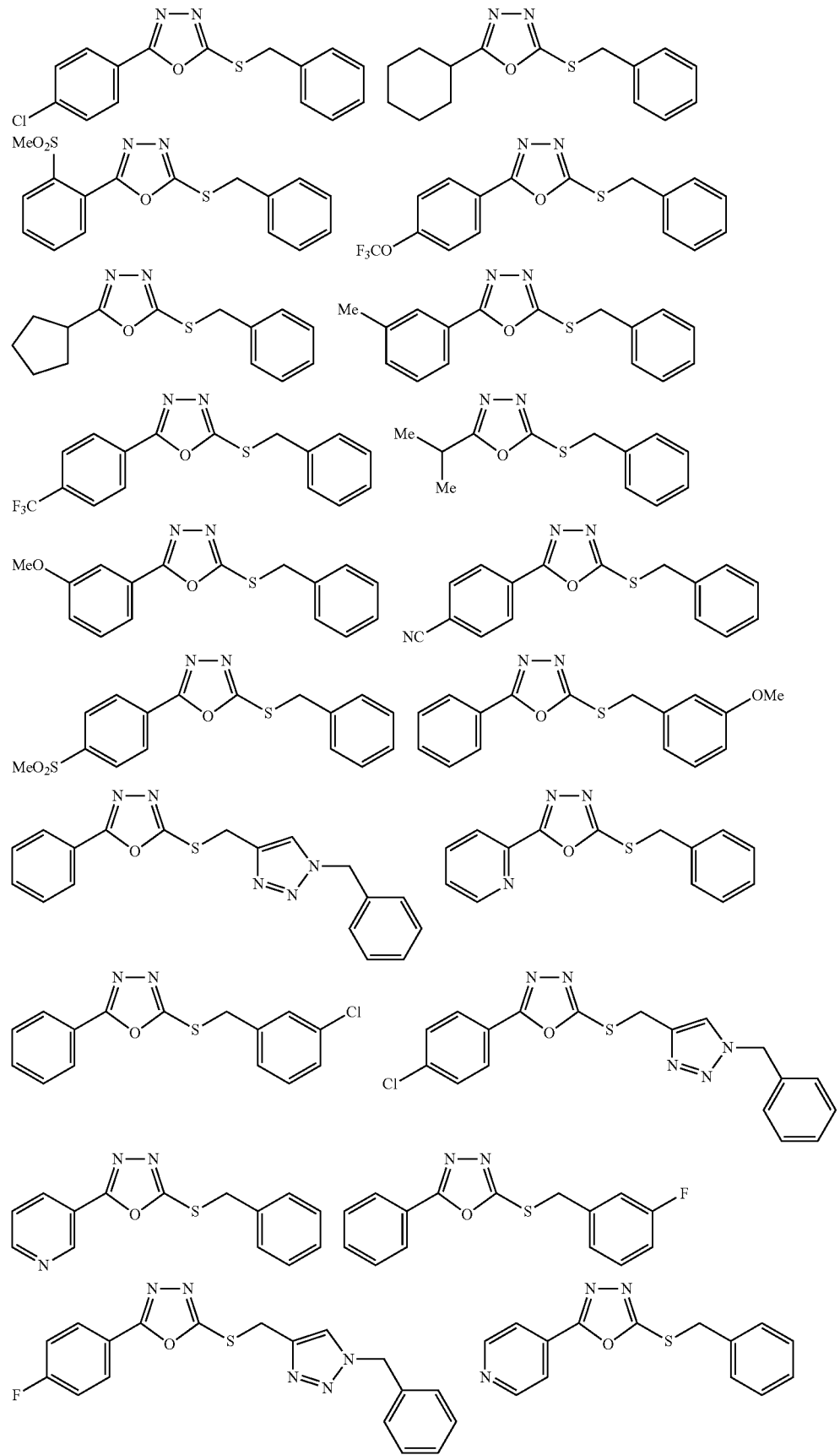

-continued
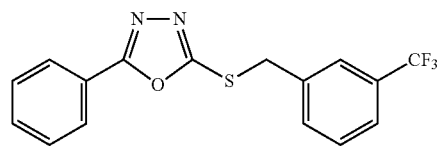
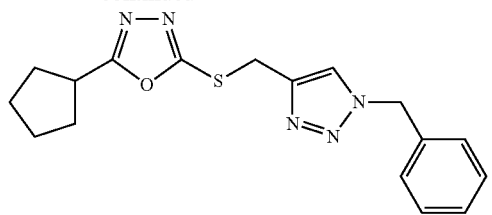
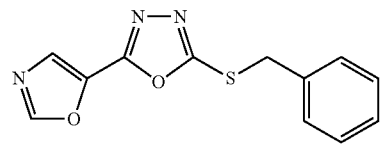
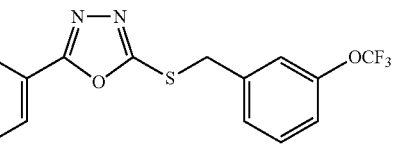
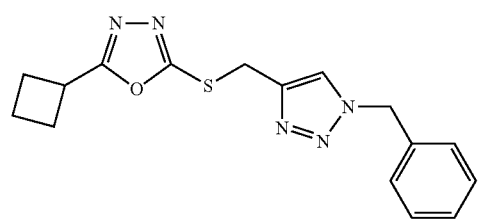
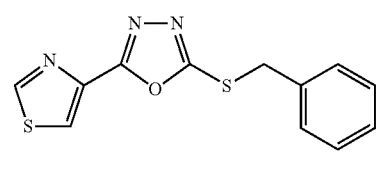
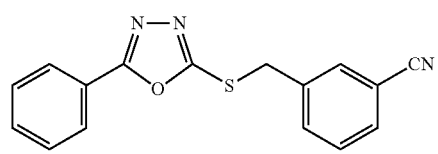
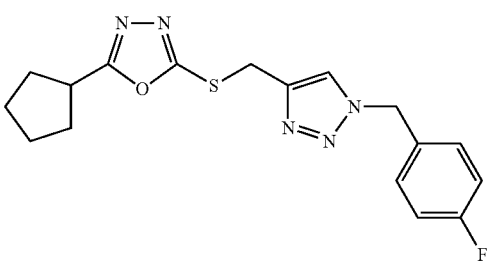
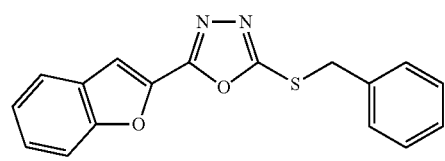
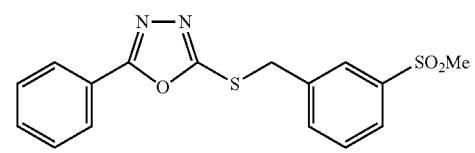
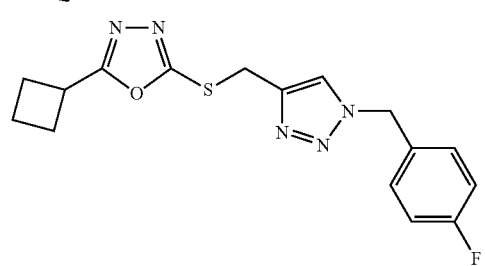
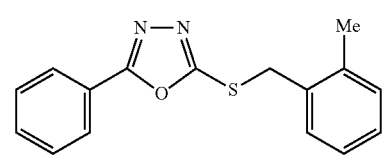
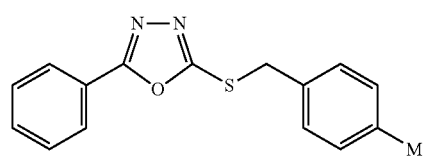
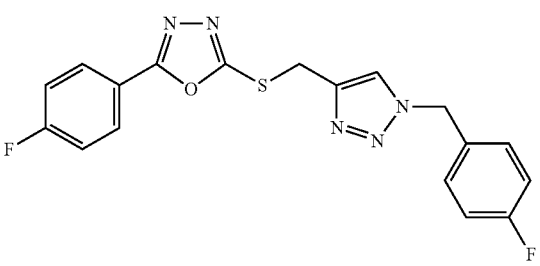
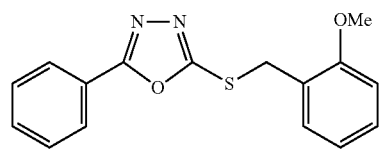
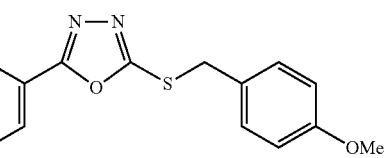

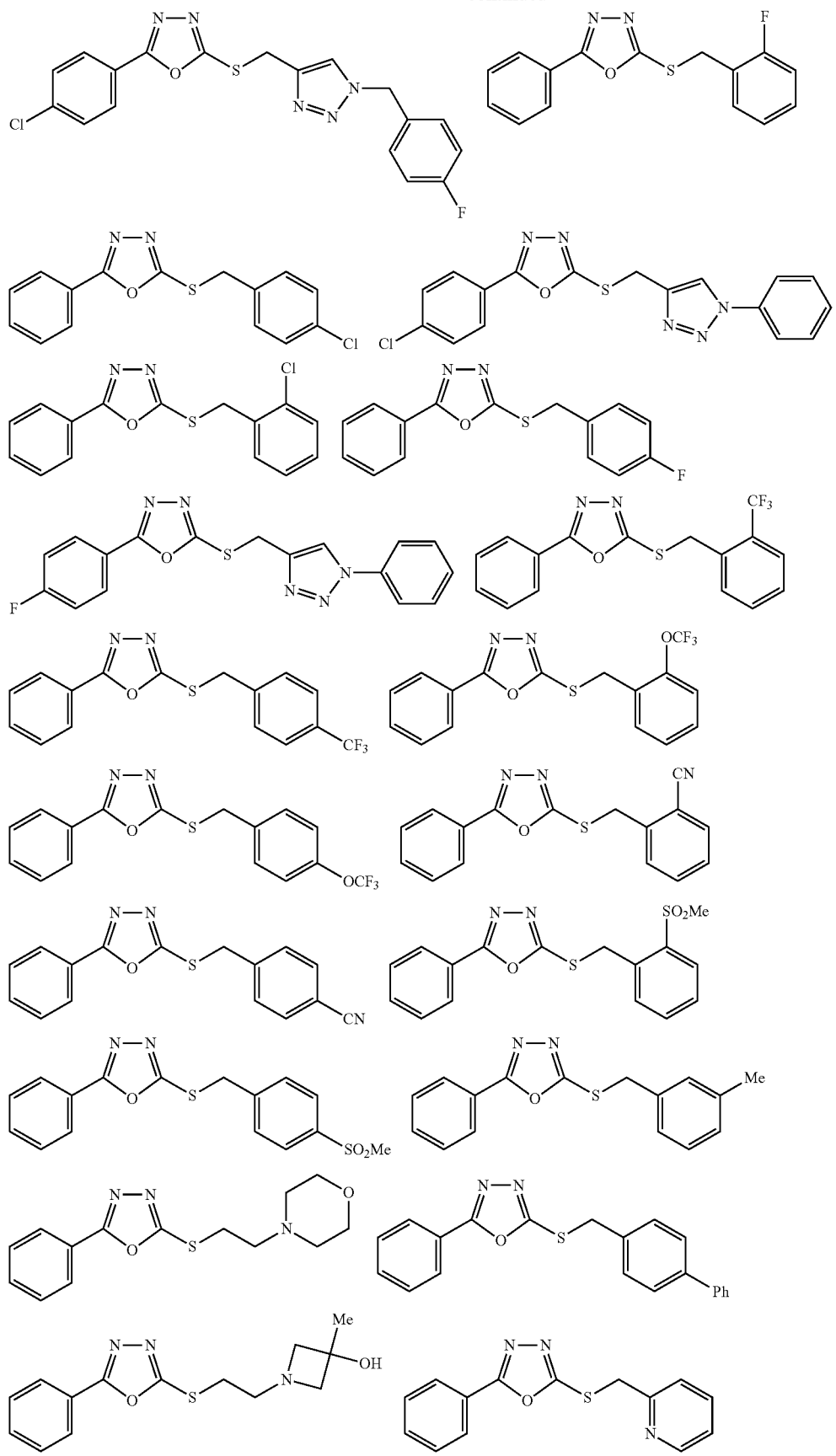

-continued
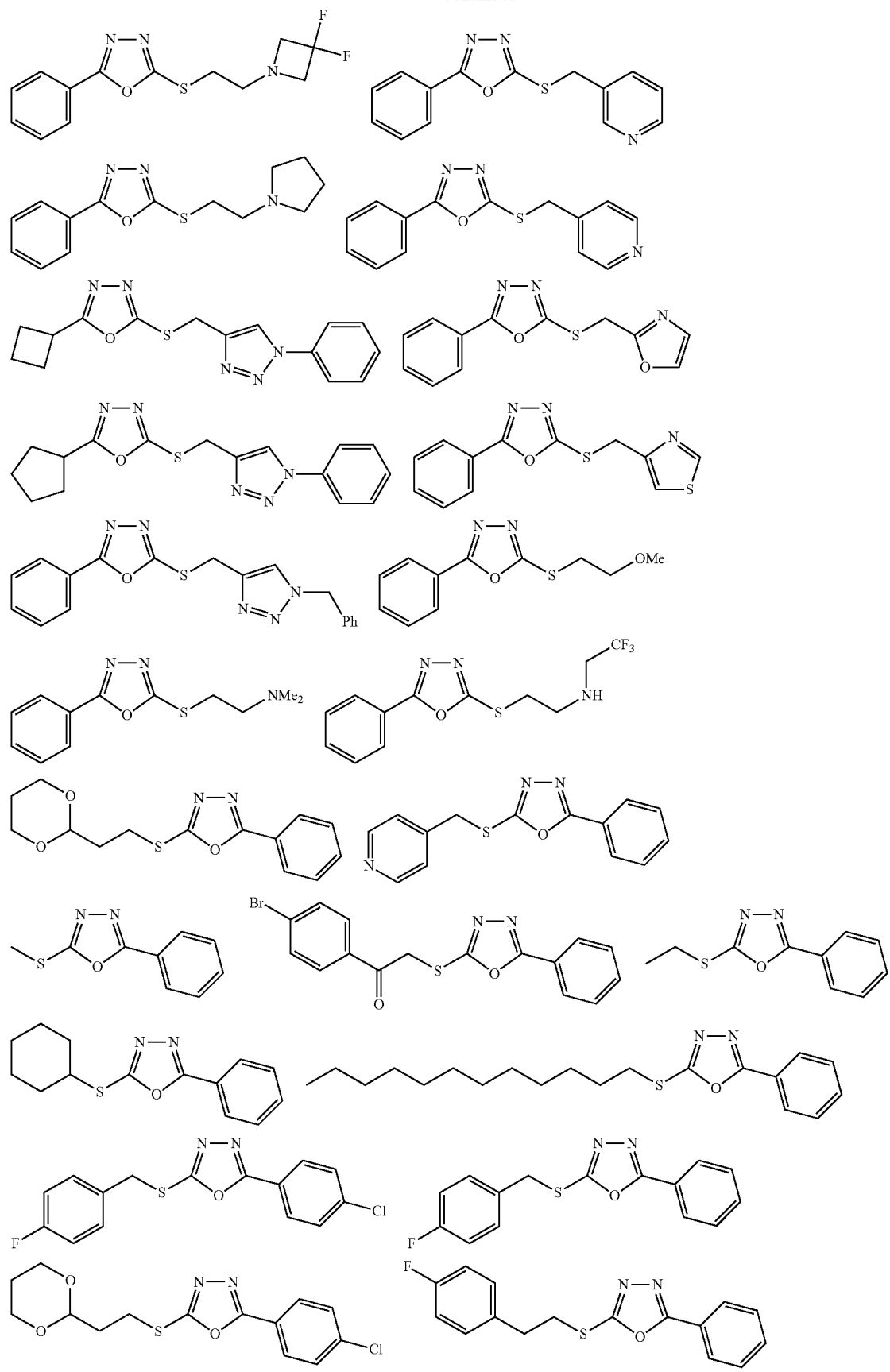

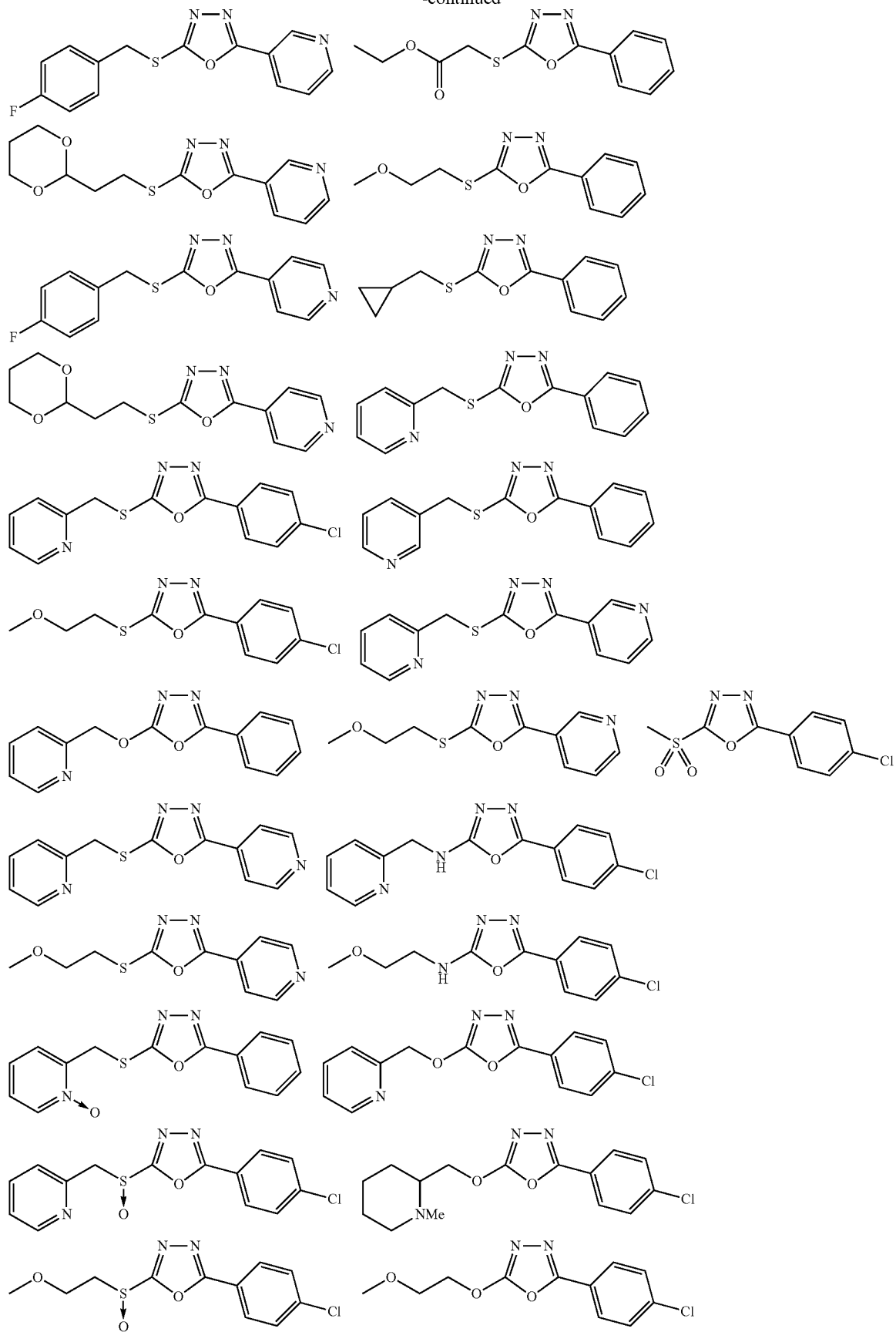

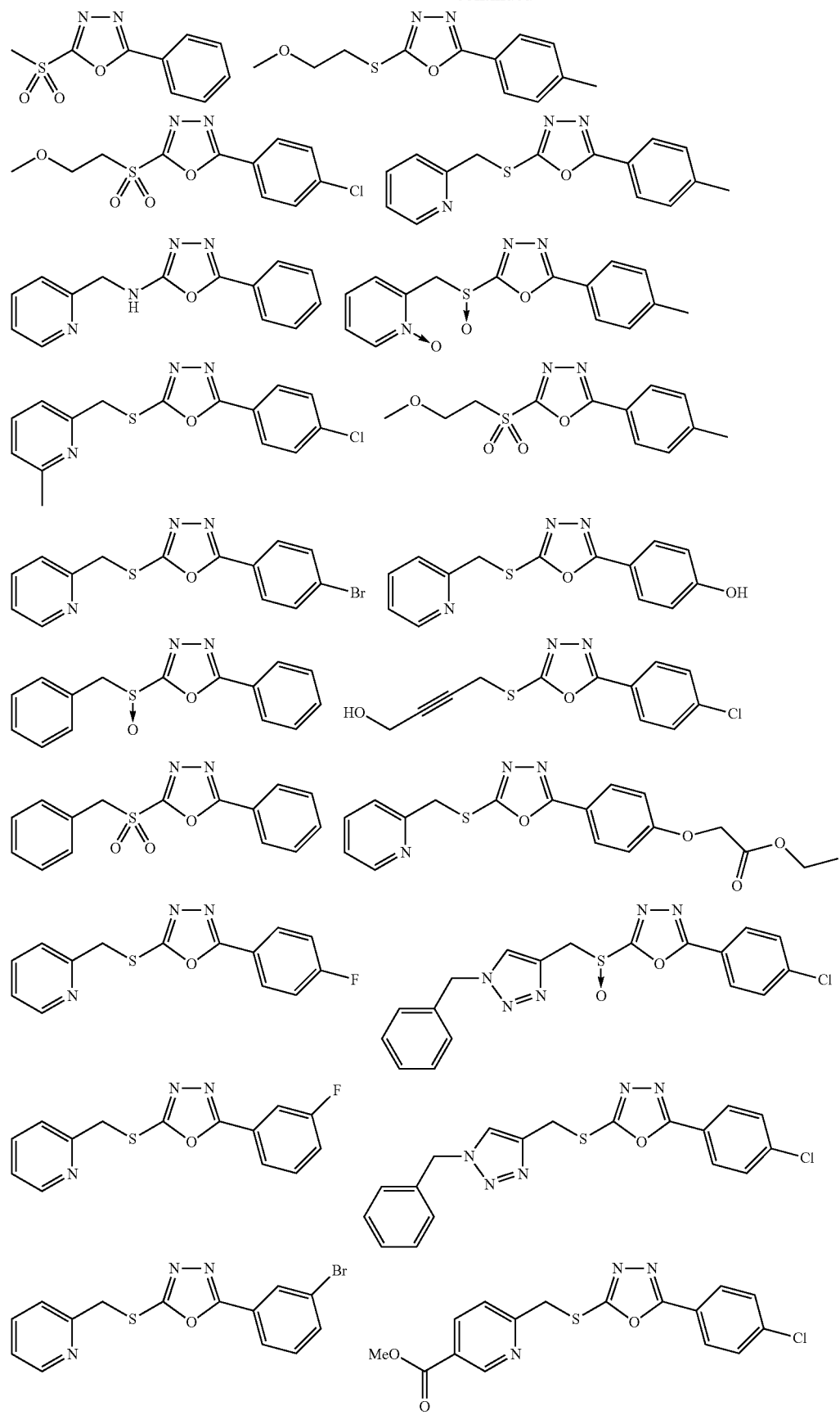

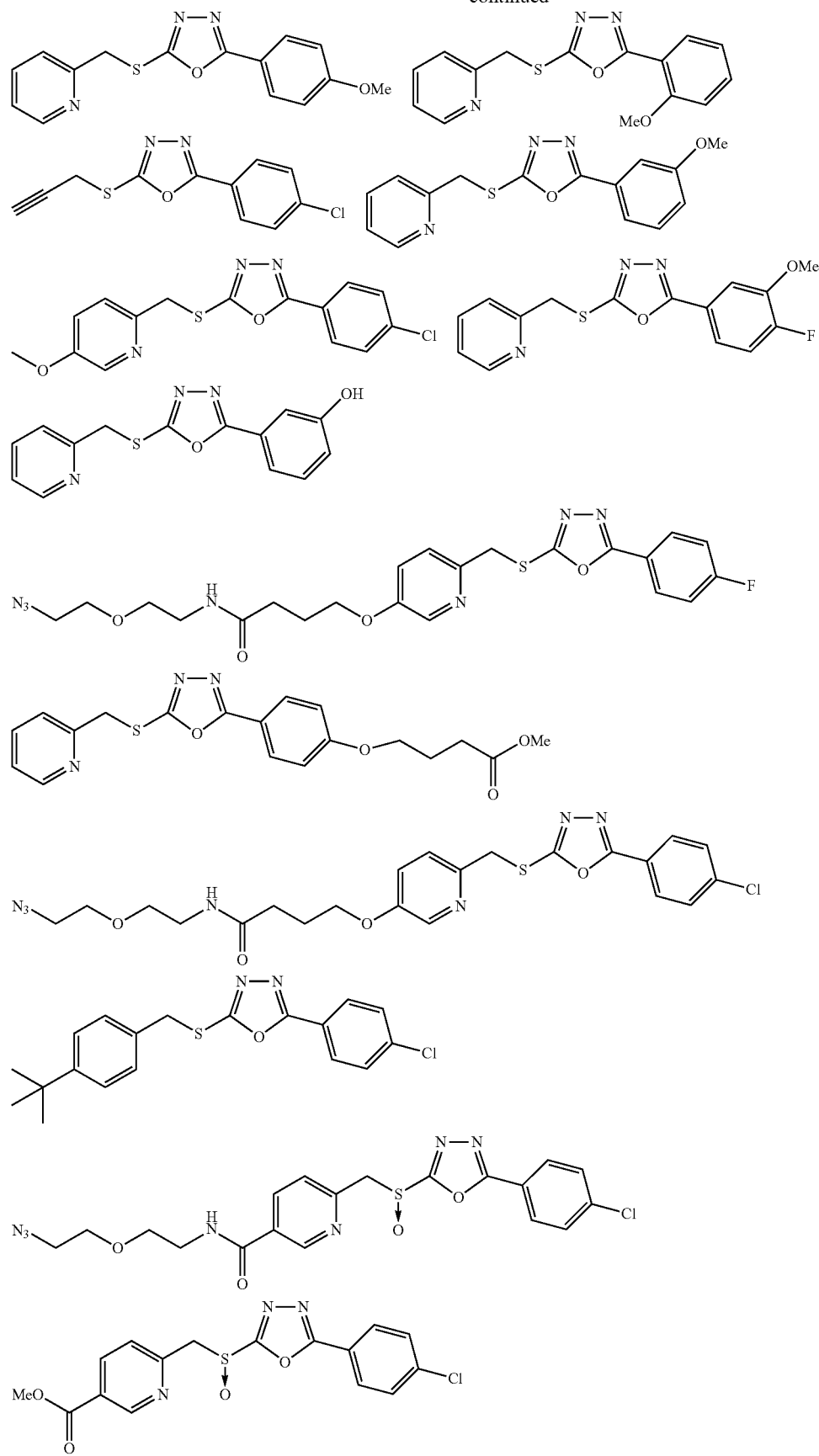
-continued

-continued
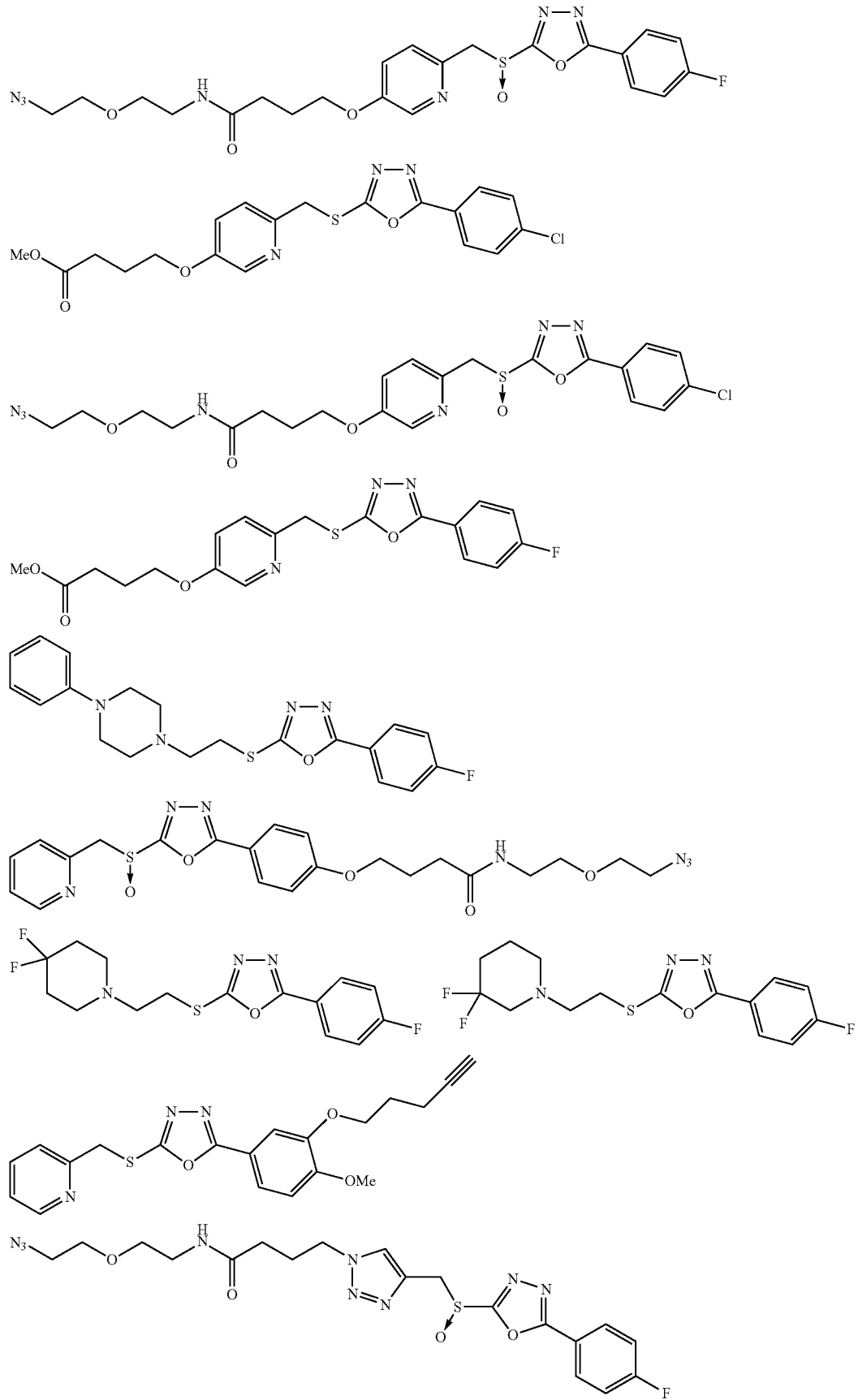

-continued
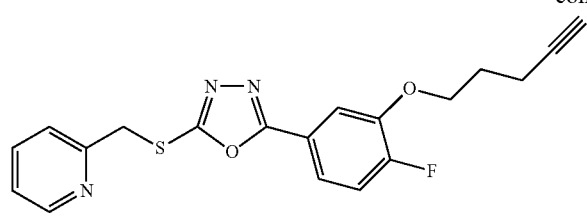
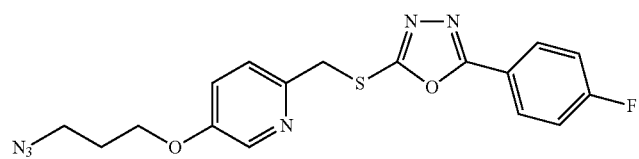
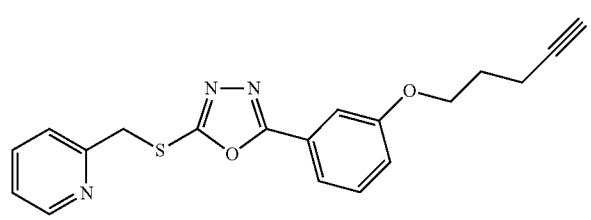
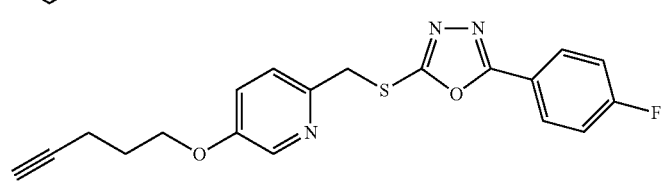
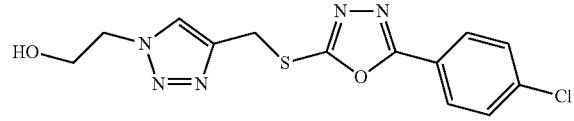
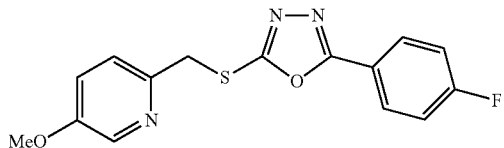
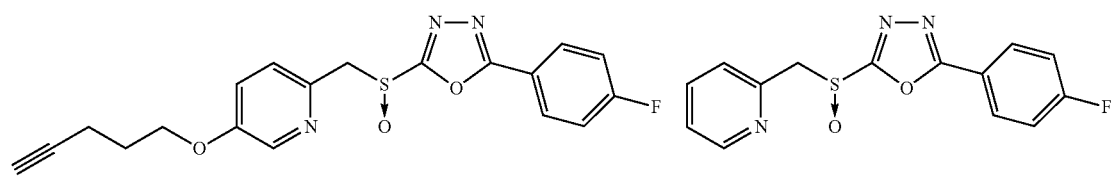
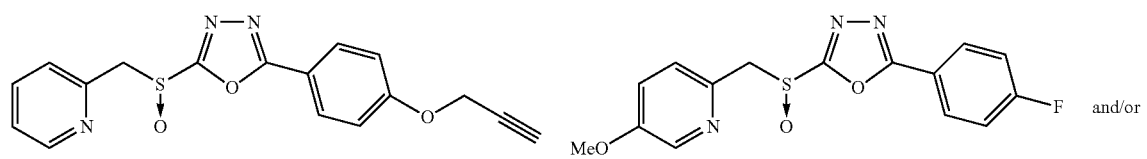
and/or
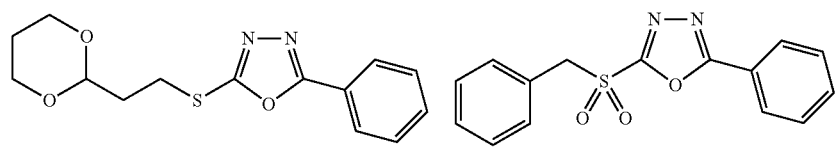
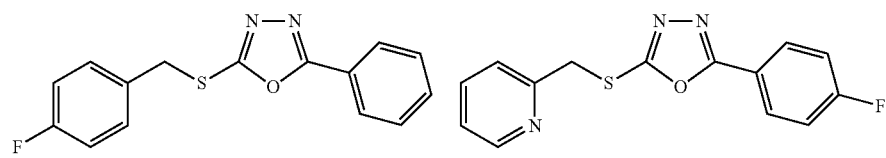

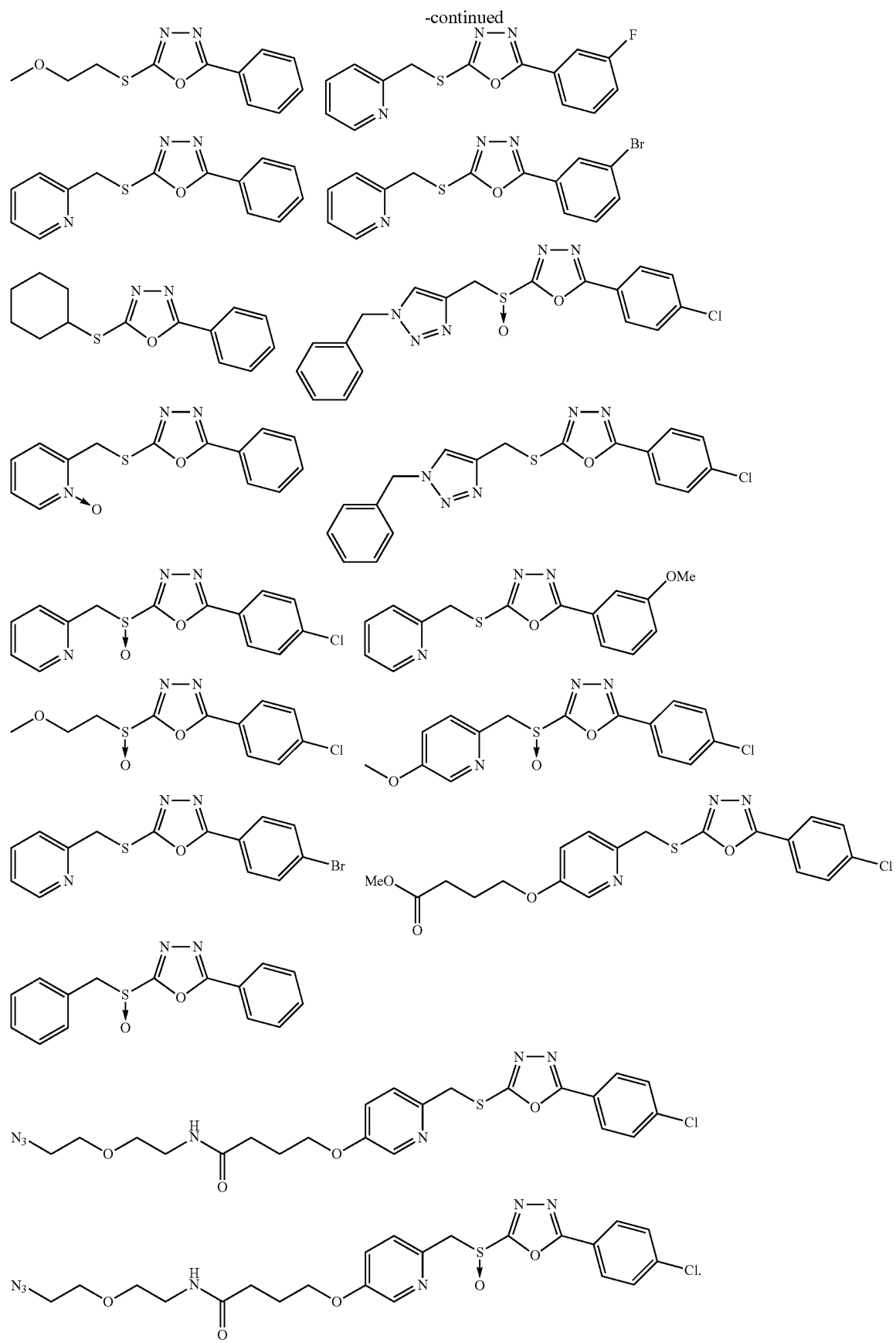
-continued

In some embodiments, the present invention provides pharmaceutical compositions comprising a compound, prodrug, or pharmaceutically salt thereof of any compound described herein.

The compounds described herein can be made by can be made according to the methods described herein and in the examples. The methods described herein can be adapted based upon the compounds desired and described herein. In some embodiments, the method is made according to the following schemes. In some embodiments, this method can be used to make one or more compounds as described herein and will be apparent to one of skill in the art which compounds can be made according to the methods described herein.

The following representative schemes illustrate how compounds described herein can be prepared. The specific solvents and reaction conditions referred to are also illustrative and are not intended to be limited. Compounds not described are either commercially available or are readily prepared by one skilled in the art using available starting materials.

The conditions and temperatures can be varied, such as shown in the examples described herein. These schemes are non-limiting synthetic schemes and the synthetic routes can be modified as would be apparent to one of skill in the art reading the present specification.

The compounds can be prepared according to any suitable method. Examples of the schemes that can be used to synthesize the compounds can be found in the Example sections. One of skill in the art would be able to modify these schemes to synthesize additional embodiments of the compounds. In some embodiments, the following scheme is used to prepare one or more compounds:

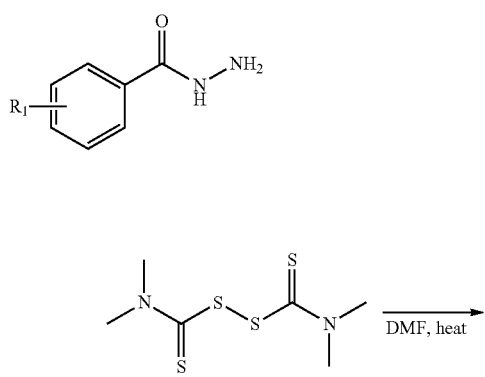

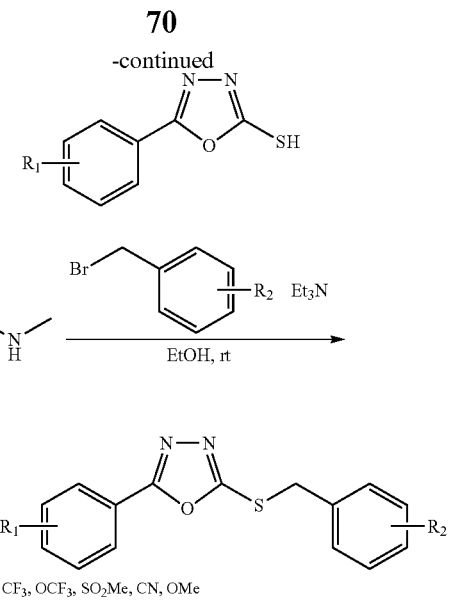

$R_1$, $R_2$ = F, Cl. Me, $CF_3$, $OCF_3$, $SO_2Me$, CN, OMe

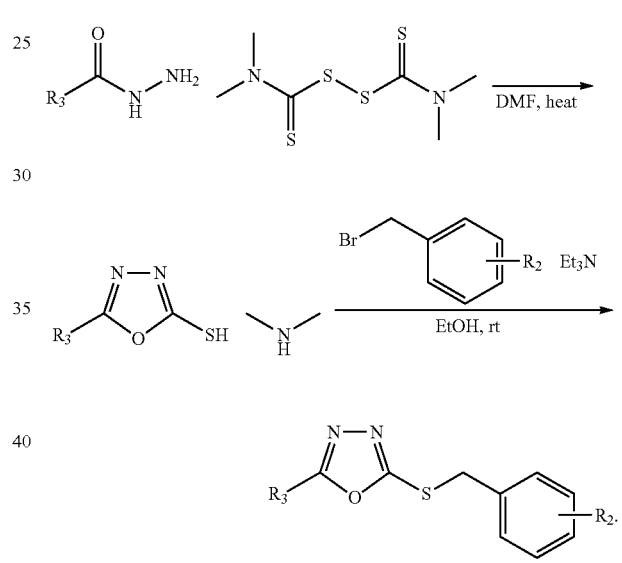

$R_3$ = alkyl. cycloalkyl, heteroaryl
$R_2$ = F, Cl. Me, $CF_3$, $OCF_3$, $SO_2Me$, CN, OMe In some embodiments, the following scheme is used to prepare one or more compounds:

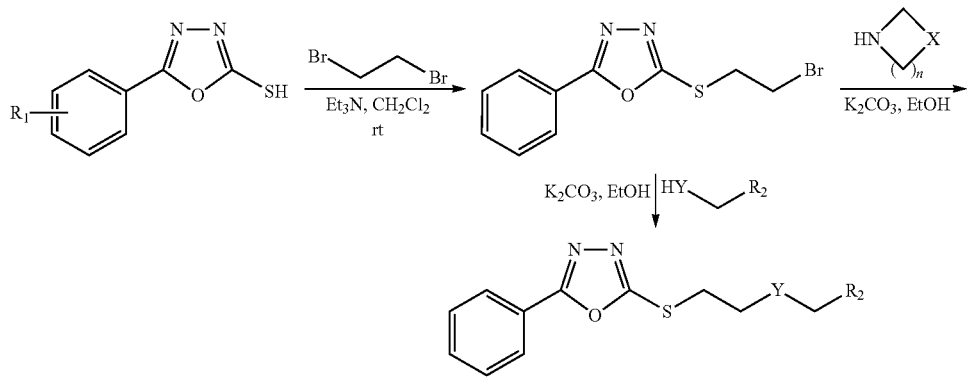

-continued

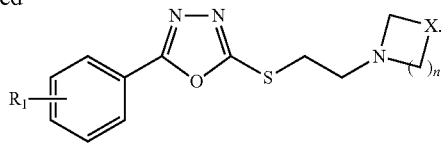

R₁ = F, Cl. Me, CF₃, OCF₃, SO₂Me, CN, OMe
R₂ = alkyl, cycloalkyl, aryl, heteroaryl
Y = O, N
n = 0, 1, 2
X = CH₂, CF₂, O, NMe, NPh The compounds can also be prepared according to the embodiments described in the Examples. The examples and schemes described herein can also be readily modified to yield other compounds described herein by modifying the substituents to produce the desired compound.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginally, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. For example, the compounds can be administered in combination with other analgesics, antidepressants, anti-anxiety compounds, anti-overactive bladder compounds, compounds for the treatment of Parkinsons, and the like. Examples of other pharmaceuticals or medicaments are known to one of skill in the art and include, but are not limited to those described herein.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In some embodiments, the compounds can be delivered in a controlled release system. In one embodiment, a pump may be used (see Langer, supra; Sefton, CRC Crit. Ref Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition of the present invention is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960,150; 3,963,025; 4,186,184; 4,303,637; 5,443,505; and 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of the anti-microbial, facially amphiphilic polymer or oligomer active agents in accordance with the present invention include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts can be included in the compositions of the invention in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

The present invention also provides pharmaceutical packs or kits comprising one or more containers filled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

The present invention also provides methods of treating tuberculosis. In some embodiments, the method comprises administering to a subject with tuberculosis or suspected of having tuberculosis a compound, or a pharmaceutically acceptable salt, ester or prodrug thereof, or pharmaceutical composition described herein, In some embodiments, the compounds are for the treatment of tuberculosis in a subject in need thereof. The treatment of tuberculosis can be targeted against replicating or non-replicating tuberculosis. In some embodiments, the compounds selectively target either replicating or non-replicating tuberculosis. Selective targeting of one form of tuberculosis over another means that the compound, or a pharmaceutically acceptable salt, ester or prodrug thereof, has at least a 2, 3, 4, 5, 6, 7, 8, 9, 10 fold preference for one form or other. Preference can be determined by comparing the $IC_{90}$ of the compound against replicating tuberculosis and the $IC_{99}$ of the compound against non-replicating tuberculosis. For example, if the compound has a 10 μm $IC_{99}$ against non-replicating tuberculosis and a 10 μm $IC_{90}$ against replicating tuberculosis the compound is said to have a 10 fold preference for non-replicating tuberculosis. The $IC_{90}$ of the compound against replicating tuberculosis and the $IC_{99}$ of the compound against non-replicating tuberculosis can be determined by any method.

For example, but not limited to, to determine the $IC_{99}$ of the compound against non-replicating tuberculosis a non-replicating, carbon-starvation assay can be used. Carbon starvation conditions can be used as a means of nutrient depriving bacilli in order to induce a non-replicating, drug tolerant state. The bacilli can be starved for 6 weeks in phosphate-buffered saline (PBS), resulting in bacteria that were refractory to standard antibiotics at doses up to 10 times the minimum inhibitory concentration (MIC). This assay is then adapted to a high throughput screen (HTS) against carbon starved TB in appropriate growth medium. An example of growth medium is, but not limited to, 7H9/tyloxapol (0.05%), which includes several cofactors (biotin, pyridoxine, iron), trace metals, and some nitrogen source (ammonium sulfate). This buffer can be used to replicate carbon starvation while still providing some minimal essential nutrients. Under these conditions are instituted, no killing will be observed with control anti-tuberculosis antibiotics, such as rifampin and isoniazid at 10×MIC (MIC: rifampin 0.01 ug/mL and INH 0.1 ug/mL). The TB can be a TB strain that has been modified to express a fluorescent protein, such as GFP. An example of such a strain is *M. tuberculosis* H37Rv strain, which expresses constitutive, episomal GFP. Fluorescence can then be used to measure cell survival. The bacteria can also be transitioned back to replicating state by the addition of 5× rich media, followed by a 4 day period of outgrowth of replicating cells. Other examples of the assay are described in the examples section herein.

The present invention also provides one or more compounds described above, or a pharmaceutically acceptable salt thereof, or a pharmaceutical composition comprising one or more compounds described above, for use in the manufacture of a medicament for the treatment of tuberculosis.

Any other known medicament, compound, or composition use for the treatment of tuberculosis can be used in co-therapy, co-administration or co-formulation with a composition or compound as described herein.

Frequency of administration is typically such that the dosing interval, for example, the period of time between one dose and the next, during waking hours is from about 2 to about 12 hours, from about 3 to about 8 hours, or from about 4 to about 6 hours. It will be understood by those of skill in the art that an appropriate dosing interval is dependent to some degree on the length of time for which the selected composition is capable of maintaining a concentration of the compound(s) in the subject and/or in the target tissue (e.g., above the $EC_{50}$ (the minimum concentration of the compound which modulates the receptor's activity by 90%)). Ideally the concentration remains above the $EC_{50}$ for at least 100% of the dosing interval. Where this is not achievable it is desired that the concentration should remain above the $EC_{50}$ for at least about 60% of the dosing interval, or should remain above the $EC_{50}$ for at least about 40% of the dosing interval.

In order that the embodiments disclosed herein may be more efficiently understood, examples are provided below. It should be understood that these examples are for illustrative purposes only and are not to be construed as limiting in any manner.

EXAMPLES

Assays used to measure growth or inhibition of TB.
Bacterial Strains and Growth Conditions.
The strain *M. tuberculosis* H37Rv was used for all experiments. GFP was expressed using a constitutive episomal plasmid driven by the Rv3583c promoter. An inducible firefly luciferase expression plasmid was constructed using an anhydrotetracycline inducible system, as described previously (30). Mtb H37Rv was grown at 37° C. in Middlebrook 7H9 broth supplemented with 10% OADC (oleic acid-albumin-dextrose complex), 0.2% glycerol and 0.05% Tween-80 or on Middlebrook 7H10 plates supplemented with 10% OADC enrichment.

Carbon Starvation.
Freezer stocks of H37Rv were diluted 1:50 in fresh 7H9 OADC media and cultured until late log phase, $OD_{600}$ between 0.6 and 1.0. The bacteria were centrifuged at 2800×g for five minutes and resuspended in 50 mL of starvation media (7H9 and 0.05% Tyloxapol without any supplementation). The cells were then washed an additional two times with starvation media. After the final wash the cells were resuspended in starvation media to an $OD_{600}$ of 0.2 and 50 mL of culture aliquoted into a sterile roller bottle. The starvation culture was incubated standing at 37° C. for 5 weeks.

Compound Testing: An initial assay was developed and utilized using a GFP-expressing *M. tuberculosis* reporter strain that measured fluorescence as a marker for growth and survival after an outgrowth period in rich 7H9 media. This assay was modified to accommodate the scale of the screen involving the MLPCN library. These modifications include using Alamar blue to measure surviving bacteria rather than the fluorescence, and outgrowth in 7H12 media.

Carbon starvation assays. For *M. tuberculosis* starvation screening assays, carbon-starved bacteria expressing GFP were diluted and plated into 384 well plates into which compounds had previously been pinned for a final OD600 of 0.05, a final volumes of 40 µL and a final compound concentration of 30 µM. Plates were incubated for a period of 120 h, at which time 10 µL 5× concentrated media was added to each well of the plate (7H9 media with 50% OADC, 1% glycerol, 0.05% tyloxapol). Plates were then incubated for an additional 96 hours, at which time fluorescence was read using an M5 Spectramax. Each compound was screened in duplicate, and composite z-scores were calculated using DMSO controls as reference. Compounds were compounds that could inhibit growth or kill *M. tuberculosis* were defined as compounds with a composite z-score of less than −6. This z-score cutoff was selected as the z-score of the concentration of the control antibiotic rifampicin that gave a Z'-factor of 0.

Alternative Carbon starvation assay. Carbon starved bacteria were diluted and plated into 384 well plates into which compounds had already been pinned for a final OD600 of 0.005 and final volume of 50 uL. The plates were incubated for 96 hours, at which time 12 uL of concentrated media was added. Plates were incubated for an additional 72 hours. For Alamar blue detection, a solution of 3 parts 18.2% Tween-80 to 4 parts Alamar Blue (3/7th Tween-80 to 4/7th Alamar Blue) is made and 9 ul added to each well in the plate. The plates are incubated (stacked 2-3 high) overnight at 37° C. in humidified incubator. The plates are removed from the incubator and sealed with aluminum seals. The fluorescence is read using the Envision plate reader (bottom read) with an excitation wavelength of 531 nm and an emission wavelength of 595 nm (Excitation filter=BODIPY TMR FP 531, barcode 105; Emission filter=Photometric 595, barcode 315; Mirror=BODIPY TMR, barcode 405).

Replicating, Logarithmic Assay.
For *M. tuberculosis* screening assays for logarithmically growing, actively replicating activity, bacteria expressing GFP was grown to mid-log phase (OD600=0.6-0.8), diluted, and plated into 384 well plates into which compounds had previously been pinned for a final OD600 of 0.025. Plates were incubated for a period of 72 h, at which time GFP fluorescence is read. Each compound is screened in duplicate, and composite z-scores were calculated using DMSO controls as reference. Compounds that inhibit replicating *M. tuberculosis* were defined as compounds with a composite z-score of less than −4. This z-score cutoff was selected using average of the z-scores of the concentrations of the control antibiotics clofazimine and rifampicin that gave a Z'-factor of 0.

Replicating IC90 Determination by OD600.
For dose response curves and IC90 determinations by OD600, bacteria were grown to mid-log phase and plated in 96 well plates at OD600=0.05 in the presence of small molecule inhibitors for 7 days unless otherwise indicated, and growth was assessed by reading OD600. The IC90 was defined as the minimum concentration that inhibited growth by 90% relative to the DMSO control (31).

Non-replicating IC90 determination by luciferase.
For the luciferase secondary screen that tests for activity of small molecules directly on non-replicating cells without an outgrowth phase, carbon-starved *M. tuberculosis* H37Rv containing an inducible firefly luciferase plasmid was dispersed into 96-well plates containing the small molecules and anhydotetracycline 50 nM (to induce luciferase expression). After 5 days the cells were lysed, luciferase reagent added and luminescence measured (Promega Corporation, Madison Wis.) in a Spectramax M5 (Molecular Devices). The antibiotic rifampicin (at 80× the MIC) was used as a positive control for the assay. Hits were defined as small molecules that resulted in ≥95% inhibition of luciferase signal.

Replicating IC90 Determinations by CFU.
To confirm the replicating IC90 values determined using OD600, the activity of selected small molecules were tested by plating for colony forming units (CFU). *M. tuberculosis* H37Rv was grown to mid-log phase and plated in 96 well plates at OD600=0.025 in the presence of small molecule inhibitors for specified time periods. The number of surviving bacteria was then determined by plating a dilution series of the culture for colony forming units (CFU). The IC90 was defined the concentration tested that inhibited growth by at least 90% relative to the DMSO control.

Non-Replicating IC90 Determinations by CFU.

To confirm the non-replicating IC90 values determined using the luciferase reporter, the activity of selected small molecules was tested by plating for CFU. Carbon-starved bacteria were diluted to OD600=0.05 in starvation media and plated in 96 well plates in the presence of small molecule inhibitors for indicated time periods. The number of surviving bacteria was then determined by plating a dilution series of the culture for colony forming units (CFU). The IC90 was defined as the concentration tested that inhibited survival by at least 90% relative to the DMSO control.

Generating Resistant Mutants.

The MIC of each compound on solid media was identified by plating $10^7$ bacteria on agar containing a dose response in 96 well plate format. The MIC was defined as the lowest concentration resulting in inhibition of bacterial growth. Resistant mutants were generated by plating M. tuberculosis cells onto agar pads containing 2× and 10× the agar MIC of each compound using four independently derived wild-type clones. Colonies that arose on inhibitor containing plates were inoculated into liquid media containing 1× the liquid MIC of the inhibitor. These cultures were grown to mid-log and samples were retested in a liquid MIC assay to confirm that a shift relative to the wild-type MIC was observed.

Macrophage Toxicity Assay.

To determine macrophage toxicity, J774 macrophages were plated in 96 well plates at a concentration of $6.25 \times 10^4$ cells/well and rested overnight. A dilution series of the small molecule being tested was then added to the plates in quadruplicate. The top concentration tested was 50 uM. The plates were incubated for 48 hours, upon which time Cell-Titer-Glo (Promega Corporation) was used as a readout for macrophage viability.

Example 2: Synthesis of Compounds

Synthesis of 2-(4-chlorophenyl)-5-(((1-phenyl-1H-1,2,3-triazol-4-yl)methyl)thio)-1,3,4-oxadiazole The compound below was synthesized by the two-step protocol scheme outlined below. Alkylation of 5-(4-chlorophenyl)-1,3,4-oxadiazole-2-thiol (1) with propagyl bromide yielded 2-(4-chlorophenyl)-5-(prop-2-yn-1-ylthio)-1,3,4-oxadiazole (2). The resulting adduct 2 was then reacted with phenylazide to undergo cycloaddition reaction under microwave irradiation condition to provide the 2-(4-chlorophenyl)-5-(((1-phenyl-1H-1,2,3-triazol-4-yl)methyl)thio)-1,3,4-oxadiazole.

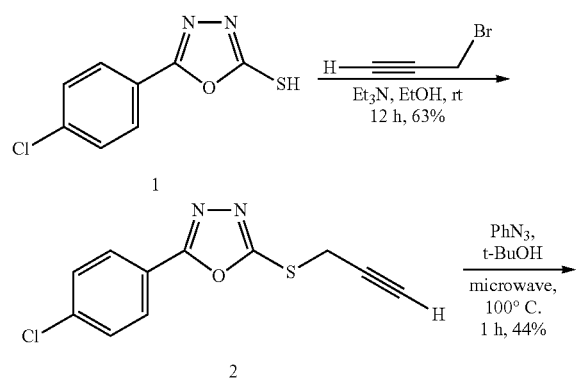

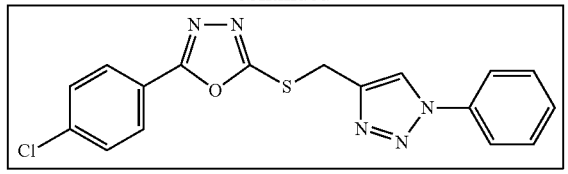

All reagents and solvents were purchased from commercial vendors and used as received. NMR spectra were recorded on a Bruker 300 MHz or Varian UNITY INOVA 500 MHz spectrometer as indicated. Proton, fluorine, and carbon chemical shifts are reported in parts per million (ppm; δ) relative to tetramethylsilane or CDCl₃ solvent ($^1$H δ 0, $^{19}$F δ 0, $^{13}$C δ 77.16, respectively). NMR data are reported as follows: chemical shifts, multiplicity (obs=obscured, app=apparent, br=broad, s=singlet, d=doublet, t=triplet, q=quartet, m=multiplet); coupling constant(s) in Hz; integration. Unless otherwise indicated, NMR data were collected at 25° C. Flash chromatography was performed using 40-60 um Silica Gel (60 Å mesh) on a Teledyne Isco Combiflash Rf system. Tandem liquid chromatography/mass spectrometry (LCMS) was performed on a Waters 2795 separations module and Waters 3100 mass detector. Analytical thin layer chromatography (TLC) was performed on EM Reagent 0.25 mm silica gel 60-F plates. Visualization was accomplished with UV light and aqueous potassium permanganate (KMnO₄) stain followed by heating. Liquid chromatography/mass spectrometry (LCMS) was performed on an Agilent 1290 Infinity separations module and 6230 time-of-flight (TOF) mass detector operating in ESI+ mode. Compound purity and identity were determined by UPLC-MS (Waters, Milford, Mass.). Purity was measured by UV absorbance at 210 nm. Identity was determined on a SQ mass spectrometer by positive electrospray ionization. Mobile Phase A consisted of either 0.1% ammonium hydroxide or 0.1% trifluoroacetic acid in water, while mobile Phase B consisted of the same additives in acetonitrile. The gradient ran from 5% to 95% mobile Phase B over 0.8 minutes at 0.45 mL/min. An Acquity BEH C18, 1.7 um, 1.0×50 mm column was used with column temperature maintained at 65° C. Compounds were dissolved in DMSO at a nominal concentration of 1 mg/mL, and 0.25 uL of this solution was injected.

Synthetic Procedure for TB Compound

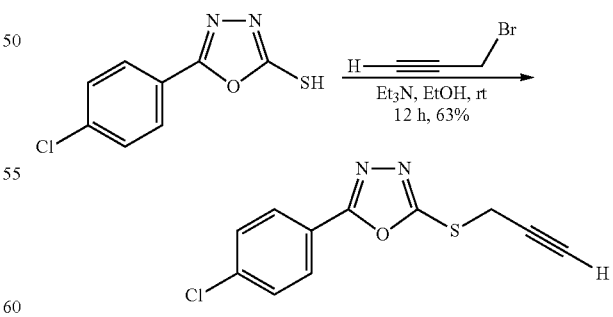

To a solution of 2.50 g (11.8 mmol) of 5-(4-chlorophenyl)-1,3,4-oxadiazole-2-thiol in 50 mL of EtOH and 2 mL of Et₃N was added 1.54 g (12.9 mmol) of propargyl bromide and the solution was stirred overnight. White crystals appeared after cooling with an ice bath, the crystals were filtered and rinsed with cold EtOH. The mother liquors were concentrated and cooled to obtain more pure material, 1.82 g of white crystals (63%) was obtained. $^1$H NMR (CDCl$_3$, 300 MHz) δ 7.96 (d, J=8.47 Hz, 2H), 7.49 (d, J=8.49 Hz, 2H), 4.07 (s, 2H), 2.35 (s, 1H); $^{13}$C NMR (CDCl$_3$, 75 MHz) δ 165.38, 162.84, 138.08, 129.45, 127.98, 121.92, 77.19, 73.05, 21.14.

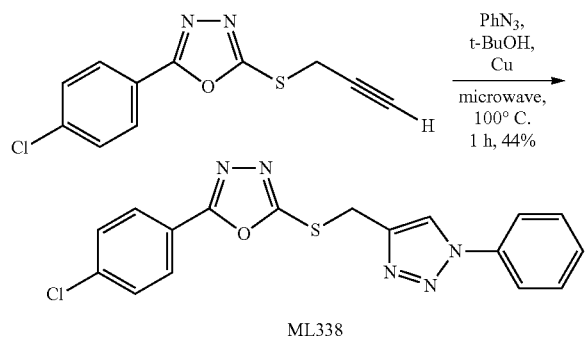

ML338

To a mixture of 200 mg of this alkyne (0.80 mmol) in 3.5 mL of t-BuOH in a small microwave vial was added 1.6 mL of a 0.5 M solution of phenyl azide (0.80 mmol) in 2-methyl tetrahydrofuran and 50 mg of copper metal. The mixture was heated at 100° C. with microwave irradiation for 1 h. Water and EtOAc were added to the reaction mixture, the separated EtOAc layer was dried, filtered, and concentrated. The crude material was purified by chromatography with a gradient of 20-50% EtOAc in hexane to isolate 129 mg of product as a white solid (44%) which could be recrystallized from EtOH. $^1$H NMR (CDCl$_3$, 300 MHz) δ 8.23 (s, 1H), 7.93 (d, J=8.55 Hz, 2H), 7.71 (d, J=7.67 Hz, 2H), 7.43-7.54 (m, 5H), 4.69 (s, 1H); $^{13}$C NMR (CDCl$_3$, 75 MHz) δ 165.39, 164.16, 143.59, 138.09, 136.86, 129.74, 129.50, 128.91, 127.93, 121.92, 121.57, 120.61, 26.89. HRMS (ESI$^+$): calculated for C$_{17}$H$_{12}$ClN$_5$OS [M+H] 370.0524. found 370.0527.

Additional analogues suitable for this protocol were synthesized utilizing this Protocol Protocol B: Thio-Oxadiazole Formation

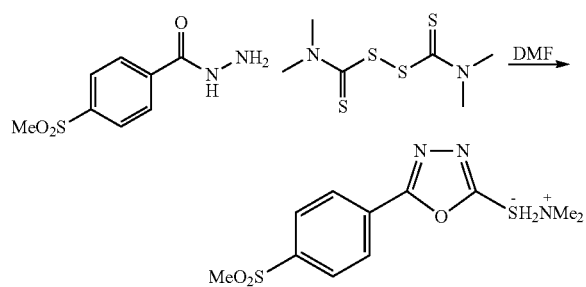

To 10 mL of DMF was added 1.0 g of 4-(methylsulfonyl) benzohydrazide (4.7 mmol), and 1.4 g of tetramethylthiuram disulfide (5.6 mmol) and the mixture was heated at 100° C. for 30 min before cooling and concentration. The residual DMF was removed by addition of toluene and evaporating (3×), the resulting solid was stirred in toluene, filtered, and rinsed with toluene to yield 1.2 g of pale yellow solid as the dimethyl-ammonium salt (100%). $^1$H NMR (DMSO-d$_6$, 300 MHz) δ 8.03 (s, 4H), 3.28 (s, 3H), 2.59 (s, 6H); $^{13}$C NMR (75 MHz, DMSO-d6) δ 181.16, 159.77, 140.81, 129.41, 127.88, 125.32, 43.41, 34.40.

Benzylation of Thio-Oxadiazole Ammonium Salt

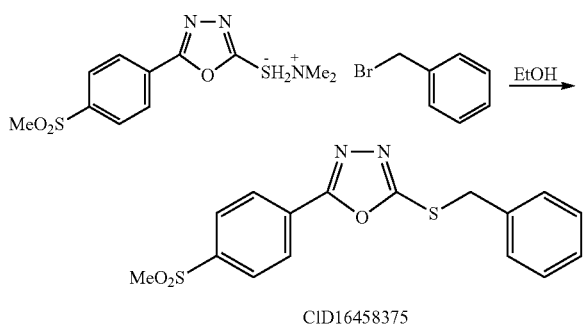

CID16458375

To 200 mg of the dimethylammonium salt (0.66 mmol) in 5 mL EtOH was added 1.43 g (0.093 mL, 0.78 mmol) of benzyl bromide. White solids were seen within minutes and the mixture was stirred overnight before filtration and rinsing with EtOH to yield 195 mg of product (85%). $^1$H NMR (300 MHz, CDCl$_3$) δ 8.19 (d, J=8.1, 2H), 8.08 (d, J=8.5, 2H), 7.47 (d, J=7.2, 2H), 7.42-7.28 (m, 3H), 4.56 (s, 2H), 3.11 (s, 3H). $^{13}$C NMR (75 MHz, CDCl$_3$) δ 163.83, 162.71, 141.50, 133.74, 127.60, 127.31, 126.82, 126.69, 125.87, 42.82, 35.32.

Protocol C: Benzylation of Thio-Oxadiazoles

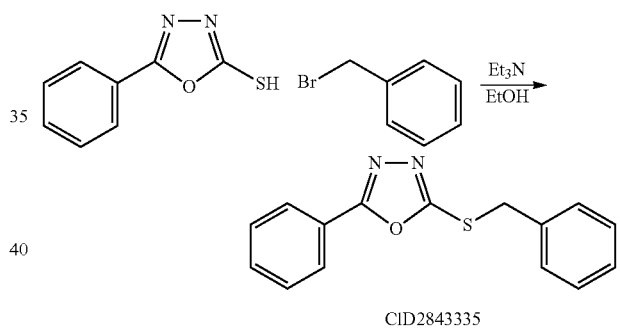

CID2843335

To a solution of 1.07 g of 5-phenyl-1,3,4-oxadiazole-2-thiol (6.00 mmol) in 40 mL of 95% EtOH and 0.84 mL of Et$_3$N (6.0 mmol) was added 1.03 g of benzyl bromide (0.72 mL, 6.0 mmol). White precipitate was seen after ca. 1 h, after 2 h the precipitate was filtered off and rinsed with EtOH to yield 1.20 g product (75%) which could be recrystallized from EtOH. $^1$H NMR (CDCl$_3$, 300 MHz) δ 7.97-8.01 (m, 2H), 7.46-7.53 (m, 5H), 7.30-7.38 (m, 3H), 4.53 (s, 2H); $^{13}$C NMR (75 MHz, CDCl$_3$) δ 165.73, 163.76, 135.54, 131.54, 129.05, 128.93, 128.71, 128.00, 126.56, 123.54, 36.76.

Additional analogues were synthesized utilizing these protocol.

Protocol D:

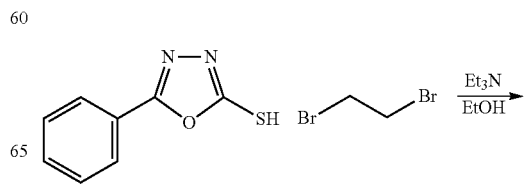

-continued

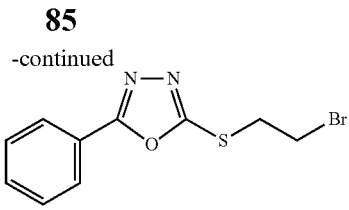

To a solution of 4.0 g of 5-phenyl-1,3,4-oxadiazole-2-thiol (22.5 mmol) in 125 mL of DCM and 5 mL of Et$_3$N was added 42 g of 1,2-dibromoethane (19 mL, 220 mmol) via an addition funnel and the reaction was stirred overnight. The solution was rinsed with water, dried, filtered and concentrated before two recrystallizations from ethanol to yield 3.8 g (60%) of product as a white solid. $^1$H NMR (CDCl$_3$, 300 MHz) δ 8.01 (dd, J=7.68, 1.63, 2H), 7.47-7.57 (m, 3H), 3.68-3.83 (m, 4H); $^{13}$C NMR (75 MHz, CDCl$_3$) δ 166.03, 162.98, 131.77, 129.02, 126.62, 123.29, 34.03, 29.24.

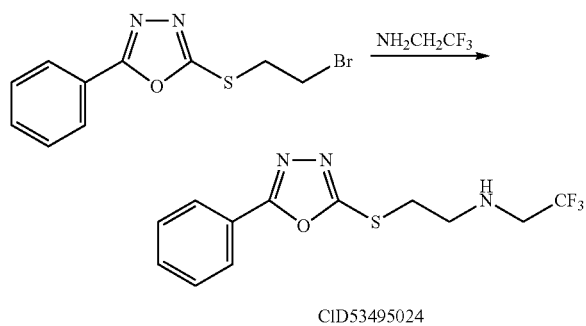

CID53495024

To a solution of 250 mg (0.88 mmol) of the bromide in 1 mL of DMF was added 1.0 mL of 2,2,2-trifluoroethylamine (13 mmol) and the reaction was stirred several days. EtOAc and water were added, the water was rinsed several times with EtOAc and the combined EtOAc layers were rinsed with brine, dried, filtered and concentrated to an oil. The crude product was dissolved in MeOH and placed onto a column of acidic resin (5 g SCX resin, Isolute brand), flushed with MeOH and the basic product was then eluted with a solution of NH$_3$ in MeOH. The impure material obtained was then chromatographed with 20-50% EtOAc to isolate 64 mg of product (24%). $^1$H NMR (CDCl$_3$, 300 MHz) δ 10.24 (s, 1H), 7.87 (d, J=7.31, 2H), 7.40-7.48 (m, 3H), 4.23 (q, J=6.92 Hz, 2H), 3.80 (t, J=6.78, 2H), 3.24 (t, J=6.75 Hz, 2H); $^{19}$F NMR (CDCl$_3$, 282 MHz) δ −64.75 (t, J=9.22 Hz).

Additional analogues were synthesized utilizing this protocol.

Protocol E:

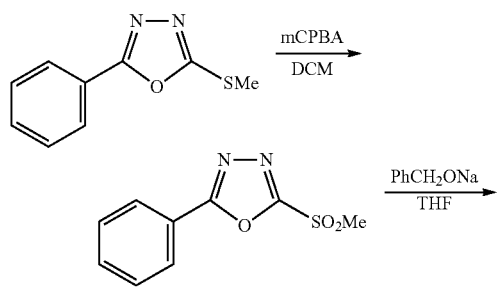

-continued

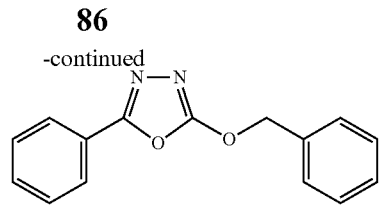

CID21827731

To a solution of 166 mg of 2-(methylthio)-5-phenyl-1,3,4-oxadiazole (0.864 mmol) in 5 mL DCM cooled in an ice bath was added 298 mg of mCPBA (70% max., ca. 2 eq.) and the solution was stirred overnight, warming to room temperature. The mixture was added directly to a silica gel column and eluted with 0-20% EtOAc in hexane to isolate 119 mg of product as a white solid (62%). $^1$H NMR (300 MHz, CDCl$_3$) δ 8.19-8.03 (m, 2H), 7.65 (t, J=7.3, 1H), 7.56 (t, J=7.3, 2H), 3.54 (s, 3H). $^{13}$C NMR (75 MHz, CDCl$_3$) δ 166.61, 162.10, 133.28, 129.36, 127.73, 122.03, 42.96.

To 35 mg of benzyl alcohol (0.32 mmol) dissolved in 1 mL of THF was added NaH (60% oil dispersion, 13 mg, ca. 0.32 mmol) and the mixture was stirred 1 h before addition of a solution of 60 mg of the sulfoxide (0.27 mmol) in 1 mL THF. After stirring overnight, EtOAc and water were added, the EtOAc was separated, dried, concentrated and chromatographed with 0-20% EtOAc in hexane to isolate 37 mg of product as a white solid (55%). $^1$H NMR (300 MHz, CDCl$_3$) δ 8.01-7.84 (m, 2H), 7.58-7.33 (m, 8H), 5.54 (s, 2H). $^{13}$C NMR (75 MHz, CDCl$_3$) δ 165.66, 160.73, 133.87, 131.24, 129.27, 128.95, 128.83, 128.79, 126.09, 124.08, 74.49.

Additional analogues were synthesized utilizing this protocol.

Protocol F:

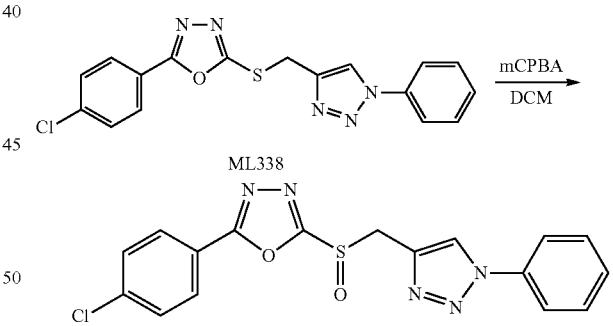

To a solution of 34 mg (0.092 mmol) of sulfide in 1 mL of DCM was added 20.6 mg of mCPBA (70% max., ca. 1 eq.) and the solution was stirred overnight before direct addition to a silica gel column and elution with 20-50% EtOAc in hexane to isolate 27 mg of product as a white solid (76%). $^1$H NMR (CDCl$_3$, 300 MHz) δ 8.21 (s, 1H), 8.02 (d, J=8.53 Hz, 2H), 7.72 (d, J=7.46 Hz, 2H), 7.44-7.56 (m, 5H), 5.01 (d, J=13.92 Hz, 1H), 4.84 (d, J=13.93, 1H); $^{13}$C NMR (CDCl$_3$, 75 MHz) δ 166.63, 165.33, 139.39, 136.62, 135.65, 129.87, 129.71, 129.22, 128.79, 123.09, 121.03, 120.57, 50.58.

Additional analogues were synthesized utilizing this protocol.

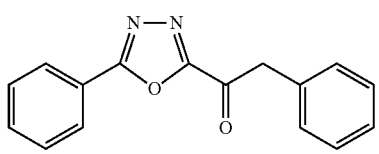 [SMILES: O=C(Cc1ccccc1)c1nnc(-c2ccccc2)o1]

was synthesized by following procedure reported in literature Zarudnitskii, E. V.; Pervak, I. I.; Merkulov, A. S.; Yurchenko, A. A.; Tolmachev, A. A. *Tetrahedron* 2008, 64, 10431-10442.

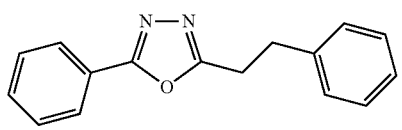 [SMILES: c1ccc(CCc2nnc(-c3ccccc3)o2)cc1]

was synthesized by following procedure reported in literature: Wang, Y.; Sauer, D. R.; Djuric, S. W. *Tetrahedron Lett.* 2006, 47, 105-108.

Example 3: Characteristics of 2-(4-chlorophenyl)-5-(((1-phenyl-1H-1,2,3-triazol-4-yl)methyl)thio)-1,2,3,4-oxadiazole The compound was tested against TB according to the assays described in Example 1. Does response curves for the compound were determined. FIG. 1A is a dose response curve against replicating, logarithmically growing bacteria measured by OD600. (AID xx), $IC_{90}$>62 uM FIG. 1B is a dose response against replicating, logarithmically growing bacteria measured by CFU/mL. (AID xx), $IC_{90}$>62 uM FIG. 1C is a dose response curve for non-replicating starved cells by luciferase assay. (AID xx) $IC_{90}$>62 uM FIG. 1D is a dose response against non-replicating, starved cells by CFU/mL. (AID xx) $IC_{90}$=1 uM as shown in FIGS. 1A-1D.

Example 4: Testing of Additional Compounds

The following compounds were tested against replicating and non-replicating TB according to the assays described in Example 1. As can be seen some compounds can inhibit the growth of both replicating and non-replicating TB, whereas others are more selective or completely selective. The results are shown in the following table.

| Compound | TB Growth Inhibition Activity, $IC_{90}$ (uM)[†] | | Cytotoxicity |
| --- | --- | --- | --- |
| | Non-replicating _luciferase | Replicating _logarithmic | $IC_{50}$ (uM)* Hek 293/ HepG2/HeLa |
| (5-phenyl-1,3,4-oxadiazol-2-yl S-CH2-phenyl) | 8 | 62 | >26.0 |
| (5-phenyl-1,3,4-thiadiazol-2-yl S-CH2-phenyl) | 8 | 62 | >26.0 |
| (5-phenyl-oxazol-2-yl S-CH2-phenyl) | 62 | N.A | >26.0 |
| (5-phenyl-1,3,4-oxadiazol-2-yl O-CH2-phenyl) | 8 | N.A | >26.0 |
| (5-phenyl-1,3,4-oxadiazol-2-yl NH-CH2-phenyl) | 4 | N.A | >26.0 |
| (5-phenyl-1,3,4-oxadiazol-2-yl N(Me)-CH2-phenyl) | 0.5 | 250 | >26.0 |

-continued

| Compound | TB Growth Inhibition Activity, IC$_{90}$ (uM)† | | Cytotoxicity |
|---|---|---|---|
| | Non-replicating _luciferase | Replicating _logarithmic | IC$_{50}$ (uM)* Hek 293/ HepG2/HeLa |
| 5-phenyl-2-(2-phenylethyl)-1,3,4-oxadiazole | 0.5 | 250 | >26.0 |
| 1-(5-phenyl-1,3,4-oxadiazol-2-yl)-2-phenylethanone | 16 | N.A | >26.0 |
| 2-(benzylsulfinyl)-5-phenyl-1,3,4-oxadiazole | 8 | 125 | >26.0 |
| 2-(benzylsulfonyl)-5-phenyl-1,3,4-oxadiazole | 8 | 125 | >26.0 |
| 2-(benzylthio)-5-cyclohexyl-1,3,4-oxadiazole | 1 | 125 | >26.0 |
| 2-(benzylthio)-5-cyclopentyl-1,3,4-oxadiazole | 0.5 | 125 | >26.0 |
| 2-(benzylthio)-5-isopropyl-1,3,4-oxadiazole | 2 | 125 | >26.0 |
| 2-(benzylthio)-5-methyl-1,3,4-oxadiazole | 31 | N.A | >26.0 |
| 2-benzyl-5-(benzylthio)-1,3,4-oxadiazole | 4 | 500 | >26.0 |

-continued

| Compound | TB Growth Inhibition Activity, IC$_{90}$ (uM)† | | Cytotoxicity |
|---|---|---|---|
| | Non-replicating _luciferase | Replicating _logarithmic | IC$_{50}$ (uM)* Hek 293/ HepG2/HeLa |
| 2-(phenethyl)-5-(benzylthio)-1,3,4-oxadiazole | 32 | 250 | >26.0 |
| 2-(4-biphenyl)-5-(benzylthio)-1,3,4-oxadiazole | N.A | N.A | >26.0 |
| 2-(2-methylphenyl)-5-(benzylthio)-1,3,4-oxadiazole | 16 | N.A | >26.0 |
| 2-(2-methoxyphenyl)-5-(benzylthio)-1,3,4-oxadiazole | 125 | 250 | >26.0 |
| 2-(2-fluorophenyl)-5-(benzylthio)-1,3,4-oxadiazole | 2 | 125 | >26.0 |
| 2-(2-chlorophenyl)-5-(benzylthio)-1,3,4-oxadiazole | 32 | 250 | >26.0 |
| 2-(2-trifluoromethoxyphenyl)-5-(benzylthio)-1,3,4-oxadiazole | 62 | N.A | >26.0 |
| 2-(2-trifluoromethylphenyl)-5-(benzylthio)-1,3,4-oxadiazole | 62 | 500 | >26.0 |
| 2-(2-methylsulfonylphenyl)-5-(benzylthio)-1,3,4-oxadiazole | 62 | 500 | >26.0 |

-continued
| Compound | TB Growth Inhibition Activity, IC$_{90}$ (uM)$^\dagger$ | | Cytotoxicity |
|---|---|---|---|
| | Non-replicating _luciferase | Replicating _logarithmic | IC$_{50}$ (uM)* Hek 293/ HepG2/HeLa |
| 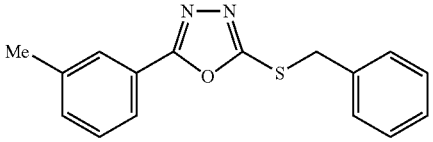 | 8 | N.A | >26.0 |
| 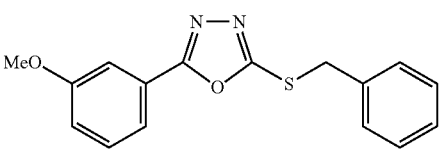 [SMILES: COc1cccc(-c2nnc(SCc3ccccc3)o2)c1] | 8 | 250 | >26.0 |
| 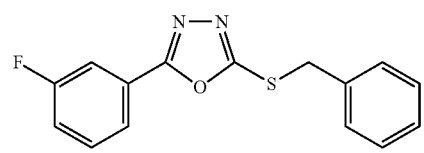 [SMILES: Fc1cccc(-c2nnc(SCc3ccccc3)o2)c1] | 1 | 125 | >26.0 |
| 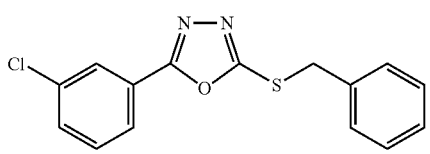 [SMILES: Clc1cccc(-c2nnc(SCc3ccccc3)o2)c1] | 8 | N.A | >26.0 |
| 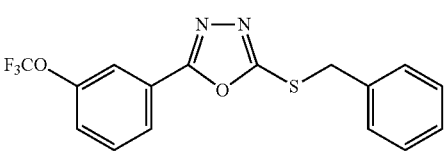 [SMILES: FC(F)(F)Oc1cccc(-c2nnc(SCc3ccccc3)o2)c1] | 31 | 250 | >26.0 |
| 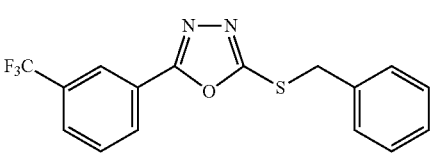 | 31 | N.A | >26.0 |
| 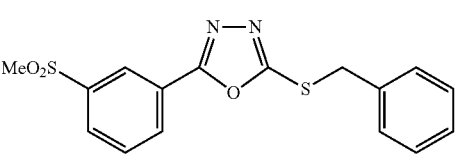 [SMILES: CS(=O)(=O)c1cccc(-c2nnc(SCc3ccccc3)o2)c1] | 125 | N.A | >26.0 |
| 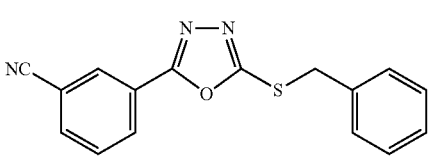 [SMILES: N#Cc1cccc(-c2nnc(SCc3ccccc3)o2)c1] | 8 | N.A | >26.0 |
| 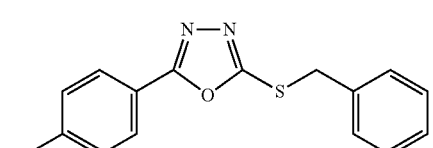 | 4 | 125 | >26.0 |

-continued
| Compound | TB Growth Inhibition Activity, IC$_{90}$ (uM)$^\dagger$ | | Cytotoxicity IC$_{50}$ (uM)* Hek 293/ HepG2/HeLa |
|---|---|---|---|
| | Non-replicating _luciferase | Replicating _logarithmic | |
| 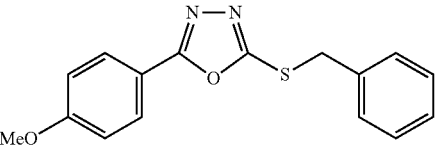 [SMILES: COc1ccc(-c2nnc(SCc3ccccc3)o2)cc1] | 31 | N.A | >26.0 |
| 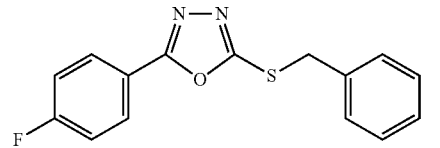 [SMILES: Fc1ccc(-c2nnc(SCc3ccccc3)o2)cc1] | 2 | 125 | >26.0 |
| 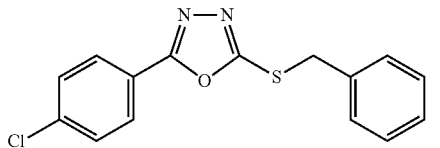 [SMILES: Clc1ccc(-c2nnc(SCc3ccccc3)o2)cc1] | 4 | 500 | >26.0 |
| 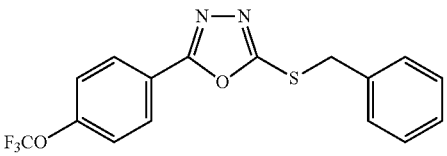 [SMILES: FC(F)(F)Oc1ccc(-c2nnc(SCc3ccccc3)o2)cc1] | 2 | N.A | >26.0 |
| 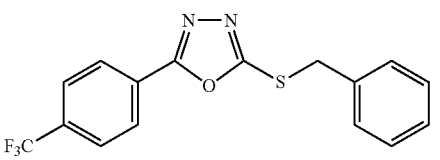 [SMILES: FC(F)(F)c1ccc(-c2nnc(SCc3ccccc3)o2)cc1] | 1 | N.A | >26.0 |
| 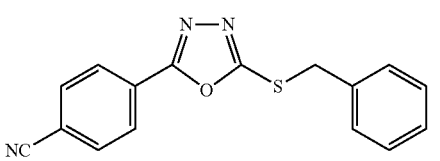 [SMILES: N#Cc1ccc(-c2nnc(SCc3ccccc3)o2)cc1] | 8 | N.A | >26.0 |
| 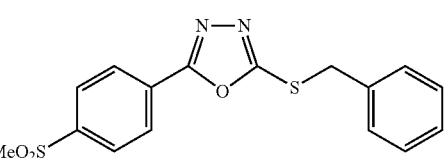 | N.A | N.A | >26.0 |
| 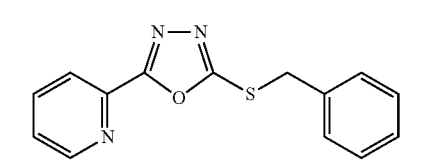 [SMILES: c1ccc(CSc2nnc(-c3ccccn3)o2)cc1] | 4 | 125 | >26.0 |
| 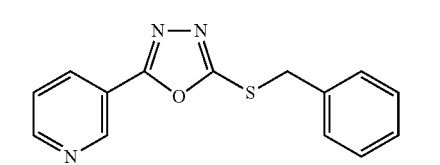 [SMILES: c1ccc(CSc2nnc(-c3cccnc3)o2)cc1] | 2 | 125 | >26.0 |

| Compound | TB Growth Inhibition Activity, IC$_{90}$ (uM)[†] | | Cytotoxicity |
|---|---|---|---|
| | Non-replicating _luciferase | Replicating _logarithmic | IC$_{50}$ (uM)* Hek 293/ HepG2/HeLa |
| 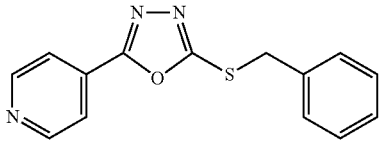 [SMILES: c1ccc(CSc2nnc(-c3ccncc3)o2)cc1] | 31 | N.A | >26.0 |
| 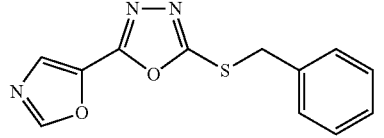 [SMILES: c1ccc(CSc2nnc(-c3cnco3)o2)cc1] | 8 | N.A | >26.0 |
| 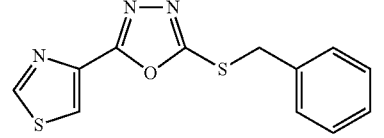 [SMILES: c1ccc(CSc2nnc(-c3cscn3)o2)cc1] | 4 | 125 | >26.0 |
| 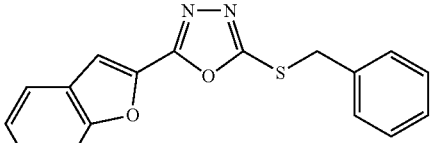 | 2 | N.A | >26.0 |
| 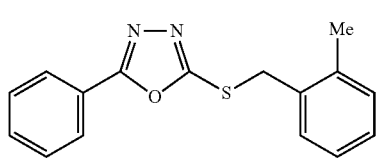 [SMILES: Cc1ccccc1CSc1nnc(-c2ccccc2)o1] | 8 | 250 | >26.0 |
| 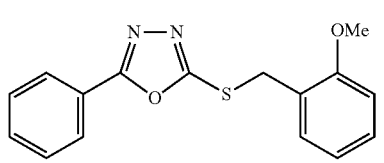 [SMILES: COc1ccccc1CSc1nnc(-c2ccccc2)o1] | 2 | N.A | >26.0 |
| 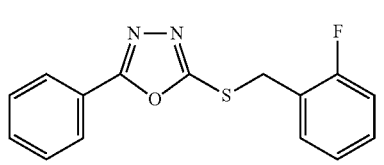 [SMILES: Fc1ccccc1CSc1nnc(-c2ccccc2)o1] | 1 | 250 | >26.0 |
| 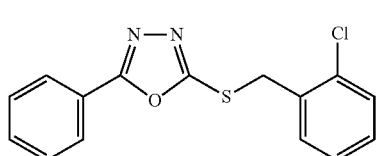 | 2 | 250 | >26.0 |
| 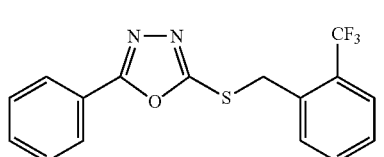 | 1 | N.A | >26.0 |

-continued

| Compound | TB Growth Inhibition Activity, IC$_{90}$ (uM)† | | Cytotoxicity |
|---|---|---|---|
| | Non-replicating _luciferase | Replicating _logarithmic | IC$_{50}$ (uM)* Hek 293/ HepG2/HeLa |
| 2-phenyl-5-((2-OCF$_3$-benzyl)thio)-1,3,4-oxadiazole | 4 | 500 | >26.0 |
| 2-phenyl-5-((2-CN-benzyl)thio)-1,3,4-oxadiazole | 4 | N.A | >26.0 |
| 2-phenyl-5-((2-SO$_2$Me-benzyl)thio)-1,3,4-oxadiazole | N.A | N.A | >26.0 |
| 2-phenyl-5-((3-Me-benzyl)thio)-1,3,4-oxadiazole | 1 | 125 | >26.0 |
| 2-phenyl-5-((3-OMe-benzyl)thio)-1,3,4-oxadiazole | 1 | N.A | >26.0 |
| 2-phenyl-5-((3-Cl-benzyl)thio)-1,3,4-oxadiazole | 4 | N.A | >26.0 |
| 2-phenyl-5-((3-F-benzyl)thio)-1,3,4-oxadiazole | 2 | 250 | >26.0 |
| 2-phenyl-5-((3-CF$_3$-benzyl)thio)-1,3,4-oxadiazole | 4 | 250 | >26.0 |
| 2-phenyl-5-((3-OCF$_3$-benzyl)thio)-1,3,4-oxadiazole | 2 | N.A | >26.0 |

-continued
| Compound | TB Growth Inhibition Activity, IC$_{90}$ (uM)† | | Cytotoxicity |
|---|---|---|---|
| | Non-replicating _luciferase | Replicating _logarithmic | IC$_{50}$ (uM)* Hek 293/ HepG2/HeLa |
| 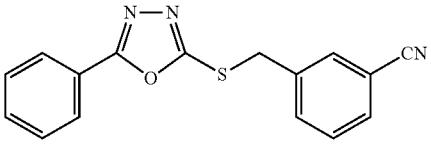 | 8 | N.A | >26.0 |
| 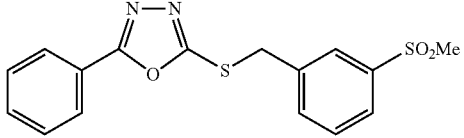 [SMILES: CS(=O)(=O)c1cccc(CSc2nnc(-c3ccccc3)o2)c1] | 250 | 250 | >26.0 |
| 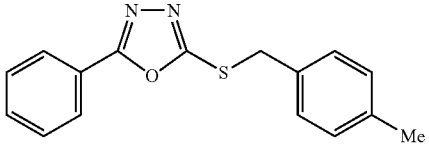 [SMILES: Cc1ccc(CSc2nnc(-c3ccccc3)o2)cc1] | 1 | N.A | >26.0 |
| 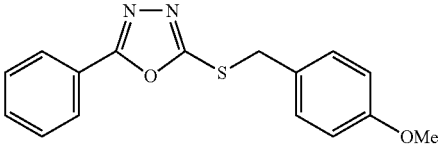 [SMILES: COc1ccc(CSc2nnc(-c3ccccc3)o2)cc1] | 0.25 | N.A | >26.0 |
| 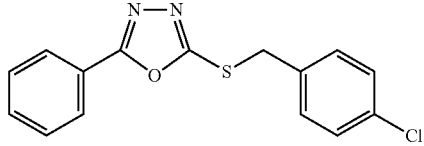 [SMILES: Clc1ccc(CSc2nnc(-c3ccccc3)o2)cc1] | 1 | N.A | >26.0 |
| 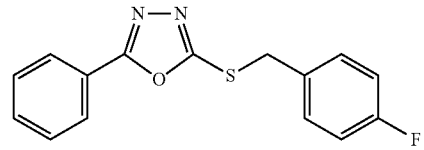 [SMILES: Fc1ccc(CSc2nnc(-c3ccccc3)o2)cc1] | 1 | N.A | >26.0 |
| 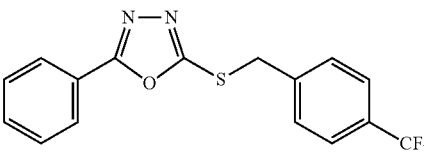 | 1 | N.A | >26.0 |
| 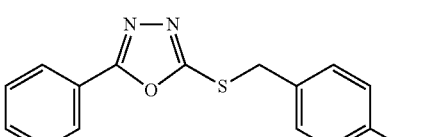 | 1 | N.A | >26.0 |
| 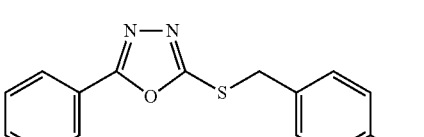 | 2 | N.A | >26.0 |

-continued

| Compound | TB Growth Inhibition Activity, IC$_{90}$ (uM)† | | Cytotoxicity |
|---|---|---|---|
| | Non-replicating _luciferase | Replicating _logarithmic | IC$_{50}$ (uM)* Hek 293/ HepG2/HeLa |
| Phenyl-oxadiazole-S-CH$_2$-C$_6$H$_4$-SO$_2$Me | 31 | N.A | >26.0 |
| Phenyl-oxadiazole-S-CH$_2$-C$_6$H$_4$-Ph | 8 | N.A | >26.0 |
| Phenyl-oxadiazole-S-CH$_2$-(2-pyridyl) | 3 | 100 | >26.0 |
| Phenyl-oxadiazole-S-CH$_2$-(3-pyridyl) | 8 | 125 | >26.0 |
| Phenyl-oxadiazole-S-CH$_2$-(4-pyridyl) | 31 | 250 | >26.0 |
| Phenyl-oxadiazole-S-CH$_2$-oxazole | 16 | 31 | >26.0 |
| Phenyl-oxadiazole-S-CH$_2$-thiazole | 4 | 62 | >26.0 |
| Phenyl-oxadiazole-S-CH$_2$-(1-benzyl-triazole) | 16 | >125 | >26.0 |
| Phenyl-oxadiazole-S-CH$_2$CH$_2$-OMe | 3 | 125 | >26.0 |

-continued
| Compound | TB Growth Inhibition Activity, IC$_{90}$ (uM)$^\dagger$ | | Cytotoxicity |
|---|---|---|---|
| | Non-replicating_luciferase | Replicating_logarithmic | IC$_{50}$ (uM)* Hek 293/ HepG2/HeLa |
| 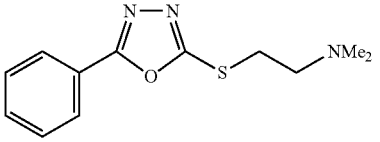 [SMILES: CN(C)CCSc1nnc(-c2ccccc2)o1] | 16 | 500 | >26.0 |
| 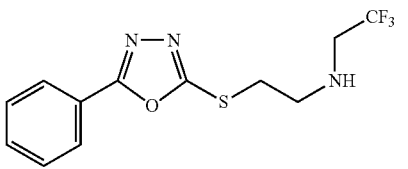 [SMILES: FC(F)(F)CNCCSc1nnc(-c2ccccc2)o1] | 250 | N.A | >26.0 |
| 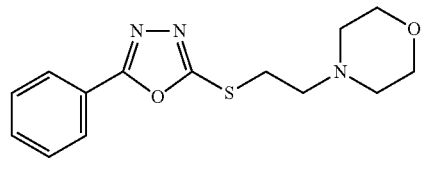 [SMILES: c1ccc(-c2nnc(SCCN3CCOCC3)o2)cc1] | 250 | N.A | >26.0 |
| 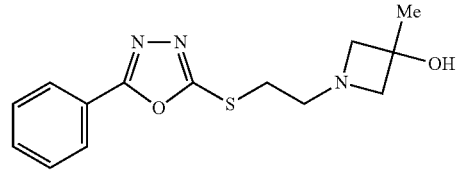 [SMILES: CC1(O)CN(CCSc2nnc(-c3ccccc3)o2)C1] | 125 | N.A | >26.0 |
| 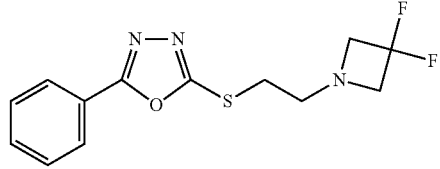 [SMILES: FC1(F)CN(CCSc2nnc(-c3ccccc3)o2)C1] | 1 | 250 | >26.0 |
| 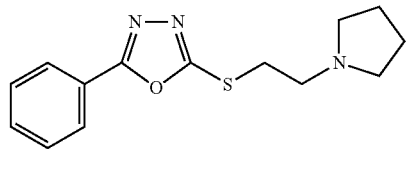 [SMILES: c1ccc(-c2nnc(SCCN3CCCC3)o2)cc1] | 16 | N.A | >26.0 |
| 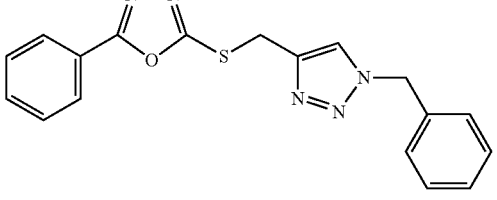 | 4 | >62 | >26.0 |
| 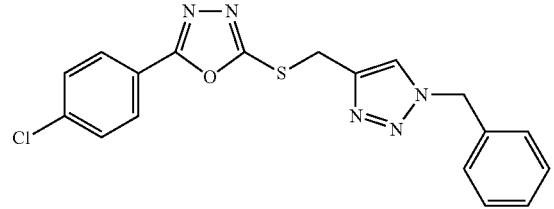 [SMILES: Clc1ccc(-c2nnc(SCc3cn(Cc4ccccc4)nn3)o2)cc1] | 2 | >62 | >26.0 |

| Compound | TB Growth Inhibition Activity, IC$_{90}$ (uM)[†] | | Cytotoxicity |
|---|---|---|---|
| | Non-replicating _luciferase | Replicating _logarithmic | IC$_{50}$ (uM)* Hek 293/ HepG2/HeLa |
| 5-(4-fluorophenyl)-2-[(1-benzyl-1H-1,2,3-triazol-4-yl)methylthio]-1,3,4-oxadiazole | 2 | >62 | >26.0 |
| 5-cyclopentyl-2-[(1-benzyl-1H-1,2,3-triazol-4-yl)methylthio]-1,3,4-oxadiazole | 31 | 62 | >26.0 |
| 5-cyclobutyl-2-[(1-benzyl-1H-1,2,3-triazol-4-yl)methylthio]-1,3,4-oxadiazole | 8 | >62 | >26.0 |
| 5-cyclopentyl-2-[(1-(4-fluorobenzyl)-1H-1,2,3-triazol-4-yl)methylthio]-1,3,4-oxadiazole | 31 | >62 | >26.0 |
| 5-cyclobutyl-2-[(1-(4-fluorobenzyl)-1H-1,2,3-triazol-4-yl)methylthio]-1,3,4-oxadiazole | 8 | >62 | >26.0 |
| 5-(4-fluorophenyl)-2-[(1-(4-fluorobenzyl)-1H-1,2,3-triazol-4-yl)methylthio]-1,3,4-oxadiazole | 4 | >62 | >26.0 |

-continued

| Compound | TB Growth Inhibition Activity, $IC_{90}$ (uM)† | | Cytotoxicity $IC_{50}$ (uM)* Hek 293/ HepG2/HeLa |
|---|---|---|---|
| | Non-replicating _luciferase | Replicating _logarithmic | |
| (4-chlorophenyl-oxadiazole-S-CH2-triazole-N-CH2-4-fluorophenyl) | 2 | >62 | >26.0 |
| (4-chlorophenyl-oxadiazole-S-CH2-triazole-N-phenyl) | 1 | >62 | >26.0 |
| (4-fluorophenyl-oxadiazole-S-CH2-triazole-N-phenyl) | 2 | >62 | >26.0 |
| (cyclobutyl-oxadiazole-S-CH2-triazole-N-phenyl) | 2 | 62 | >26.0 |
| (cyclopentyl-oxadiazole-S-CH2-triazole-N-phenyl) | 4 | 62 | >26.0 |

†Data is from three independent experiment, performed in triplicats.
*For each analogue, cytotoxicity was measured against Hek 293, HepG2 and HeLa cell lines and IC50 was determined to be >26.0 uM (highest concentration measured) for each cell line Example 5: Further Testing of Compounds Compounds were further analyzed according to the assays described in Example 1. The data demonstrates that the compounds can be used to treat tuberculosis.

TABLE

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
|---|---|---|
| (dioxane-CH2CH2-S-oxadiazole-phenyl) | 125 | 62 |

TABLE-continued

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
| --- | --- | --- |
| methylthio-phenyl-oxadiazole | >250 | None |
| ethylthio-phenyl-oxadiazole | 200 | 250 |
| dodecylthio-phenyl-oxadiazole | 125 | 62 |
| 4-fluorobenzylthio-phenyl-oxadiazole | 125 | None |
| 4-fluorophenethylthio-phenyl-oxadiazole | 250 | 250 |
| ethoxycarbonylmethylthio-phenyl-oxadiazole | 500 | 250 |
| methoxyethylthio-phenyl-oxadiazole | 125 | 16 |
| cyclopropylmethylthio-phenyl-oxadiazole | 125 | 31 |
| pyridin-2-ylmethylthio-phenyl-oxadiazole | 100 | 31 |
| pyridin-3-ylmethylthio-phenyl-oxadiazole | 125 | 250 |

TABLE-continued
Antimycobacterial activity of the compounds was determined using the fluorescent assay, either using GFP or luciferase. These assasys are described in Example 1.
| Compound | Against Replicating Mtb IC90 (uM, GFP) | Against carbon starved non-replicating Mtb IC99 (uM, luciferase) |
|---|---|---|
| 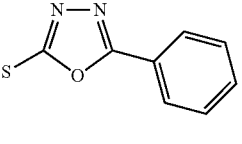 | 250 | 500 |
| 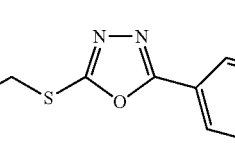 | >500 | None |
| 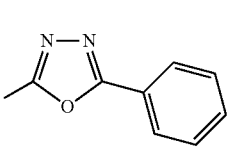 | >500 | 62 |
| 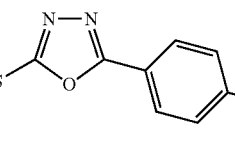 | >500 | None |
| 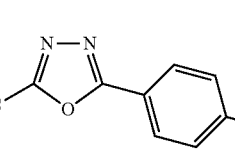 | 62 | 8 |
| 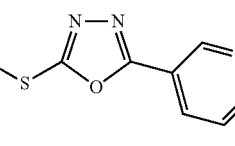 | >500 | 62 |
| 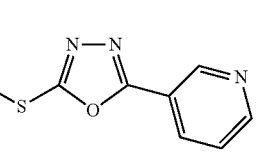 | >500 | None |
| 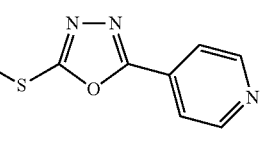 | >500 | None |
| 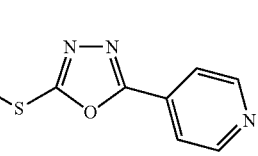 | >500 | None |

TABLE-continued

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
|---|---|---|
| pyridin-2-ylmethylthio-5-(4-chlorophenyl)-1,3,4-oxadiazole | 62 | 16 |
| 2-methoxyethylthio-5-(4-chlorophenyl)-1,3,4-oxadiazole | 50 | 16 |
| pyridin-2-ylmethylthio-5-(pyridin-3-yl)-1,3,4-oxadiazole | >500 | 250 |
| 2-methoxyethylthio-5-(pyridin-3-yl)-1,3,4-oxadiazole | >500 | None |
| pyridin-2-ylmethylthio-5-(pyridin-4-yl)-1,3,4-oxadiazole | >500 | 500 |
| 2-methoxyethylthio-5-(pyridin-4-yl)-1,3,4-oxadiazole | >500 | 500 |
| (pyridin-2-yl N-oxide)methylthio-5-phenyl-1,3,4-oxadiazole | 62 | 125 |
| pyridin-2-ylmethylsulfinyl-5-(4-chlorophenyl)-1,3,4-oxadiazole | 31 | 4 |
| 2-methoxyethylsulfinyl-5-(4-chlorophenyl)-1,3,4-oxadiazole | 31 | 31 |
| methylsulfonyl-5-phenyl-1,3,4-oxadiazole | 250 | 62 |

TABLE-continued

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
| --- | --- | --- |
| 2-methoxyethylsulfonyl-5-(4-chlorophenyl)-1,3,4-oxadiazole | >500 | 250 |
| N-(pyridin-2-ylmethyl)-5-phenyl-1,3,4-oxadiazol-2-amine | >500 | None |
| 2-(pyridin-2-ylmethoxy)-5-phenyl-1,3,4-oxadiazole | >500 | None |
| 2-methylsulfonyl-5-(4-chlorophenyl)-1,3,4-oxadiazole | 125 | 8 |
| N-(pyridin-2-ylmethyl)-5-(4-chlorophenyl)-1,3,4-oxadiazol-2-amine | 500 | 125 |
| N-(2-methoxyethyl)-5-(4-chlorophenyl)-1,3,4-oxadiazol-2-amine | >500 | None |
| 2-(pyridin-2-ylmethoxy)-5-(4-chlorophenyl)-1,3,4-oxadiazole | 250 | 250 |
| 2-((1-methylpiperidin-2-yl)methoxy)-5-(4-chlorophenyl)-1,3,4-oxadiazole | >500 | 500 |
| 2-(2-methoxyethoxy)-5-(4-chlorophenyl)-1,3,4-oxadiazole | >500 | 250 |
| 2-(2-methoxyethylthio)-5-(4-methylphenyl)-1,3,4-oxadiazole | 31 | 31 |

TABLE-continued

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
|---|---|---|
| pyridin-2-ylmethyl 5-(p-tolyl)-1,3,4-oxadiazol-2-yl sulfide | 31 | 16 |
| pyridin-2-ylmethyl 5-(p-tolyl)-1,3,4-oxadiazol-2-yl sulfoxide, N-oxide | 125 | 62 |
| 2-methoxyethyl 5-(p-tolyl)-1,3,4-oxadiazol-2-yl sulfone | 31 | 8 |
| (6-methylpyridin-2-yl)methyl 5-(4-chlorophenyl)-1,3,4-oxadiazol-2-yl sulfide | 62 | 31 |
| pyridin-2-ylmethyl 5-(4-bromophenyl)-1,3,4-oxadiazol-2-yl sulfide | 31 | 8 |
| benzyl 5-phenyl-1,3,4-oxadiazol-2-yl sulfoxide | 125 | 4 |
| benzyl 5-phenyl-1,3,4-oxadiazol-2-yl sulfone | 125 | 16 |
| pyridin-2-ylmethyl 5-(4-fluorophenyl)-1,3,4-oxadiazol-2-yl sulfide | 31 | 62 |
| pyridin-2-ylmethyl 5-(3-fluorophenyl)-1,3,4-oxadiazol-2-yl sulfide | 31 | 16 |

TABLE-continued

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
|---|---|---|
| 2-pyridyl-CH2-S-[1,3,4-oxadiazole]-3-bromophenyl | 62 | 31 |
| 2-pyridyl-CH2-S-[1,3,4-oxadiazole]-4-methoxyphenyl | 62 | 16 |
| propargyl-S-[1,3,4-oxadiazole]-4-chlorophenyl | 31 | 16 |
| 2-pyridyl-CH2-S-[1,3,4-oxadiazole]-4-hydroxyphenyl | 125 | 62 |
| HO-CH2-C≡C-CH2-S-[1,3,4-oxadiazole]-4-chlorophenyl | 62 | 8 |
| 2-pyridyl-CH2-S-[1,3,4-oxadiazole]-phenyl-O-CH2-C(O)-O-ethyl | None | 31 |
| 1-benzyl-triazole-CH2-S(O)-[1,3,4-oxadiazole]-4-chlorophenyl | 62 | 8 |
| 1-benzyl-triazole-CH2-S-[1,3,4-oxadiazole]-4-chlorophenyl | None | 16 |

TABLE-continued

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
|---|---|---|
| MeO-pyridine-CH2-S-(1,3,4-oxadiazole)-C6H4-Cl methyl ester | None | 16 |
| pyridine-CH2-S-(1,3,4-oxadiazole)-C6H4-OMe (ortho) | None | 125 |
| pyridine-CH2-S-(1,3,4-oxadiazole)-C6H4-OMe (meta) | 62 | 16 |
| 5-methoxypyridine-CH2-S-(1,3,4-oxadiazole)-C6H4-Cl | 31 | 8 |
| pyridine-CH2-S-(1,3,4-oxadiazole)-C6H4-OH | 125 | 62 |
| pyridine-CH2-S-(1,3,4-oxadiazole)-C6H4-O-(CH2)3-C(O)OMe | 500 | 250 |
| 4-tBu-C6H4-CH2-S-(1,3,4-oxadiazole)-C6H4-Cl | 250 | 62 |
| MeO2C-pyridine-CH2-S(=O)-(1,3,4-oxadiazole)-C6H4-Cl | 125 | 4 |

TABLE-continued

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
|---|---|---|
| [structure] | 31 | 16 |
| [structure] | 125 | 31 |
| [structure] | 125 | 62 |
| [structure] | 125 | None |
| [structure] | 62 | 62 |
| [structure] | 250 | 62 |
| [structure] | 125 | 31 |

TABLE-continued

Antimycobacterial activity of the compounds was determined using the fluorescent assay, either using GFP or luciferase. These assays are described in Example 1.

| Compound | Against Replicating Mtb IC90 (uM, GFP) | Against carbon starved non-replicating Mtb IC99 (uM, luciferase) |
|---|---|---|
| [structure] | 250 | 16 |
| [structure] | 250 | None (IC90 = 4) |
| [structure] | None | None (IC90 = 1) |
| [structure] | 250 | 250 (IC90 = 1) |
| [structure] | 500 | 500 (IC90 = 125) |
| [structure] | 31 | 16 |
| [structure] | 31 | 16 |

TABLE-continued

Antimycobacterial activity of the compounds was determined using the fluorescent assay, either using GFP or luciferase. These assasys are described in Example 1.

| Compound | Against Replicating Mtb IC90 (uM, GFP) | Against carbon starved non-replicating Mtb IC99 (uM, luciferase) |
|---|---|---|
| (azidopropoxy-pyridinyl-methyl-sulfinyl-oxadiazole-fluorophenyl) | 31 | 4 |
| (pentynyloxy-pyridinyl-methyl-sulfinyl-oxadiazole-fluorophenyl) | 31 | 31 |
| (pyridinyl-methyl-sulfinyl-oxadiazole-phenyl-propargyloxy) | 31 | 31 |
| (pyridinyl-methyl-sulfanyl-oxadiazole-phenyl-pentynyloxy) | None | 16 |
| (pyridinyl-methyl-sulfanyl-oxadiazole-methoxy-fluorophenyl) | None | 16 |
| (pyridinyl-methyl-sulfanyl-oxadiazole-pentynyloxy-methoxyphenyl) | None | 16 |
| (pyridinyl-methyl-sulfanyl-oxadiazole-pentynyloxy-fluorophenyl) | None | 64 (IC90 = 4) |
| (hydroxyethyl-triazolyl-methyl-sulfanyl-oxadiazole-chlorophenyl) | 62 | 31 |

TABLE-continued

Antimycobacterial activity of the compounds was determined using the fluorescent
assay, either using GFP or luciferase. These assasys are described in Example 1.

| Compound | Against Replicating Mtb IC90 (uM, GFP) | Against carbon starved non-replicating Mtb IC99 (uM, luciferase) |
|---|---|---|
| MeO-pyridine-CH2-S-oxadiazole-C6H4-F | | 16~31 |
| pyridine-CH2-S(O)-oxadiazole-C6H4-F | | 31 |
| MeO-pyridine-CH2-S(O)-oxadiazole-C6H4-F | | 31 |

30
None means inhibition did not reach to 90% in assay against
replicating Mtb or 99% in assay against non-replicating
Mtb.

TABLE

Antimycobacterial activity of the compounds was determined using the
fluorescent assay, either using the CFU assay described in Example 1.

| Compound | Against Replicating Mtb IC90 (uM) | Against carbon starving non-replicating Mtb IC90 (uM) |
|---|---|---|
| dioxane-CH2CH2-S-oxadiazole-Ph | | 10 |
| 4-F-C6H4-CH2-S-oxadiazole-Ph | | 62 |
| MeO-CH2CH2-S-oxadiazole-Ph | | 4 |
| pyridine-CH2-S-oxadiazole-Ph | 99% @ 125 | 4 |

TABLE-continued
Antimycobacterial activity of the compounds was determined using the fluorescent assay, either using the CFU assay described in Example 1.
| Compound | Against Replicating Mtb IC90 (uM) | Against carbon starving non-replicating Mtb IC90 (uM) |
|---|---|---|
| 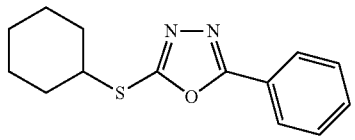 [SMILES: c1ccc(-c2nnc(SC3CCCCC3)o2)cc1] | | 31 |
| 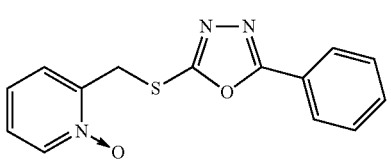 [SMILES: [O-][n+]1ccccc1CSc1nnc(-c2ccccc2)o1] | | None |
| 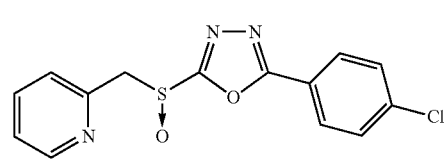 [SMILES: O=S(Cc1ccccn1)c1nnc(-c2ccc(Cl)cc2)o1] | | 10 |
| 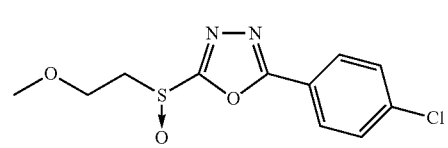 [SMILES: COCCS(=O)c1nnc(-c2ccc(Cl)cc2)o1] | | 10 |
| 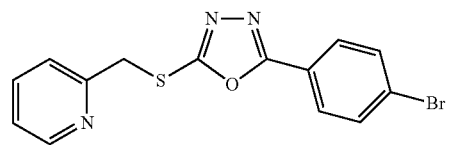 [SMILES: Brc1ccc(-c2nnc(SCc3ccccn3)o2)cc1] | | <8 |
| 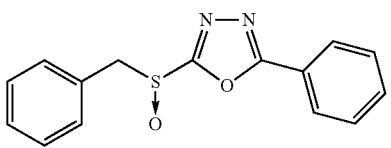 [SMILES: O=S(Cc1ccccc1)c1nnc(-c2ccccc2)o1] | 100% @ 31 | 4 |
| 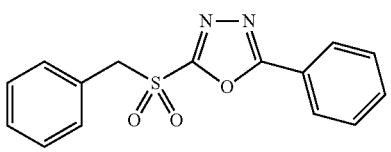 [SMILES: O=S(=O)(Cc1ccccc1)c1nnc(-c2ccccc2)o1] | | 62 |
| 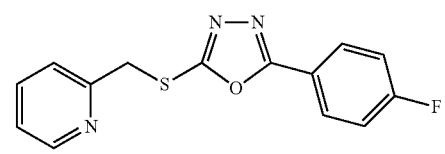 [SMILES: Fc1ccc(-c2nnc(SCc3ccccn3)o2)cc1] | 98.5% @ 16 | 99% @ 4 |
| 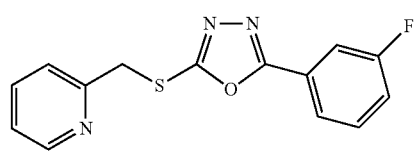 [SMILES: Fc1cccc(-c2nnc(SCc3ccccn3)o2)c1] | 31 | <8 |

TABLE-continued

Antimycobacterial activity of the compounds was determined using the fluorescent assay, either using the CFU assay described in Example 1.

| Compound | Against Replicating Mtb IC90 (uM) | Against carbon starving non-replicating Mtb IC90 (uM) |
|---|---|---|
| (pyridin-2-ylmethylthio-oxadiazole-3-bromophenyl) | 96% @ 62 | <8 |
| (benzyltriazole-CH2-S(O)-oxadiazole-4-chlorophenyl) | 100% @ 62 | 100% @ 31 |
| (benzyltriazole-CH2-S-oxadiazole-4-chlorophenyl) | 98% @ 125 | 99% @ 4 |
| (pyridin-2-ylmethylthio-oxadiazole-3-methoxyphenyl) | 99% @ 62 | 99% @ 16 |
| (5-methoxypyridin-2-ylmethylthio-oxadiazole-4-chlorophenyl) | 99.5% @ 16 (7 d) | 99% @ 4 |
| (MeO2C-propyl-O-pyridin-CH2-S-oxadiazole-4-chlorophenyl) | 31 | 99% @ 8 |
| (N3-ethyl-O-ethyl-NH-C(O)-propyl-O-pyridin-CH2-S-oxadiazole-4-chlorophenyl) | | 98% @ 8 |

TABLE-continued

Antimycobacterial activity of the compounds was determined using the fluorescent assay, either using the CFU assay described in Example 1.

| Compound | Against Replicating Mtb IC90 (uM) | Against carbon starving non-replicating Mtb IC90 (uM) |
|---|---|---|
| 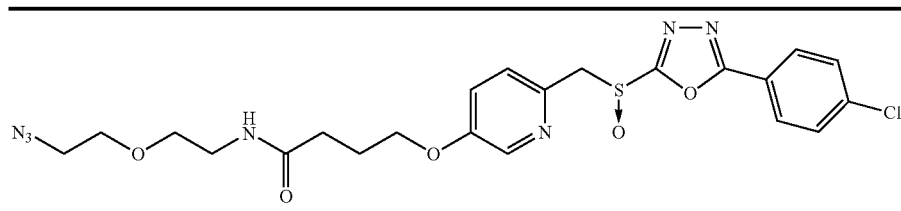 | | 97% @ 8 |

What is claimed is:

1. A method of treating tuberculosis comprising administering to a subject a pharmaceutical composition comprising a compound of Formula I-b, I-c, I-d, or I-e, or a pharmaceutically acceptable salt, ester or prodrug thereof:

I-b, I-c, I-d, I-e wherein
R$_3$ is null, O, H, optionally substituted C$_1$-C$_6$ linear or branched alkyl, or

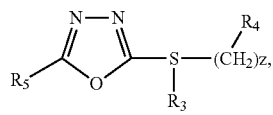

R$_4$ is —C≡CH, —C≡C(CH$_2$)$_t$OH, —O(CH$_2$)$_u$CH$_3$, —O(CH$_2$)$_q$C(═O)O(CH$_2$)$_p$CH$_3$,

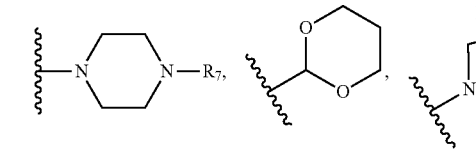

-continued

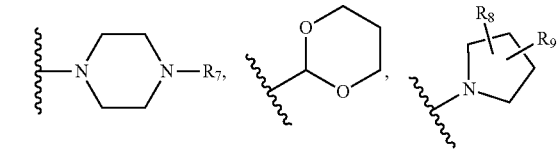

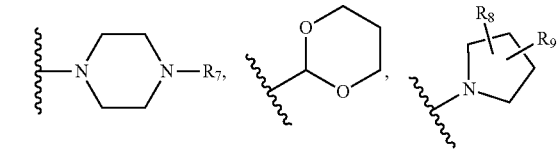

optionally substituted C$_1$-C$_6$ alkoxy, optionally substituted alkylamino, or C$_3$-C$_6$ carbocycle;

R$_5$ is

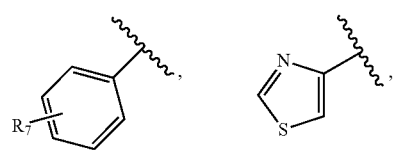

and, z is 1-6, wherein

R$_6$ and R$_{10}$ are each independently H, halo, C$_1$-C$_6$ linear or branched alkyl, C$_1$-C$_6$ haloalkyl, cyano, C$_1$-C$_6$ alkoxy, halogen substituted C$_1$-C$_6$ alkoxy, OH, —O(CH$_2$)$_q$C(═O)O(CH$_2$)$_p$CH$_3$, —O(CH$_2$)$_q$C(═O)N(H)(CH$_2$)$_p$O(CH$_2$)$_m$N$_3$, —O(CH$_2$)$_q$C≡CH, or

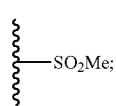

R₇ is H,

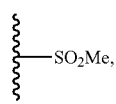

halo, cyano, —C(=O)N(H)(CH₂)$_p$O(CH₂)$_m$N₃, —O(CH₂)$_q$C(=O)N(H)(CH₂)$_p$O(CH₂)$_m$N₃, —O(CH₂)$_m$N₃, —O(CH₂)$_m$C≡CH, C₁-C₆ alkoxy, optionally substituted C₁-C₆ linear or branched alkyl, haloalkyl, optionally substituted aryl; optionally substituted arylalkyl, or halogen substituted C₁-C₆ alkoxy;

R₈ and R₉ are independently H, OH, =O, halo, or C₁-C₆ alkyl;

p and q are independently 1-6; and t and u are independently 0-6, wherein m is 1-6.

2. The method of treating tuberculosis of claim 1, wherein the tuberculosis is a non-replicating tuberculosis.

3. The method of treating tuberculosis of claim 1, wherein the tuberculosis is a replicating tuberculosis.

4. The method of treating tuberculosis of claim 1, wherein the compound is selected from the group consisting of:

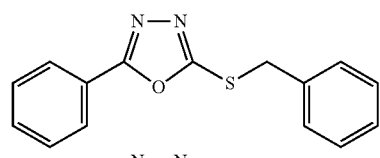

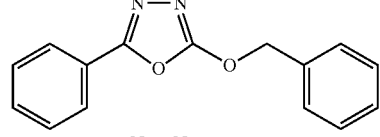

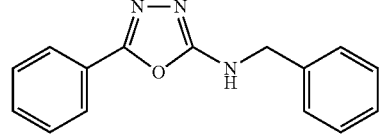

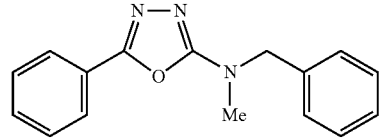

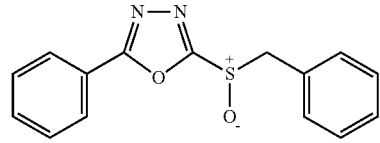

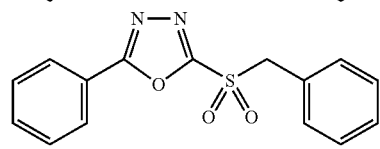

-continued

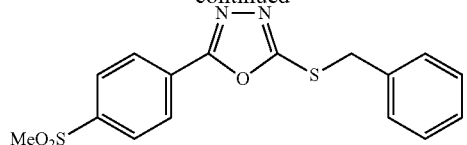

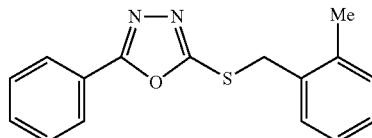

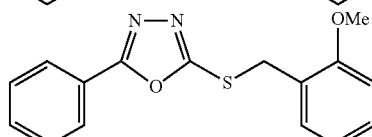

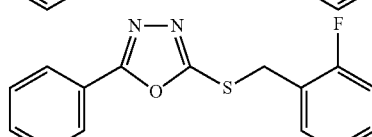

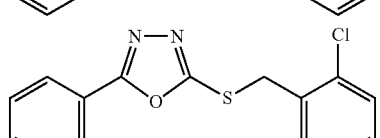

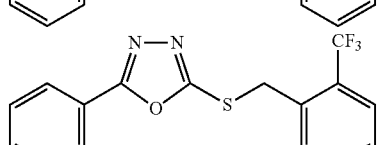

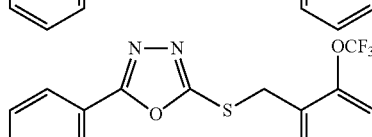

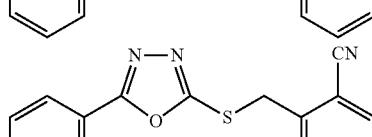

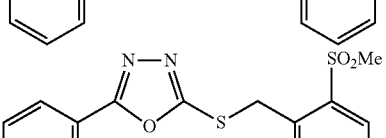

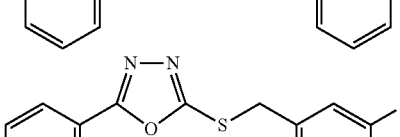

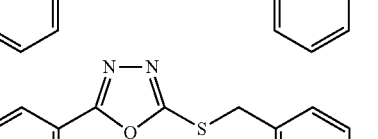

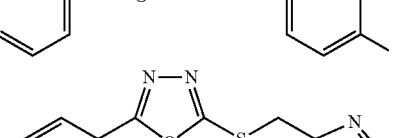

141
-continued
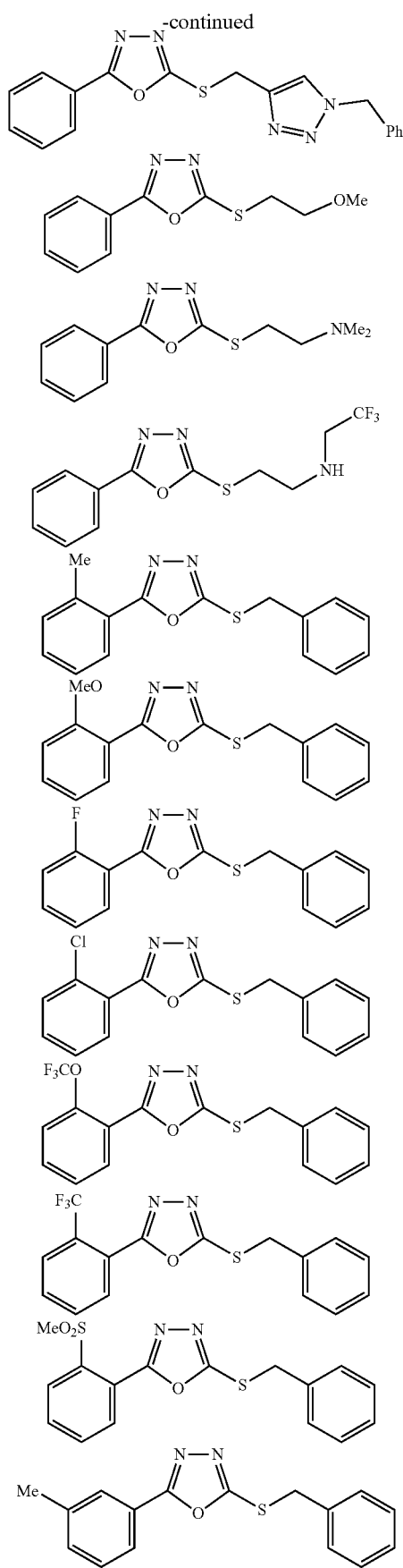
142
-continued
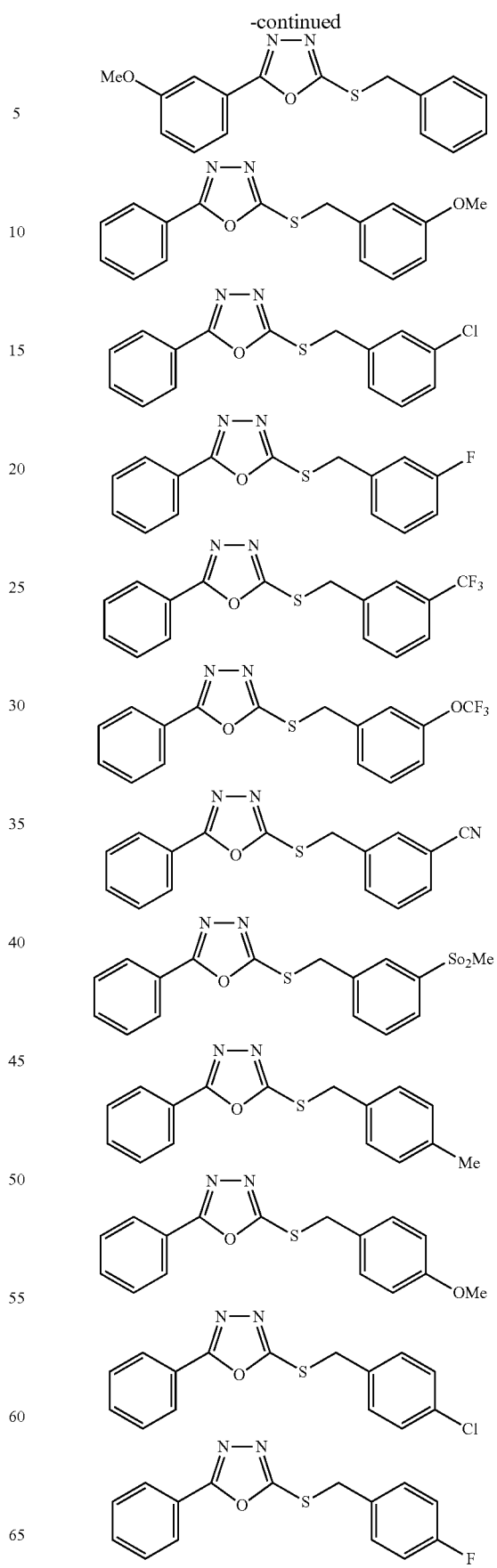

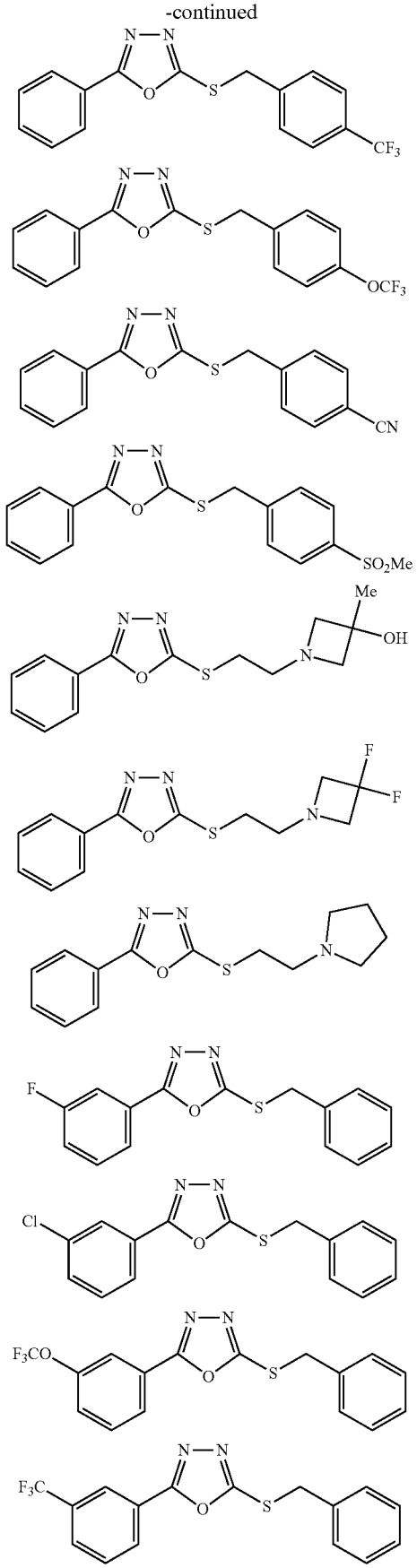
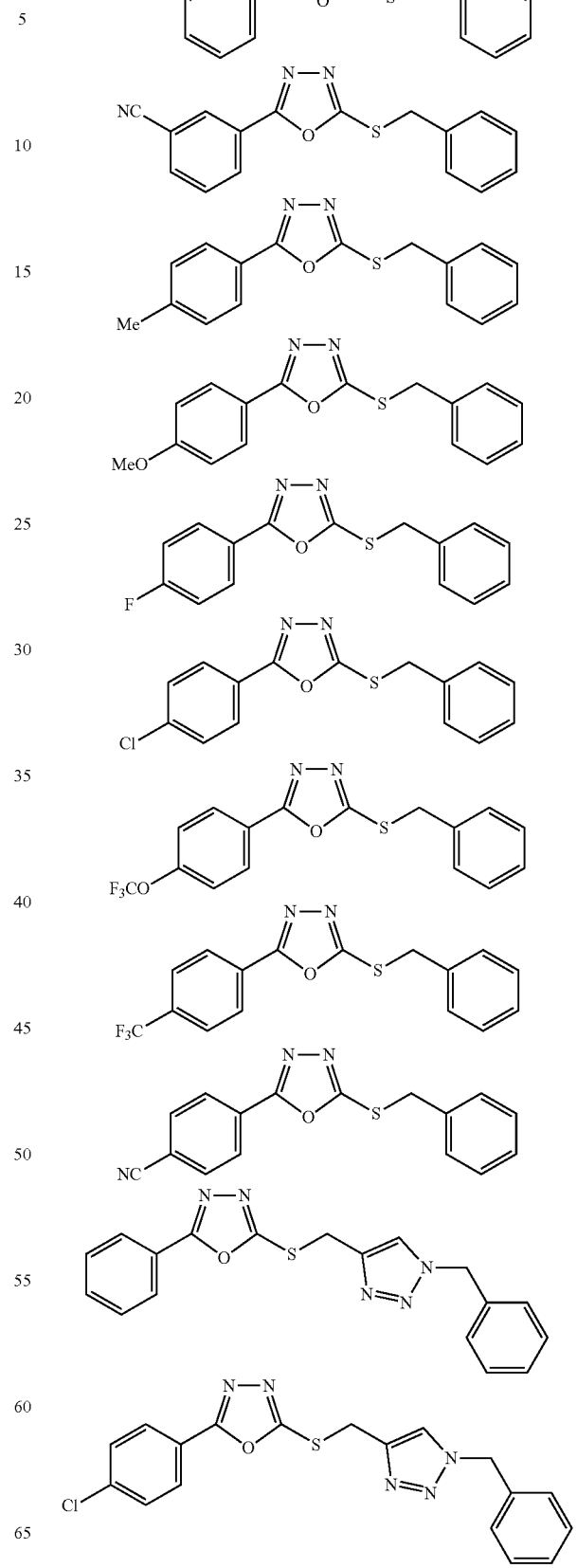

-continued
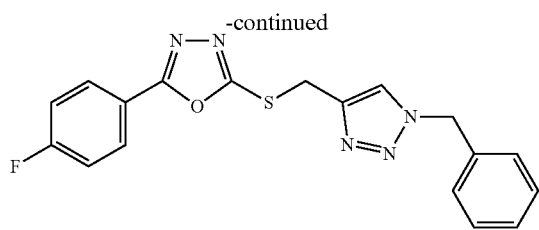
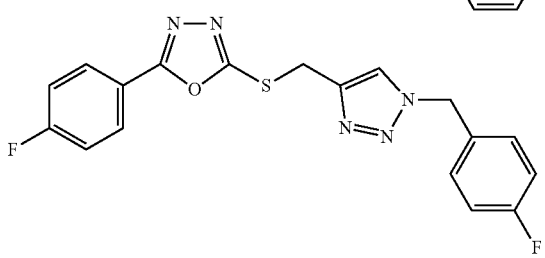
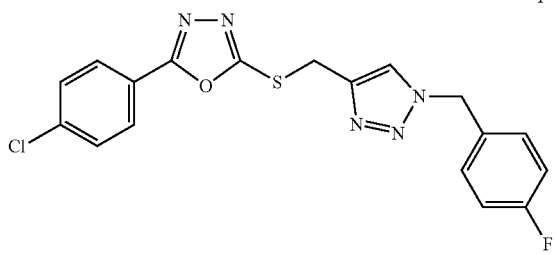
-continued
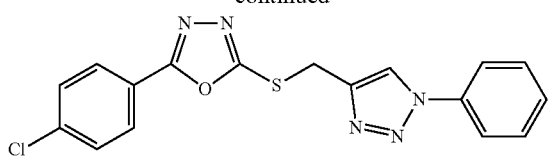
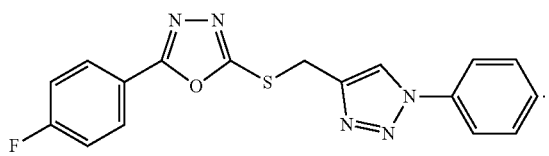
5. The method of treating tuberculosis of claim 1, wherein the compound is:
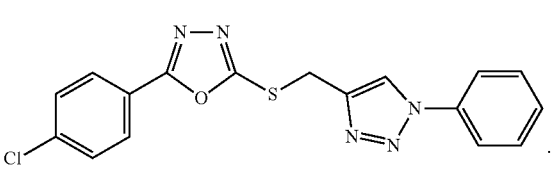 [SMILES: Clc1ccc(-c2nnc(SCc3cn(-c4ccccc4)nn3)o2)cc1]
* * * * *